(12) United States Patent
Mihara et al.

(10) Patent No.: US 10,184,137 B2
(45) Date of Patent: Jan. 22, 2019

(54) METHOD OF PRODUCING ISOPRENE MONOMER

(71) Applicant: AJINOMOTO CO., INC., Tokyo (JP)

(72) Inventors: Yoko Mihara, Kawasaki (JP); Hiroaki Rachi, Kawasaki (JP); Yosuke Nishio, Kawasaki (JP); Yosifovna Joanna Katashkina, Moscow (RU); Dmitrievna Ekaterina Kazieva, Moscow (RU); Georgievna Irina Andreeva, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 705 days.

(21) Appl. No.: 14/670,614

(22) Filed: Mar. 27, 2015

(65) Prior Publication Data
US 2015/0275233 A1 Oct. 1, 2015

(30) Foreign Application Priority Data
Mar. 28, 2014 (RU) .................. 2014112066

(51) Int. Cl.
*C12P 5/02* (2006.01)
*C12N 9/12* (2006.01)
*C12P 9/00* (2006.01)
*C08F 136/08* (2006.01)
*B60C 1/00* (2006.01)
*C12P 5/00* (2006.01)
*C08L 9/00* (2006.01)

(52) U.S. Cl.
CPC .............. *C12P 5/007* (2013.01); *B60C 1/00* (2013.01); *C08F 136/08* (2013.01); *C12N 9/1205* (2013.01); *C12P 9/00* (2013.01); *C12Y 207/01036* (2013.01)

(58) Field of Classification Search
CPC ...... C08F 136/08; C12P 5/007; C12N 9/1205; C12Y 207/01036
USPC ........................................ 435/167
See application file for complete search history.

(56) References Cited

U.S. PATENT DOCUMENTS

| 5,914,245 | A | 6/1999 | Bylina et al. |
| 7,252,985 | B2 | 8/2007 | Cheng et al. |
| 8,173,410 | B2 | 5/2012 | Bott et al. |
| 8,288,148 | B2 | 10/2012 | Cervin et al. |
| 8,709,785 | B2 | 4/2014 | Cervin et al. |
| 8,916,370 | B2 | 12/2014 | Bott et al. |
| 2004/0219629 | A1 | 11/2004 | Cheng et al. |
| 2010/0209977 | A1 | 8/2010 | Takumi et al. |
| 2013/0078699 | A1 | 3/2013 | Cervin et al. |

FOREIGN PATENT DOCUMENTS

| EP | 2 218 729 | A1 | 8/2010 |
| JP | 2006-515174 | | 5/2006 |
| JP | 2007-515169 | | 6/2007 |
| JP | 2010-187552 | | 9/2010 |
| JP | 2011-505841 | A | 3/2011 |
| JP | 2011-518564 | A | 6/2011 |
| JP | 2013-216850 | | 10/2013 |
| WO | WO 2010/031062 | A1 | 3/2010 |
| WO | WO 2010/031077 | A1 | 3/2010 |

OTHER PUBLICATIONS

Kuzuyama, "Mevalonate and Nonmevalonate Pathways for the Biosynthesis of Isoprene Units," Biosci. Biotechnol. Biochem., 66(8), 1619-1627, 2002.*
International Search Report and Written Opinion dated Sep. 28, 2015 in PCT/JP2015/060529 filed Mar. 27, 2015.
Rie Matsumi, et al. "Isoprenoid biosynthesis in Archaea—Biochemical and evolutionary implications" Research in Microbiology, vol. 162, No. 1, XP002740471, Jan. 2011, pp. 39-52 and Cover Pages.
"RecName: Full=Mevalonate kinase {ECO:0000256 | HAMAP-Rule:MF_00217};Short=MK {ECO:0000256 | HAMAP-Rule:MF_00217}, Short=MVK (ECO:0000256 | HAMAP-Rule:MF_00217): EC=2.7.1.36 (ECO:0000256 | HAMAP-Rule:MF_00217)"Database UniProt [Online], Database accession No. D1YZ39, XP002740472, Feb. 9, 2010, 2 Pages.
"SubName: Full=Mevalonate kinase {ECO:0000313 | EMBL:AEK36255.1}; EC=2.7.1.36 {ECO:0000313 | EMBL:AEK36255.1}" Database UniProt [Online], Database Accession No. G0HC93, XP002744231, Oct. 19, 2011, 2 Pages.
"RecName: Full=Mevalonate kinase (ECO:0000256 | HAMAP-Rule:MF_00217); Short=MK (ECO:0000256 | HAMAP-Rule:MF_00217); Short=MVK (ECO:0000256 | HAMAP-Rule:MF_00217); EC=2.7.1.36 (ECO:0000256 | HAMAP-Rule:MF_00217)" Database UniProt [Online], Database Accession No. F4BZB3, XP002744232, Jun. 28, 2011, 2 Pages.
"RecName: Full=Mevalonate kinase (ECO:0000256 | HAMAP-Rule:MF_00217); Short=MK [ECO:0000256 | HAMAP-Rule:MF_00217); Short=MVK (ECO:0000256 | HAMAP-Rule:MF_00217); EC=2.7.1.36 (ECO:0000256 | HAMAP-Rule:MF_00217)" Database UniProt [Online], Database Accession No. A9A427, XP002744233, Jan. 15, 2008, 2 Pages.
J. Kesselmeier, et al., "Biogenic Volatile Organic Compounds (VOC): An Overview on Emission, Physiology and Ecology" Journal of Atmospheric Chemistry, vol. 33, 1999, pp. 23-88.

(Continued)

*Primary Examiner* — Fred M Teskin
(74) *Attorney, Agent, or Firm* — Oblon, McClelland, Maier & Neustadt, L.L.P.

(57) ABSTRACT

A host cell includes a heterogeneous expression unit including: (a) a polynucleotide encoding a mevalonate kinase derived from a microorganism belonging to a genus selected from *Methanocella, Corynebacterium, Methanosaeta,* and *Nitrosopumilus,* and (b) a promoter operatively linked to the polynucleotide. The host cell is used to produce mevalonate kinase, mevalonate-5-phosphate, and isoprenoid compounds.

32 Claims, 15 Drawing Sheets

Specification includes a Sequence Listing.

(56) References Cited

OTHER PUBLICATIONS

Russell K. Monson, et al., "Relationships among Isoprene Emission Rate, Photosynthesis, and Isoprene Synthase Activity as Influenced by Temperature" Plant Physiol., vol. 98, 1992, pp. 1175-1180.

Jennifer Kuzma, et al., "Leaf Isoprene Emission Rate is Dependent on Leaf Development and the Level of Isoprene Synthase" Plant Physiol., vol. 101, 1993, pp. 435-440.

Yuliya A. Primak, et al., "Characterization of a Feedback-Resistant Mevalonate Kinase from the Archaeon *Methanosarcina mazei*" Applied and Environmental Microbiology, vol. 77, No. 21, Nov. 2011, pp. 7772-7778.

Vincent JJ Martin, et al., "Engineering a mevalonate pathway in *Escherichia coli* for production of terpenoids" Nature Biotechnology, vol. 21, No. 7, Jul. 2003, pp. 796-802.

Office Action dated Oct. 2, 2018, in corresponding Japanese Patent Application No. 2016-550891 (with English-language Translation).

\* cited by examiner

A)

B)

C)

A)

B)

C)

METHOD OF PRODUCING ISOPRENE MONOMER

CROSS-REFERENCE TO RELATED APPLICATIONS

This application claims priority benefit of Russian Patent Application No. 2014112066, filed Mar. 28, 2014, the disclosure of which is incorporated herein by reference in its entirety.

BACKGROUND OF THE INVENTION

Field of the Invention

The present invention relates to host cells that may be used to prepare mevalonate kinase, mevalonate-5-phosphate, and isoprenoid compounds.

Discussion of the Background

Natural rubber is a very important raw material in tire and rubber industries. While its demand will be expanded in the future due to motorization mainly in emerging countries, it is laborious to increase the number of agricultural farms dedicated to rubber in view of regulation of deforestation and competition with palm plantations. Thus, the balance of demand and supply is predicted to become tight. Synthesized polyisoprene is available as a substitute for natural rubber. Polyisoprene's raw material monomer (isoprene (2-methyl-1,3-butadiene)) is mainly obtained by extracting from a C5 fraction obtained by cracking of naphtha. However in recent years, with the use of light feed crackers, an amount of produced isoprene tends to decrease and reliable supply is a concern. Also in recent years, since variation in oil prices impacts production greatly, there is a need to establish a system in which isoprene derived from non-oil sources is produced inexpensively to stably ensure the supply of isoprene monomer.

In view of such need, a method in which the isoprene monomer is produced using a transformant obtained by introducing an isoprene synthase gene and a mutant thereof derived from isolated kudzu or poplar into a microorganism for fermental production has been described in JP 2011-505841 and JP 2011-518564. It has been described in Yuliya, A., et al., Appl. Environ. Microbiol., vol. 77 (No. 21), pp. 7772-77-78, 2011, that mevalonate kinase, an enzyme in a mevalonate pathway, is inhibited by DMAPP, a metabolite in the mevalonate pathway.

A method of producing an isoprene monomer using a transformant obtained by introducing a mevalonate kinase derived from isolated *Methanosarcina mazei* into a microorganism for fermental production has been described in WO 2010/031062. Also, a method of producing an isoprene monomer using a transformant obtained by introducing a mevalonate kinase derived from actinomyces or lactobacillus into a microorganism for fermental production has been described in WO 2010/031077.

Further, as described in Martin, V. J., et al., Nature Biotechnology, vol. 21 (No. 7), pp. 796-802, 2003, isoprene is one of the isoprenoids, and a reaction catalyzed by the mevalonate kinase is a rate-limiting step when isoprenoids are produced by fermentation of microorganisms.

Other relevant description can be found in WO 2010/031062, WO 2010/031077, Kesselmeier, J., et al., Journal of Atmospheric Chemistry, vol. 33, pp. 23-88, 1999, Monson, R. K., et al., Plant Physiol., vol. 98, pp. 1175-1180, 1992, and Kuzma, J., et al., Plant Physiol., vol. 101, pp. 435-440, 1993.

BRIEF SUMMARY OF THE INVENTION

An object of the present invention is to provide, in various exemplary embodiments, an alternative method of producing an isoprene monomer.

As a result of extensive study, the present inventors have discovered that a mevalonate kinase derived from a given microorganism can be used to produce an isoprene monomer.

Employing various exemplary embodiments of the present invention, an excellent system for the production of isoprene monomer can be established.

In various exemplary embodiments, a host cell according to the present invention includes a heterogeneous expression unit. In embodiments, the heterogenous expression unit includes: (a) a polynucleotide encoding a mevalonate kinase derived from a microorganism belonging to a genus selected from *Methanocella, Corynebacterium, Methanosaeta*, and *Nitrosopumilus*, and (b) a promoter operatively linked to the polynucleotide.

In various exemplary embodiments, in a host cell according to the present invention, an exemplary polynucleotide encoding a mevalonate kinase encodes a mevalonate kinase having an amino acid sequence having 70% or greater identity with an amino acid sequence selected from SEQ ID NO:1, SEQ ID NO:3, SEQ ID NO:6, and SEQ ID NO:9.

In various exemplary embodiments, a host cell according to the present invention is a microorganism belonging to the family Enterobacteriaceae.

In various exemplary embodiments, a host cell according to the present invention includes a first additional heterogenous expression unit. In embodiments, the first additional heterogenous expression unit includes: (a1) a polynucleotide encoding an enzyme involved in a methylerythritol phosphate pathway, and (b1) a promoter operatively linked to the polynucleotide.

In various exemplary embodiments, a host cell according to the present invention includes a second additional heterogenous expression unit. In embodiments, the second additional heterogenous expression unit includes: (a2) a polynucleotide encoding an enzyme involved in a mevalonate pathway, and (b2) a promoter operatively linked to the polynucleotide.

In various exemplary embodiments, a host cell according to the present invention is a microorganism belonging to the genus *Escherichia*.

In various exemplary embodiments, a host cell according to the present invention is *Escherichia coli*.

In various exemplary embodiments, a host cell according to the present invention is a microorganism belonging to the genus *Pantoea*.

In various exemplary embodiments, a host cell according to the present invention is *Pantoea ananatis*.

In various exemplary embodiments, a host cell according to the present invention includes a genomic region in which a crt operon is disrupted.

In various exemplary embodiments, a host cell according to the present invention includes a third additional heterogenous expression unit. In embodiments, the third additional heterogenous expression unit includes: (a3) a polynucleotide encoding an isoprene synthase, and (b3) a promoter operatively linked to the polynucleotide.

In various exemplary embodiments, a method of producing a mevalonate kinase according to the present invention includes culturing an exemplary host cell according to the present invention, and extracting or purifying the mevalonate kinase from the culture.

In various exemplary embodiments, a method of producing mevalonate-5-phosphate according to the present invention includes culturing an exemplary host cell according to the present invention in the presence of mevalonic acid or a precursor to mevalonic acid, and extracting or purifying mevalonate-5-phosphate from the culture. Examples of precursor to mevalonic acid are acetyl-CoA, acetoacetyl-CoA, malonyl-CoA and HMG-CoA.

In various exemplary embodiments, a method of producing an isoprenoid compound according to the present invention includes culturing an exemplary host cell according to the present invention, and extracting or purifying the isoprenoid compound from the culture.

In various exemplary embodiments, a method of producing an isoprenoid compound according to the present invention involves producing an isoprene monomer.

In various exemplary embodiments, a method of producing an isoprene polymer according to the present invention includes preparing an isoprene monomer by an exemplary method according to the present invention, and polymerizing the isoprene monomer to form the isoprene polymer.

In various exemplary embodiments, a polymer according to the present invention is obtained by polymerizing an isoprenoid compound produced by an exemplary method according to the present invention.

In various exemplary embodiments, a rubber composition according to the present invention includes an exemplary polymer according to the present invention.

In various exemplary embodiments, a tire according to the present invention is prepared from a rubber composition according to the present invention.

BRIEF DESCRIPTION OF THE FIGURES

A more complete appreciation of the invention and many of the attendant advantages thereof will be readily obtained as the same become better understood by reference to the following detailed description when considered in connection with the accompanying drawings, wherein.

DETAILED DESCRIPTION OF THE INVENTION

Figure 1:
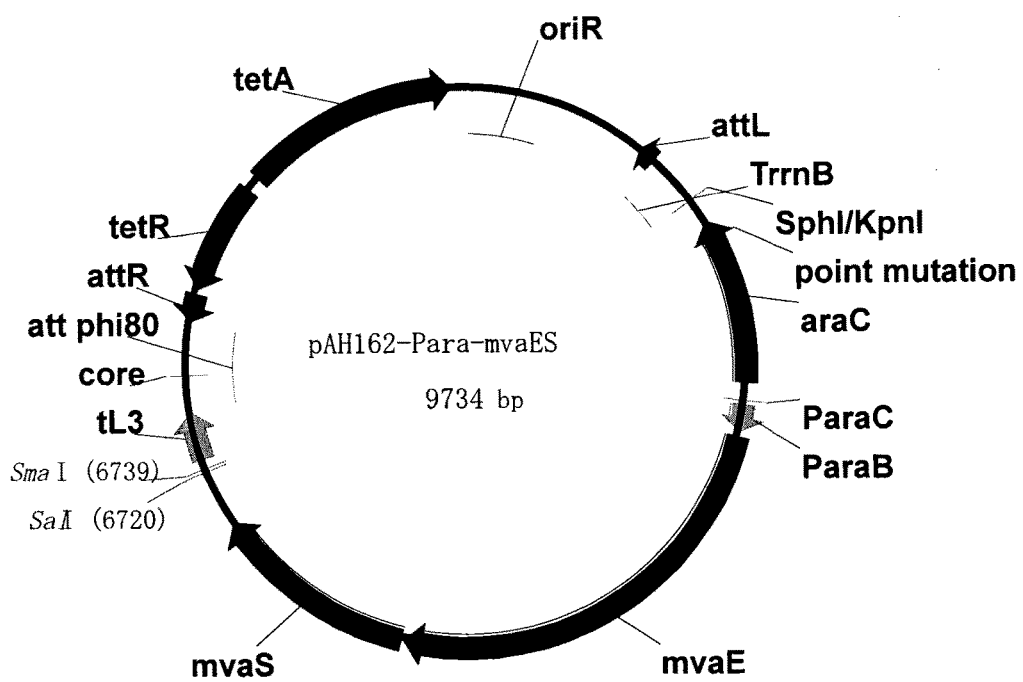
FIG. 1 is a schematic depiction of the pAH162-Para-mvaES plasmid.

Other features of the invention will become apparent in the course of the following descriptions of exemplary embodiments which are given for illustration of the invention and are not intended to be limiting thereof.

Embodiments of the present invention provide an alternative method of producing an isoprene monomer. More specifically, embodiments of the present invention provide a transformant that expresses mevalonate kinase derived from a microorganism belonging to the genus *Methanocella*, the genus *Corynebacterium*, the genus *Methanosaeta,* or the genus *Nitrosopumilus;* a method of producing the mevalonate kinase comprising forming the mevalonate kinase using the transformant; a method of producing mevalonate-5-phosphate comprising forming mevalonate-5-phosphate from mevalonic acid using the transformant; a method of producing an isoprene monomer comprising forming the isoprene monomer using the transformant; and the like.

Accordingly, various exemplary embodiments of the present invention include the following.

[1] A transformant that expresses a mevalonate kinase derived from a microorganism belonging to the genus *Methanocella*, the genus *Corynebacterium*, the genus *Methanosaeta*, or the genus *Nitrosopumilus*.

[2] The transformant as described above, wherein the mevalonate kinase comprises an amino acid sequence showing 70% or more identity to an amino acid sequence of SEQ ID NO:1, SEQ ID NO:3, SEQ ID NO:6, or SEQ ID NO:9, and has a mevalonate kinase activity.

[3] The transformant as described above, wherein the transformant is a microorganism belonging to the family Enterobacteriaceae.

[4] The transformant as described above, wherein the transformant has an ability to synthesize dimethylallyl diphosphate via a methylerythritol phosphate pathway.

[5] The transformant as described above, wherein the transformant has an ability to synthesize dimethylallyl diphosphate via a mevalonate pathway.

[6] The transformant as described above, wherein the transformant is a microorganism belonging to the genus *Escherichia*.

[7] The transformant as described above, wherein the transformant is *Escherichia coli*.

[8] The transformant as described above, wherein the transformant is a microorganism belonging to the genus *Pantoea*.

[9] The transformant as described above, wherein the transformant is *Pantoea ananatis*.

[10] The transformant as described above, which possesses a genomic region in which a crt operon is disrupted.

[11] The transformant as described above, expressing further an isoprene synthase.

[12] A method of producing a mevalonate kinase, comprising forming the mevalonate kinase using the transformant as described above.

[13] A method of producing mevalonate-5-phosphate, comprising forming mevalonate-5-phosphate from mevalonic acid using the transformant as described above.

[14] A method of producing an isoprene monomer, comprising forming the isoprene monomer using the transformant as described above.

[15] A method of producing an isoprene polymer, comprising following (I) and (II):

(I) forming the isoprene monomer by the method as described above; and (II) polymerizing the isoprene monomer to form the isoprene polymer.

Of course the present invention is not intended to be limited to the foregoing exemplary embodiments.

In embodiments, the present invention provides a transformant that expresses a mevalonate kinase. The mevalonate kinase is encoded by a gene derived from an organism that is different species from a host for the transformant, and derived from, for example, a microorganism belonging to the genus *Methanocella*, the genus *Corynebacterium*, the genus *Methanosaeta*, or the genus *Nitrosopumilus*. Preferably, the mevalonate kinase is derived from a microorganism belonging to *Corynebacterium variabile*, *Methanocella paludicola*, *Methanosaeta concilii*, or *Nitrosopumilus maritimus*.

In one embodiment, the mevalonate kinase is a protein that comprises an amino acid sequence having 70% or more amino acid sequence identity to an amino acid sequence of SEQ ID NO:1 which can be derived from the genus *Methanocella*, SEQ ID NO:3 which can be derived from the genus *Corynebacterium*, SEQ ID NO:6 which can be derived from the genus *Methanosaeta* or SEQ ID NO:9 which can be derived from the genus *Nitrosopumilus*, and has a mevalonate kinase activity. The amino acid sequence percent identity may be, for example, 75% or more, 80% or more, 85% or more, 90% or more, 95% or more, 96% or more, 97% or more, 98% or more, or 99% or more. The mevalonate kinase activity refers to an activity of phosphorylating mevalonic acid to form mevalonate-5-phosphate (EC No. 2.7.1.36) (hereinafter, the same meaning shall be applied).

The percent identity of the amino acid sequences and the percent identity of the nucleotide sequences as described later can be determined using the BLAST algorithm (Pro. Natl. Acad. Sci. USA, 90, 5873 (1993)) by Karlin and Altschul, and the FASTA algorithm (Methods Enzymol., 183, 63 (1990)) by Pearson. The programs referred to as BLASTP and BLASTN were developed based on the BLAST algorithm (see http://www.ncbi.nlm.nih.gov). Thus, the percent identity of the nucleotide sequences and the amino acid sequences may be calculated using these programs with default settings. Also, for example, a numerical value obtained by calculating similarity as a percentage at a setting of "unit size to compare=2" using the full length of a polypeptide portion encoded in ORF with the software GENETYX Ver. 7.0.9 from Genetyx Corporation employing the Lipman-Pearson method may be used as the homology of the amino acid sequences. The lowest value among the values derived from these calculations may be employed as the percent identity of the nucleotide sequences and the amino acid sequences.

In another embodiment, the mevalonate kinase is a protein that comprises an amino acid sequence having a mutation of one or several amino acids in the amino acid sequence of SEQ ID NO:1, SEQ ID NO:3, SEQ ID NO:6, or SEQ ID NO:9, and has the mevalonate kinase activity. Examples of the mutation of the amino acid residues may include deletion, substitution, addition and insertion of amino acid residues. The mutation of one or several amino acids may be introduced into one region or multiple different regions in the amino acid sequence. The term "one or several" indicates a range in which a three-dimensional structure and an activity of the protein are not impaired greatly. In the case of the protein, the number represented by "one or several" can be, for example, 1 to 100, preferably 1 to 80, more preferably 1 to 50, 1 to 30, 1 to 20, 1 to 10, or 1 to 5. The mevalonate kinase may have a tag for purification, such as a histidine tag.

The mevalonate kinase preferably has an mevalonate kinase activity that is 50% or more, 60% or more, 70% or more, 80% or more, 90% or more, or 95% or more of the mevalonate kinase activity of the protein comprising the amino acid sequence of SEQ ID NO:1, SEQ ID NO:3, SEQ ID NO:6, or SEQ ID NO:9 when measured under the same conditions. Known methods can be used to measure the mevalonate kinase activity (e.g., Andreassi, et al., Biochemistry, 43, 16461-16466, 2004, Fu, et al., Biochemistry, 47, 3715-3724, 2008, Primak, et al., Appl. Environ. Microbiol. 77, 7772-7778).

Also, the mevalonate kinase preferably has an ability of cancelling feedback inhibition by a substrate in a pathway of isoprenoid biosynthesis (e.g., phosphomevalonic acid, diphosphomevalonic acid, isopentenyl-2-phosphate, dimethylallyl pyrophosphate, geranyl pyrophosphate, farnesyl pyrophosphate) (Primak, et al., Appl. Environ. Microbiol. 77, 7772-7778), and for example, preferably has the ability of cancelling feedback inhibition, that is 50% or more, 60% or more, 70% or more, 80% or more, 90% or more, or 95% or more of the ability of cancelling feedback inhibition possessed by the protein consisting of the amino acid sequence of SEQ ID NO:1, SEQ ID NO:3, SEQ ID NO:6, or SEQ ID NO:9 when measured under the same conditions.

In the mevalonate kinase, the mutation may be introduced into sites in a catalytic domain and sites other than the catalytic domain as long as an objective activity is retained. The positions of amino acid residues to be mutated which are capable of retaining the objective activity are understood by a person skilled in the art (Bai, et al., US 2007/0141685 and US 2007/0286850). Specifically, a person skilled in the art can recognize a correlation between structure and function, since a person skilled in the art can 1) compare the amino acid sequences of multiple proteins having the same type of activity (e.g., the amino acid sequences of SEQ ID NO:1, SEQ ID NO:3, SEQ ID NO:6, SEQ ID NO:9 and SEQ ID NO:12), 2) clarify regions that are relatively conserved and regions that are not relatively conserved, and then 3) predict regions capable of playing a functionally important role and regions incapable of playing a functionally important role from the regions that are relatively conserved and the regions that are not relatively conserved, respectively. Therefore, a person skilled in the art can identify the positions of the amino acid residues to be mutated in the amino acid sequence of the mevalonate kinase.

When the amino acid residue is mutated by substitution, the substitution of the amino acid residue may be conservative substitution. As used herein, the term "conservative substitution" refers to substitution of a certain amino acid residue with an amino acid residue having a similar side chain. Families of amino acid residues having similar side chains are well-known in the art. Examples of such families may include amino acids having a basic side chain (e.g., lysine, arginine, histidine), amino acids having an acidic side chain (e.g., aspartic acid, glutamic acid), amino acids having a non-charged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a branched side chain at position β (e.g., threonine, valine, isoleucine), amino acids having an aromatic side chain (e.g., tyrosine, phenylalanine, tryptophan, histidine), amino acids having a hydroxyl group-containing (e.g., alcoholic, phenolic) side chain (e.g., serine, threonine, tyrosine), and amino acids having a sulfur-containing side chain (e.g., cysteine, methionine). Preferably, the conservative substitution of the amino acids may be the substitution between aspartic acid and glutamic acid, the substitution among arginine, lysine and histidine, the substitution between tryptophan and phenylalanine, the substitution between phenylalanine and valine, the substitution among leucine, isoleucine and alanine, and the substitution between glycine and alanine.

Embodiments of the transformant of the present invention can be obtained by transforming a host cell with an expression vector for a desired protein such as the above mevalonate kinase. In embodiments, the transformant of the present invention expressing a desired protein comprises an expression unit comprising a polynucleotide encoding the desired protein and a promoter operatively linked thereto, which are contained in the expression vector. In the expression unit, one of the polynucleotide encoding the desired protein and the promoter is not inherent in the host cell. Therefore, the expression unit may be a heterogenous expression unit. Preferably, both the polynucleotide encoding the desired protein and the promoter are not inherent in the host cell. The promoter may be homologous or heterologous to the polynucleotide encoding the desired protein. The expression unit may further comprise additional elements such as a terminator, a ribosome-binding site, and a drug-resistance gene. The expression unit may be DNA or RNA and is preferably DNA. Examples of the desired protein include, but not limited to, a mevalonate kinase, an isoprene synthase, one or more enzymes involved in a methylerythritol phosphate pathway, and one or more enzymes involved in a mevalonate pathway.

In embodiments, in the expression vector, a polynucleotide encoding the mevalonate kinase may comprise a polynucleotide that comprises a nucleotide sequence having 70% or more nucleotide sequence identity to a nucleotide sequence of SEQ ID NO:2 which can be derived from the genus *Methanocella*, SEQ ID NO:4 or SEQ ID NO:5 which can be derived from the genus *Corynebacterium*, SEQ ID NO:7 or SEQ ID NO:8 which can be derived from the genus *Methanosaeta* or SEQ ID NO:10 or SEQ ID NO:11 which can be derived from the genus *Nitrosopumilus*, and encodes a protein having the mevalonate kinase activity. The nucleotide sequence percent identity may be 70% or more, 75% or more, 80% or more, 85% or more, 90% or more, 95% or more, 96% or more, 97% or more, 98% or more, or 99% or more.

In embodiments, the polynucleotide encoding the mevalonate kinase is a polynucleotide that hybridizes with a polynucleotide consisting of a nucleotide sequence complementary to a nucleotide sequence of SEQ ID NO:2, SEQ ID NO:4, SEQ ID NO:5, SEQ ID NO:7, SEQ ID NO:8, SEQ ID NO:10 or SEQ ID NO:11 under a stringent condition, and encodes the protein having the mevalonate kinase activity. The "stringent condition" refers to a condition where a so-called specific hybrid is formed whereas a non-specific hybrid is not formed. For example, such a condition is the condition where substantially the same polynucleotides having the high identity, for example, the polynucleotides having the percent identity described above hybridize to each other whereas polynucleotides having the lower identity than above do not hybridize to each other. Specifically, such a condition may include hybridization in 6×SCC (sodium chloride/sodium citrate) at about 45° C. followed by one or two or more washings in 0.2×SCC and 0.1% SDS at 50 to 65° C.

In embodiments, the transformant of the present invention may express an isoprene synthase (EC: 4.2.3.27). For example, the isoprene synthase derived from kudzu (*Pueraria montana* var. *lobata*), poplar (*Populus alba* ×*Populus tremula*), and mucuna (*Mucuna bracteata*) can be used as the isoprene synthase.

In one embodiment, the isoprene synthase may be, for example, a protein as follows:

1) a full-length protein which may be derived from kudzu (the amino acid sequence of SEQ ID NO:15);

2) a protein obtained by deleting a chloroplast localization signal from the full-length protein in 1) above (amino acid sequence obtained by deleting amino acid residues at positions 1 to 45 in the amino acid sequence of SEQ ID NO:15);

3) a full-length protein which may be derived from poplar (the amino acid sequence of SEQ ID NO:98);

4) a protein obtained by deleting a chloroplast localization signal from the full-length protein in 3) above (amino acid sequence obtained by deleting amino acid residues at positions 1 to 37 in the amino acid sequence of SEQ ID NO: 98);

5) a full-length protein which may be derived from *mucuna* (the amino acid sequence of SEQ ID NO:99); and 6) a protein obtained by deleting a chloroplast localization signal from the full-length protein in 5) above (amino acid sequence obtained by deleting amino acid residues at positions 1 to 44 in the amino acid sequence of SEQ ID NO:99)).

In a preferred embodiment, the isoprene synthase may be derived from kudzu. In another preferred embodiment, the isoprene synthase may be derived from poplar. In still another preferred embodiment, the isoprene synthase may be derived from *mucuna*.

In another embodiment, the isoprene synthase is a protein that comprises an amino acid sequence having 70% or more amino acid sequence identity to the amino acid sequence of the proteins of 1) to 6) above, and has an isoprene synthase activity. The amino acid sequence percent identity may be, for example, 75% or more, 80% or more, 85% or more, 90% or more, 95% or more, 96% or more, 97% or more, 98% or more, or 99% or more. The isoprene synthase activity refers to an activity of forming isoprene from dimethylallyl diphosphate (DMAPP) (hereinafter, the same meaning shall be applied). The known methods can be used to measure the isoprene synthase activity (e.g., Sharkey, T. D., et al., Plant Physiology, 137, 700-712, 2005).

In still another embodiment, the isoprene synthase is a protein that comprises an amino acid sequence having a mutation of one or several amino acids in the amino acid sequence of the protein of 1) to 6) above, and has an isoprene synthase activity. Examples of the mutation of the amino acid residues may include deletion, substitution, addition and insertion of amino acid residues. The mutation of one or several amino acids may be introduced into one region or multiple different regions in the amino acid sequence. The term "one or several" indicates a range in which a three-dimensional structure and an activity of the protein are not impaired greatly. In the case of the protein, the number represented by "one or several" is, for example, 1 to 100, preferably 1 to 80, more preferably 1 to 50, 1 to 30, 1 to 20, 1 to 10, or 1 to 5. The mevalonate kinase may have a tag for purification, such as a histidine tag.

The isoprene synthase preferably can have an isoprene synthase activity that is 50% or more, 60% or more, 70% or more, 80% or more, 90% or more, or 95% or more of the isoprene synthase activity of the protein of 1) to 6) above when measured under the same conditions. In terms of stability, it is also preferable that the isoprene synthase has a remaining activity that is 30% or more, 40% or more, 50% or more, 60% or more or 65% or more of the original activity when stored in a certain buffer [e.g., a solution of 50 mM Tris-HCl (pH 8.0), and 0.15 mM $MgCl_2$] at 4° C. for 48 hours.

In the isoprene synthase, the mutation may be introduced into sites in a catalytic domain and sites other than the catalytic domain as long as an objective activity is retained. The positions of amino acid residues to be mutated which are capable of retaining the objective activity are understood by a person skilled in the art. Specifically, a person skilled in the art can recognize a correlation between structure and function, since a person skilled in the art can 1) compare the amino acid sequences of multiple proteins having the same type of activity, 2) clarify regions that are relatively conserved and regions that are not relatively conserved, and then 3) predict regions capable of playing a functionally important role and regions incapable of playing a functionally important role from the regions that are relatively conserved and the regions that are not relatively conserved, respectively. Therefore, a person skilled in the art can identify the positions of the amino acid residues to be mutated in the amino acid sequence of the isoprene synthase. When an amino acid residue is mutated by substitution, the substitution of the amino acid residue may be the conservative substitution as described above.

The expression vector for a desired protein such as the mevalonate kinase, which is utilized for making exemplary transformants according to the present invention, is a cell expression vector in which a protein is expressed in a host. The expression vector may also be a non-integrative vector (e.g., a plasmid, a phage, an artificial chromosome) or an integrative vector. The expression vector may be further a DNA vector or an RNA vector.

A known vector suitable for the host cell is used as the cell expression vector. Examples of the expression vector may include ColE-based plasmids typified by pBR322 derivatives, pACYC-based plasmids having a p15A origin, pSC-based plasmids, and mini F plasmids derived from an F factor of Bac and the like in *Escherichia coli*. In addition, expression vectors having a tryptophan promoter such as trc and tac, a lac promoter, a T7 promoter, a T5 promoter, a T3 promoter, an SP6 promoter, an arabinose induction promoter, a cold shock induction promoter, a tetracycline induction promoter, and the like may also be included.

Protein synthesis using the cell expression vector will be described later.

A protein synthesized using the cell expression vector may be purified. Examples of the methods for purification may include methods using a salting-out method and various chromatographic methods. When the expression vector is designed to express a tag sequence such as a histidine tag at an N terminus or a C terminus of the objective protein, a method for purification using affinity chromatography using a substance such as nickel or cobalt having an affinity to this tag can be employed. In addition, ion exchange chromatography, gel filtration chromatography, or the like may be combined appropriately and utilized for the purification.

The transformant of the present invention is one obtained by introducing the expression vector of the present invention into a host. The host used for the present invention may be a bacterium or a fungus such as, for example, a bacterium belonging to the family Enterobacteriaceae. Also, the bacterium may be a gram-positive bacterium or a gram-negative bacterium.

Examples of the gram-positive bacterium may include bacteria belonging to the genera *Bacillus*, *Listeria*, *Staphylococcus*, *Streptococcus*, *Enterococcus*, *Clostridium*, *Corynebacterium*, and *Streptomyces*. Bacteria belonging to the genera *Bacillus* and *Corynebacterium* are preferable.

Examples of the bacteria belonging to the genus *Bacillus* may include *Bacillus subtilis*, *Bacillus anthracis*, and *Bacillus cereus*. *Bacillus subtilis* is more preferable.

Examples of the bacteria belonging to genus the *Corynebacterium* may include *Corynebacterium glutamicum*, *Corynebacterium efficiens*, and *Corynebacterium callunae*. *Corynebacterium glutamicum* is more preferable.

Examples of the gram-negative bacterium may include bacteria belonging to the genera *Escherichia*, *Pantoea*, *Salmonella*, *Vivrio*, *Serratia*, and *Enterobacter*. The bacteria belonging to the genera *Escherichia*, *Pantoea* and *Enterobacter* are preferable.

*Escherichia coli* is preferable as the bacteria belonging to the genus *Escherichia*.

Examples of the bacteria belonging to the genus *Pantoea* may include *Pantoea ananatis*, *Pantoea stewartii*, *Pantoea agglomerans*, and *Pantoea citrea*. *Pantoea ananatis* and *Pantoea citrea* are preferable. Strains exemplified in EP 0

952 221 may be used as the bacteria belonging to the genus *Pantoea*. Examples of representative strains of the bacteria belonging to genus *Pantoea* may include *Pantoea ananatis* AJ13355 strain (FERM BP-6614) and *Pantoea ananatis* AJ13356 strain (FERM BP-6615) disclosed in EP 0 952 221.

Examples of the bacteria belonging to the genus *Enterobacter* may include *Enterobacter agglomerans* and *Enterobacter aerogenes*. *Enterobacter aerogenes* is preferable. The bacterial strains exemplified in EP 0 952 221 may be used as the bacteria belonging to the genus *Enterobacter*. Examples of representative strains of the bacteria belonging to the genus *Enterobacter* may include *Enterobacter agglomerans* ATCC12287 strain, *Enterobacter aerogenes* TACC13048 strain, *Enterobacter aerogenes* NBRC12010 strain (Sakai, S., et al., Biotechnol. Bioeng., vol. 98, pp. 340-348, 2007), and *Enterobacter aerogenes* AJ110637 (FERM BP-10955). The *Enterobacter aerogenes* AJ110637 strain was deposited to International Patent Organism Depositary (IPOD), National Institute of Advanced Industrial Science and Technology (AIST) (Chuo No. 6, Higashi 1-1-1, Tsukuba City, Ibaraki Pref., JP, Postal code 305-8566) as of Aug. 22, 2007, and was transferred to the international deposition based on Budapest Treaty on Mar. 13, 2008, and the deposit number FERM BP-10955 was given thereto.

Examples of the fungus may include microorganisms belonging to the genera *Saccharomyces, Schizosaccharomyces, Yarrowia, Trichoderma, Aspergillus, Fusarium*, and *Mucor*. The microorganisms belonging to the genera *Saccharomyces, Schizosaccharomyces, Yarrowia*, or *Trichoderma* are preferable.

Examples of the microorganisms belonging to the genus *Saccharomyces* may include *Saccharomyces carlsbergensis, Saccharomyces cerevisiae, Saccharomyces diastaticus, Saccharomyces douglasii, Saccharomyces kluyveri, Saccharomyces norbensis*, and *Saccharomyces oviformis*. *Saccharomyces cerevisiae* is preferable.

*Schizosaccharomyces pombe* is preferable as a microorganism belonging to the genus *Schizosaccharomyces*.

*Yarrowia lypolytica* is preferable as a microorganism belonging to the genus *Yarrowia*.

Examples of the microorganisms belonging to the genus *Trichoderma* may include *Trichoderma harzianum, Trichoderma koningii, Trichoderma longibrachiatum, Trichoderma reesei*, and *Trichoderma viride*. *Trichoderma reesei* is preferable.

In addition, the host used for the present invention is not particularly limited as long as the host has an ability to synthesize dimethylallyl diphosphate (DMAPP) via a mevalonic acid (MVA) pathway and/or a methylerythritol phosphate (MEP) pathway that are involved in synthesis of dimethylallyl diphosphate that is a substrate of the isoprene synthase, and may be an insect cell, an animal cell, a plant cell, a bacterial cell, and so forth.

The phrase "ability to synthesize dimethylallyl diphosphate (DMAPP)" is used with reference to Michelle C. Y. Chang and Jay D. Keasling, Nature Chemical Biology 2, 674-681 (2006).

The phrase "mevalonic acid (MVA) pathway" is used with reference to Kuzuyama, T., and Seto, H., Proc Jpn Acad Ser B Phys Biol Sci. 88,41-52 (2012), and Miziorko, H. M., Arch Biochem Biophys. 505,131-143 (2011).

The phrase "methylerythritol phosphate (MEP) pathway" is used with reference to Kuzuyama, T., and Seto, H., Proc Jpn Acad Ser B Phys Biol Sci. 88,41-52 (2012), and Gräwert, T., et al., Cell Mol Life Sci. 68, 3797-3814 (2011).

In embodiments of the transformant of the present invention, the pathway to synthesize dimethylallyl diphosphate (DMAPP) that is the substrate of the isoprene synthase may be enhanced. For such an enhancement, an expression vector that expresses an isopentenyl-diphosphate delta isomerase having an ability to convert isopentenyl diphosphate (IPP) into dimethylallyl diphosphate (DMAPP) may be introduced into the transformant of the present invention. An expression vector that expresses one or more enzymes involved in the mevalonate pathway and/or methylerythritol phosphate pathway associated with formation of IPP and/or DMAPP may also be introduced into the transformant of the present invention. The expression vector for such an enzyme may be a plasmid or an integrative vector. The expression vector for such an enzyme may also be a DNA vector or an RNA vector. The expression vector for such an enzyme may express further a plurality of enzymes (e.g., one, two, three or four or more) involved in the mevalonate pathway and/or the methylerythritol phosphate pathway, and may be, for example, an expression vector for polycistronic mRNA. Origin of one or more enzymes involved in the mevalonate pathway and/or the methylerythritol phosphate pathway may be homologous or heterologous to the host. When the origin of the enzyme involved in the mevalonate pathway and/or the methylerythritol phosphate pathway is heterologous to the host, for example, the host may be a bacterium as described above (e.g., *Escherichia coli*) and the enzyme involved in the mevalonate pathway may be derived from a fungus (e.g., *Saccharomyces cerevisiae*). In addition, when the host inherently produces the enzyme involved in the methylerythritol phosphate pathway, an expression vector to be introduced into the host may express one or a plurality of enzymes (e.g., one, two, three or four or more) involved in the mevalonate pathway.

Examples of isopentenyl-diphosphate delta isomerase (EC: 5.3.3.2) may include Idi1p (ACCESSION ID NP_015208), AT3G02780 (ACCESSION ID NP_186927), AT5G16440 (ACCESSION ID NP_197148) and Idi (ACCESSION ID NP_417365).

Examples of the enzymes involved in the mevalonate (MVA) pathway may include mevalonate kinase (EC: 2.7.1.36; example 1, Erg12p, ACCESSION ID NP_013935; example 2, AT5G27450, ACCESSION ID NP_001190411), phosphomevalonate kinase (EC: 2.7.4.2; example 1, Erg8p, ACCESSION ID NP_013947; example 2, AT1G31910, ACCESSION ID NP_001185124), diphosphomevalonate decarboxylase (EC: 4.1.1.33; example 1, Mvd1p, ACCESSION ID NP_014441; example 2, AT2G38700, ACCESSION ID NP_181404; example 3, AT3G54250, ACCESSION ID NP_566995), acetyl-CoA-C-acetyltransferase (EC: 2.3.1.9; example 1, Erg10p, ACCESSION ID NP_015297; example 2, AT5G47720, ACCESSION ID NP_001032028; example 3, AT5G48230, ACCESSION ID NP_568694), hydroxymethylglutaryl-CoA synthase (EC: 2.3.3.10; example 1, Erg13p, ACCESSION ID NP_013580; example 2, AT4G11820, ACCESSION ID NP_192919; example 3, MvaS, ACCESSION ID AAG02438), hydroxymethylglutaryl-CoA reductase (EC: 1.1.1.34; example 1, Hmg1p, ACCESSION ID NP_013555; example 2, Hmg1p, ACCESSION ID NP_013636; example 3, AT1G76490, ACCESSION ID NP_177775; example 4, AT2G17370, ACCESSION ID NP_179329, EC: 1.1.1.88, example, MvaA, ACCESSION ID P13702), and acetyl-CoA-C-acetyltransferase/hydroxymethylglutaryl-CoA reductase (EC: 2.3.1.9/1.1.1.34, example, MvaE, ACCESSION ID AAG02439).

Examples of the enzymes involved in the methylerythritol phosphate (MEP) pathway may include 1-deoxy-D-xylulose-5-phosphate synthase (EC: 2.2.1.7, example 1, Dxs, ACCESSION ID NP_414954; example 2, AT3G21500, ACCESSION ID NP_566686; example 3, AT4G15560, ACCESSION ID NP_193291; example 4, AT5G11380, ACCESSION ID NP_001078570), 1-deoxy-D-xylulose-5-phosphate reductoisomerase (EC: 1.1.1.267; example 1, Dxr, ACCESSION ID NP_414715; example 2, AT5G62790, ACCESSION ID NP_001190600), 4-diphosphocytidyl-2-C-methyl-D-erythritol synthase (EC: 2.7.7.60; example 1, IspD, ACCESSION ID NP_417227; example 2, AT2G02500, ACCESSION ID NP_565286), 4-diphosphocytidyl-2-C-methyl-D-erythritol kinase (EC: 2.7.1.148; example 1, IspE, ACCESSION ID NP_415726; example 2, AT2G26930, ACCESSION ID NP_180261), 2-C-methyl-D-erythritol-2,4-cyclodiphosphate synthase (EC: 4.6.1.12; example 1, IspF, ACCESSION ID NP_417226; example 2, AT1G63970, ACCESSION ID NP_564819), 1-hydroxy-2-methyl-2-(E)-butenyl-4-diphosphate synthase (EC: 1.17.7.1; example 1, IspG, ACCESSION ID NP_417010; example 2, AT5G60600, ACCESSION ID NP_001119467), and 4-hydroxy-3-methyl-2-butenyl diphosphate reductase (EC: 1.17.1.2; example 1, IspH, ACCESSION ID NP_414570; example 2, AT4G34350, ACCESSION ID NP_567965).

The introduction of the expression vector incorporating a gene into a host (transformation) can be carried out using known methods. Examples of such a method may include a competent cell method using a microbial cell treated with calcium and an electroporation method. The gene may be introduced by infecting the microbial cell with a phage vector rather than the plasmid vector.

Further, a gene encoding the enzyme involved in the mevalonate pathway or the methylerythritol phosphate pathway that synthesizes dimethylallyl diphosphate that is the substrate of the isoprene synthase may also be introduced into the transformant of the present invention.

Examples of such an enzyme may include 1-deoxy-D-xylose-5-phosphate synthase that converts a pyruvate and D-glycelaldehyde-3-phosphate into 1-deoxy-D-xylose-5-phosphate, and isopentyl diphosphate isomerase that converts isopentenyl diphosphate into dimethylallyl diphosphate.

In embodiments of the transformant of the present invention, one or plural (e.g., 2, 3, 4 or 5) specific genomic regions (e.g., coding or non-coding regions) may be destroyed. Examples of such a genomic region include crt operon (coding for isoprenoid biosynthesis pathway such as polyprenyl synthetase, beta-carotene hydroxylase, phytoene synthase, phytoene dehydrogenase, lycopene cyclase and so on), and amp gene (e.g., ampC gene or ampH gene). For example, destruction of the crt operon may be advantageous as the production of isoprenoid compounds can be suppressed. The destruction of the amp gene may be advantageous as the ampicillin-resistance gene (a drug-resistance selectable marker) can be utilized.

The term "disrupted" for a gene means that a gene-coding region is modified so as to decrease or completely lose a function or expression of a protein encoded by the gene. The term "disrupted" for an operon means that a genomic region corresponding to the operon is modified so as to decrease or completely lose a function of the operon. When a function of an operon that can act as an enhancer (e.g., the aforementioned crt operon) is decreased or completely lost, an expression of a protein encoded by a gene operatively linked to the operon can be decreased or completely lost. On the other hand, when a function of an operon that can act as a suppressor is decreased or completely lost, an expression of a protein encoded by a gene operatively linked to the operon can be increased. Examples of the modification include, but not limited to, insertion, deletion and replacement.

The genomic region may be destroyed by introducing the aforementioned gene (e.g., mevalonate kinase gene) into the genomic region according to a gene targeting method previously known.

The mevalonate kinase may be extracted or purified from the transformant of the present invention, and isoprene may be produced by culturing the transformant that expresses the mevalonate kinase.

Methods for Producing Mevalonate-5-Phosphate, Isoprenoid Compound and Isoprene Polymer Embodiments of the present invention include methods of producing mevalonate-5-phosphate. In embodiments, the method of producing mevalonate-5-phosphate according to the present invention comprises forming mevalonate-5-phosphate from mevalonic acid using the transformant of the present invention. In embodiments of the method of producing mevalonate-5-phosphate according to the present invention, mevalonic acid that is a raw material for mevalonate-5-phosphate can be utilized efficiently by the transformant of the present invention. For example, mevalonic acid may be synthesized from the carbon source in the culture medium via a biosynthetic pathway such as a mevalonate pathway in the host. Alternatively, mevalonic acid may be added to the culture medium.

Embodiments of the present invention also include methods of producing an isoprenoid compound. In embodiments, the method of producing the isoprenoid compound according to the present invention comprises forming the isoprenoid compound using the transformant of the present invention.

The isoprenoid compound includes one or more isoprene units which have the molecular formula $(C_5H_8)_n$. The precursor of the isoprene unit may be isopentenyl pyrophosphate or dimethylallyl pyrophosphate. More than 30,000 kinds of isoprenoid compounds have been identified and new compounds have been identified. Isoprenoids are also known as terpenoids. The difference between terpenes and terpenoids is that terpenes are hydrocarbons, whereas terpenoids may contain additional functional groups. Terpenes are classified by the number of isoprene units in the molecule: hemiterpenes (C5), monoterpenes (C10), sesquiterpenes (C15), diterpenes (C20), sesterterpenes (C25), triterpenes (C30), sesquarterpenes (C35), tetraterpenes (C40), polyterpenes, norisoprenoids, for example. Examples of monoterpenes include pinene, nerol, citral, camphor, menthol, limonene, and linalool. Examples of sesquiterpenes include nerolidol and farnesol. Examples of diterpenes include phytol and vitamin A1. Squalene is an example of a triterpene, and carotene (provitamin A1) is a tetraterpene (Nature Chemical Biology 2, 674-681 (2006), Nature Chemical Biology 5, 283-291 (2009) Nature Reviews Microbiology 3, 937-947 (2005), Adv Biochem Eng Biotechmol (DOI: 10.1007/10_2014_288). Preferably, the isoprenoid compound is an isoprene monomer.

When the isoprenoid compound is an isoprene monomer, the transformant of the present invention may produce the isoprene monomer mainly as an outgas from the carbon source in the culture medium, and thus the isoprene monomer may be recovered by collecting gas generated by the transformant. Dimethylallyl diphosphate that is a raw material for the isoprene monomer may be synthesized from the carbon source in the culture medium via the mevalonate pathway or the methylerythritol phosphate pathway in the host. Alternatively, dimethylallyl diphosphate may be added to the medium.

The culture medium for culturing the transformant of the present invention preferably contains the carbon source to be converted into mevalonic acid or isoprene. The carbon source may include carbohydrates such as monosaccharides, disaccharides, oligosaccharides and polysaccharides; invert sugars obtained by hydrolyzing sucrose; glycerol; compounds having one carbon atom (hereinafter referred to as a C1 compound) such as methanol, formaldehyde, formate, carbon monoxide and carbon dioxide; oils such as corn oil, palm oil and soybean oil; acetate; animal fats; animal oils; fatty acids such as saturated fatty acids and unsaturated fatty acids; lipids; phospholipids; glycerolipids; glycerine fatty acid esters such as monoglyceride, diglyceride and triglyceride; polypeptides such as microbial proteins and plant proteins; renewable carbon sources such as hydrolyzed biomass carbon sources; yeast extracts, or combinations thereof. For a nitrogen source, inorganic ammonium salts such as ammonium sulfate, ammonium chloride and ammonium phosphate, organic nitrogen such as hydrolyzed soybeans, ammonia gas, ammonia water, and the like can be used. It is desirable to include required substances such as vitamin B1 and L-homoserine, or yeast extract and the like in an appropriate amount as an organic trace nutrient source. In addition thereto, potassium phosphate, magnesium sulfate, iron ion, manganese ion, and the like may be added in small amounts if necessary. The culture medium used in the present invention may be a natural medium or a synthesized medium as long as the culture medium contains a carbon source, a nitrogen source, inorganic ions, and optionally other organic trace ingredients.

Examples of the monosaccharides may include triose such as ketotriose (dihydroxyacetone) and aldotriose (glyceraldehyde); tetrose such as ketotetrose (erythrulose) and aldotetrose (erythrose, threose); pentose such as ketopentose (ribulose, xylulose), aldopentose (ribose, arabinose, xylose, lyxose) and deoxysaccharide (deoxyribose); hexose such as ketohexose (psychose, fructose, sorbose, tagatose), aldohexose (allose, altrose, glucose, mannose, gulose, idose, galactose, tallose), and deoxysaccharide (fucose, fucrose, rhamnose); and heptose such as sedoheptulose. C6 sugars such as fructose, mannose, galactose and glucose; and C5 sugars such as xylose and arabinose are preferable.

Examples of the disaccharides may include sucrose, lactose, maltose, trehalose, turanose, and cellobiose. Sucrose and lactose are preferable.

Examples of the oligosaccharides may include trisaccharides such as raffinose, melezitose and maltotriose; tetrasaccharides such as acarbose and stachyose; and other oligosaccharides such as fructooligosaccharide (FOS), galactooligosaccharide (GOS) and mannan-oligosaccharide (MOS).

Examples of the polysaccharides may include glycogen, starch (amylose, amylopectin), cellulose, dextrin, and glucan ($\beta$1,3-glucan). Starch and cellulose are preferable.

Examples of the microbial protein may include polypeptides obtainable from a yeast or bacterium.

Examples of the plant protein may include polypeptides obtainable from soybean, corn, canola, Jatropha, palm, peanut, sunflower, coconut, mustard, cotton seed, palm kernel oil, olive, safflower, sesame and linseed.

Examples of the lipid may include substances containing one or more saturated or unsaturated fatty acids of C4 or more.

The oil is preferably the lipid that contains one or more saturated or unsaturated fatty acids of C4 or more and is liquid at room temperature, and examples of the oil may include lipids obtainable from soybean, corn, canola, Jatropha, palm, peanut, sunflower, coconut, mustard, cotton seed, Palm kernel oil, olive, safflower, sesame, linseed, oily microbial cells, Chinese tallow tree, and a combination of two or more thereof.

Examples of the fatty acid may include compounds represented by a formula RCOOH ("R" represents a hydrocarbon group).

The unsaturated fatty acid is a compound having at least one double bond between two carbon atoms in "R", and examples of the unsaturated fatty acid may include oleic acid, vaccenic acid, linoleic acid, palmitelaidic acid and arachidonic acid.

The saturated fatty acid is a compound where the "R" is a saturated aliphatic group, and examples of the saturated fatty acid may include docosanoic acid, eicosanoic acid, octadecanoic acid, hexadecanoic acid, tetradecanoic acid, and dodecanoic acid.

Among them, those containing one or more C2 to C22 fatty acids are preferable as the fatty acid, and those containing C12 fatty acid, C14 fatty acid, C16 fatty acid, C18 fatty acid, C20 fatty acid and C22 fatty acid are more preferable.

The carbon source may include salts and derivatives of these fatty acids and salts of these derivatives. Examples of the salt may include lithium salts, potassium salts and sodium salts.

Examples of the carbon source may also include combinations of carbohydrate such as glucose with the lipid(s), the oil(s), the fats, the fatty acid(s) and glycerin fatty acid(s) ester(s).

Examples of the renewable carbon source may include hydrolyzed biomass carbon sources.

Examples of the biomass carbon source may include cellulose-based substrates such as waste materials of woods, papers and pulps, leafy plants, and fruit pulps; and partial plants such as stalks, grain particles, roots and tubers.

Examples of the plants to be used as the biomass carbon source may include corn, wheat, rye, sorghum, triticale, rice, millet, barley, cassava, legumes such as peas, potato, sweet potato, banana, sugar cane and tapioca.

When the renewable carbon source such as biomass is added to the culture medium, the carbon source is preferably pretreated. Examples of the pretreatment may include an enzymatic pretreatment, a chemical pretreatment, and a combination of the enzymatic pretreatment and the chemical pretreatment.

It is preferred that the renewable carbon source is entirely or partially hydrolyzed before being added to the culture medium (Kumar et al., Ind. Eng. Chem. Res., 48, 3713-3729, 2009).

Examples of the carbon source may also include the yeast extract and a combination of the yeast extract with the other carbon source such as glucose. The combination of the yeast extract with the C1 compound such as carbon dioxide and methanol is preferable.

In exemplary methods of culturing the transformant in connection with the present invention, it is preferable to culture the cell in a standard medium containing saline and nutrients.

The culture medium is not particularly limited, and examples of the culture medium may include ready-made general media that are commercially available such as Luria Bertani (LB) broth, Sabouraud dextrose (SD) broth, and yeast medium (YM) broth. The medium suitable for the cultivation of the specific host can be selected appropriately for the use.

It is desirable to include appropriate minerals, salts, supplemental elements, buffers, and ingredients known for those skilled in the art to be suitable for the cultivation and to facilitate the production of isoprene in addition to the appropriate carbon source in the cell medium.

It is preferable to add sugar, a metal salt, an antimicrobial substance, and the like to the culture medium in order to keep the expression of the objective protein in the transformant of the present invention.

A culture condition for the transformant of the present invention is not particularly limited as long as the objective protein can be expressed, and a standard cell culture condition can be used.

A culture temperature is preferably 20 to 37° C., a gas composition is preferably about 6 to 84% of $CO_2$ concentration, and a pH value is preferably about 5 to about 9.

The transformant is preferably cultured under an aerobic, oxygen-free, or anaerobic condition depending on a nature of the host.

Examples of methods of culturing the transformant include a method using a known fermentation method such as a batch cultivation method, a feeding cultivation method or a continuous cultivation method.

In the batch cultivation method, a medium composition is added at start of the fermentation, and the transformant is inoculated in the medium composition and cultured while pH and an oxygen concentration are controlled.

In the cultivation of the transformant by the batch cultivation method, the growth of the transformant starts from a mild induction phase, passes through a logarithmic growth phase and finally goes to a stationary phase in which a growth speed is reduced or stopped. Isoprene is produced by the transformant in the logarithmic growth phase and the stationary phase.

In the feeding cultivation method, in addition to the above batch method, the carbon source is gradually added according to the progress of a fermentation process. The feeding cultivation method is effective when an amount of the carbon source is to be restricted in the medium because metabolism of the transformant tends to be reduced due to catabolite suppression. The feed cultivation can be performed using a restricted amount or an excessive amount of the carbon source such as glucose.

In the continuous cultivation method, a certain amount of the medium is continuously supplied to a bioreactor at a constant rate while the same amount of the medium is removed. In the continuous cultivation method, the culture can be kept constantly at high concentration and the transformant in the culture medium is generally in the logarithmic growth phase.

The nutrition can be supplemented by entirely or partly exchanging the medium appropriately, and accumulation of metabolic byproducts that potentially have adverse effects on the growth of the transformant, and the accumulation of dead cells can be prevented.

A promoter possessed by the expression vector may include constitutive promoters and inducible promoters. When the expression vector has the inducible promoter such as a lac promoter, the expression of the objective protein may be induced by, for example, adding IPTG (isopropyl-β-thiogalactopyranoside) into the culture medium.

Examples of methods of evaluating an amount of isoprene produced by culturing the transformant of the present invention may include a method in which a gas phase is collected by a headspace method and this gas phase is analyzed by gas chromatography.

In detail, the isoprene monomer in a headspace which is obtained by culturing the transformant in a sealed vial with shaking the culture medium is analyzed by standard gas chromatography. Then, an area calculated by a curve measured by gas chromatography is converted into the amount of the isoprene monomer produced with the transformant using a standard curve.

Examples of the method of collecting the isoprene monomer obtained by culturing the transformant of the present invention may include gas stripping, fractional distillation, or dissociation of the isoprene monomer adsorbed to a solid phase by heat or vacuum, or extraction with a solvent.

In the gas stripping, isoprene gas is continuously removed from the outgas. Such removal of the isoprene gas can be performed by various methods. Examples of the removal may include adsorption to the solid phase, separation into a liquid phase, and a method in which the isoprene gas is directly condensed.

The isoprene monomer can be collected by a single step or multiple steps. When the isoprene monomer is collected by the single step, the isoprene monomer is converted into the liquid phase simultaneously with separating the isoprene monomer from the outgas. The isoprene monomer can also be directly condensed from the outgas to make the liquid phase. When the isoprene monomer is collected by the multiple stages, the isoprene monomer is separated from off-gas and subsequently converted into the liquid phase. For example, the isoprene monomer is adsorbed to the solid phase, and extracted from the solid phase with the solvent.

Exemplary methods of collecting the isoprene monomer may comprise further purifying the isoprene monomer. Examples of the purification may include separation from a liquid phase extract by distillation and various chromatographic methods.

Embodiments of the present invention include a method of producing an isoprene polymer. The method of producing the isoprene polymer according to the present invention may comprise the following (I) and (II):

(I) forming an isoprene monomer by an exemplary method of the present invention; and (II) polymerizing the isoprene monomer to form an isoprene polymer.

The step (I) can be performed in the same manner as in the exemplary methods of producing the isoprene monomer according to the present invention described above. The polymerization of the isoprene monomer in the step (II) can be performed by any method known in the art (e.g., synthesis methods such as addition polymerization in organic chemistry).

Method for Producing a Rubber Composition

In embodiments, the rubber composition of the present invention comprises a polymer derived from isoprene produced by an exemplary method for producing isoprene according to the present invention. The polymer derived from isoprene may be a homopolymer (i.e., isoprene polymer) or a heteropolymer comprising isoprene and one or more monomer units other than the isoprene (e.g., a copolymer such as a block copolymer). Preferably, the polymer derived from isoprene is a homopolymer (i.e., isoprene polymer) produced by an exemplary method for producing isoprene polymer according to the present invention. In embodiments, the rubber composition of the present invention may further comprise one or more polymers other than the above polymer, one or more rubber components, and/or other components. The rubber composition of the present invention can be manufactured using a polymer derived from isoprene. For example, the rubber composition of the present invention can be prepared by mixing a polymer derived from isoprene with one or more polymers other than the above polymer, one or more rubber components, and/or other components such as a reinforcing filler, a crosslinking agent, a vulcanization accelerator and an antioxidant.

Method for Producing a Tire

In embodiments, the tire of the present invention is manufactured using the rubber composition of the present invention. The rubber composition of the present invention may be applied to any portion of the tire without limitation, which may be selected as appropriate depending on the application thereof. For example, the rubber composition of the present invention may be used in a tread, a base tread, a sidewall, a side reinforcing rubber and a bead filler of a tire. The tire can be manufactured by a conventional method. For example, a carcass layer, a belt layer, a tread layer, which are composed of unvulcanized rubber, and other members used for the production of usual tires may be successively laminated on a tire molding drum, then the drum may be withdrawn to obtain a green tire. Thereafter, the green tire may be heated and vulcanized in accordance with an ordinary method, to thereby obtain a desired tire (e.g., a pneumatic tire).

EXAMPLES

In the following examples, and throughout this specification, all parts and percentages are by weight, and all temperatures are in degrees Celsius, unless expressly stated to be otherwise. Where the solids content of a dispersion or solution is reported, it expresses the weight of solids based on the total weight of the dispersion or solution, respectively. Where a molecular weight is specified, it is the molecular weight range ascribed to the product by the commercial supplier, which is identified. Generally this is believed to be weight average molecular weight.

Hereinafter, the present invention will be described in detail with reference to Examples, but the present invention is not limited to the following Examples.

Example 1

Preparation of Expression Plasmids for Mevalonate Kinase Derived from Various Microorganisms 1.1 Chemical Synthesis of the Gene Coding for Mevalonate Kinase Derived from *Methanocella paludicola*

A nucleotide sequence and an amino acid sequence of mevalonate kinase derived from *Methanocella paludicola* are known (Accession number of nucleotide sequence: NC_013665.1(1656560 . . . 1657459, complement, LOCUS TAG MCP_1639; accession number of amino acid sequence: YP_003356694 (GenPept), mevalonate kinase (MVK)). The amino acid sequence of a protein and the nucleotide sequence of a gene of MVK derived from *Methanocella paludicola* are shown in SEQ ID NO:1 and SEQ ID NO:2, respectively. An Mpdmvk gene was chemically synthesized, then cloned into pUC57 (supplied from GenScript), and the resulting plasmid was designated as pUC57-Mpdmvk.

1.2 Chemical Synthesis of the Gene Coding for Mevalonate Kinase Derived from *Corynebacterium variabile*

A nucleotide sequence and an amino acid sequence of mevalonate kinase derived from *Corynebacterium variabile* are known (Accession number of nucleotide sequence: NC_015859.1 (1024425 . . . 1025639, Locus tag CVAR_0902); accession number of amino acid sequence: YP_004759328.1 (GenPept)). The amino acid sequence of the MVK protein derived from *Corynebacterium variabile* and the nucleotide sequence of a gene of the protein are shown in SEQ ID NO:3 and SEQ ID NO:4, respectively. To efficiently express an MVK gene in *E. coli*, an MVK gene in which a codon usage in *E. coli* had been optimized was designed and this was designated as Cvamvk. A nucleotide sequence of Cvamvk is shown in SEQ ID NO:5. The Cvamvk gene was chemically synthesized, then cloned into pUC57 (supplied from GenScript), and the resulting plasmid was designated as pUC57-Cvamvk.

1.3 Chemical Synthesis of the Gene Coding for Mevalonate Kinase Derived from *Methanosaeta concilii*

A nucleotide sequence and an amino acid sequence of mevalonate kinase derived from *Methanosaeta concilii* are known (Accession number of nucleotide sequence: NC_015416.1 (2189051 . . . 2190004, complement, LOCUS TAG MCON_2559); Accession number of amino acid sequence: YP_004384801.1(GenPept)). The amino acid sequence of the MVK protein derived from *Methanosaeta concilii* and the nucleotide sequence of a gene of the protein are shown in SEQ ID NO:6 and SEQ ID NO:7, respectively. To efficiently express an MVK gene in *E. coli*, an MVK gene in which a codon usage in *E. coli* had been optimized was designed and this was designated as Mclmvk. A nucleotide sequence of Mclmvk is shown in SEQ ID NO:8. An Mclmvk gene was chemically synthesized, then cloned into pUC57 (supplied from GenScript), and the resulting plasmid was designated as pUC57-Mclmvk.

1.4 Chemical Synthesis of the Gene Coding for Mevalonate Kinase Derived from *Nitrosopumilus maritimus*

A nucleotide sequence and an amino acid sequence of mevalonate kinase derived from *Nitrosopumilus maritimus* are known (Accession number of nucleotide sequence: NC_010085.1 (278371 . . . 279312, complement, LOCUS TAG Nmar_0315); accession number of amino acid sequence: YP_001581649.1 (GenPept)). The amino acid sequence of the MVK protein derived from *Nitrosopumilus maritimus* and the nucleotide sequence of a gene of the protein are shown in SEQ ID NO:9 and SEQ ID NO:10, respectively. To efficiently express an MVK gene in *E. coli*, an MVK gene in which a codon usage in *E. coli* had been optimized was designed and this was designated as Nmrmvk. A nucleotide sequence of Nmrmvk is shown in SEQ ID NO:11. An Nmrmvk gene was chemically synthesized, then cloned into pUC57 (supplied from GenScript), and the resulting plasmid was designated as pUC57-Nmrmvk.

1.5 Chemical Synthesis of the Gene Coding for Mevalonate Kinase Derived from *Methanosarcina mazei*

A nucleotide sequence and an amino acid sequence of mevalonate kinase derived from *Methanosarcina mazei* Go1 are known (Accession number of nucleotide sequence: NC_003901.1 (2101873 . . . 2102778, LOCUS TAG MM_1762); accession number of amino acid sequence: NP_633786.1)). The amino acid sequence of the MVK protein derived from *Methanosarcina mazei* and the nucleotide sequence of a gene of the protein are shown in SEQ ID NO:12 and SEQ ID NO:13, respectively. To efficiently express an MVK gene in *E. coli*, an MVK gene in which a codon usage in *E. coli* had been optimized was designed and this was designated as Mmamvk. A nucleotide sequence of Mmamvk is shown in SEQ ID NO:14. An Mmamvk gene was chemically synthesized, then cloned into pUC57 (supplied from GenScript), and the resulting plasmid was designated as pUC57-Mmamvk.

1.6 Chemical Synthesis of the Gene Coding for Isoprene Synthase Derived from *Pueraria montana* var. *lobata* (Kudzu)

A nucleotide sequence and an amino acid sequence of mevalonate kinase derived from *Pueraria montana* var. *lobata* are known (Accession: AAQ84170: *P. montana* var. *lobata* (kudzu) isoprene synthase (IspS)). The amino acid sequence of the IspS protein derived from *P. montana* and the nucleotide sequence of cDNA encoding the amino acid sequence are shown in SEQ ID NO:15 and SEQ ID NO:16, respectively. To efficiently express an IspS gene in *E. coli*, an IspS gene in which the codon usage in *E. coli* had been optimized and further a chloroplast localization signal had been cleaved was designed, and this was designated as IspSK. A nucleotide sequence of IspSK is shown in SEQ ID NO:17. An IspSK gene was chemically synthesized, then cloned into pUC57 (supplied from GenScript), and the resulting plasmid was designated as pUC57-IspSK.

1.7 Construction of Expression Plasmid pSTV28-Ptac-Ttrp

An expression plasmid, pSTV28-Ptac-Ttrp was constructed for expressing IspS derived from a plant in *E. coli*. First, a DNA fragment (Ptac-Ttrp) containing a tac promoter (synonym: Ptac) region (deBoer, et al., (1983) Proc. Natl. Acad. Sci. U.S.A., 80, 21-25) and a terminator (synonym: Ttrp) region of a tryptophan operon derived from *E. coli* (Wu, et al., Proc. Natl. Acad. Sci. U.S.A., 75, 5442-5446, 1978) and having a KpnI site at 5' terminus and a BamHI site at 3' terminus was chemically synthesized (a nucleotide sequence of Ptac-Ttrp is shown in SEQ ID NO:18). The resulting DNA fragment of Ptac-Ttrp was digested with KpnI and BamHI and ligated to pSTV28 (supplied from TAKARA BIO Inc.) also digested with KpnI and BamHI by a ligation reaction with DNA ligase. The resulting plasmid was designated as pSTV28-Ptac-Ttrp (its nucleotide sequence is shown in SEQ ID NO:19). This plasmid can amplify the expression of a gene by cloning the gene to be expressed downstream of Ptac.

1.8 Construction of Plasmid for Expressing Isoprene Synthase Derived from *Pueraria montana* var. *lobata* (Kudzu) and MVK Gene Derived from Each Microorganism A plasmid for expressing the IspSK gene and the Mpdmvk gene, the Cvamvk gene, the Mclmvk gene, the Nmrmvk gene, Mmamvk gene or an EGR12 gene encoding mevalonate kinase derived from Saccharomyces cerevisiae (accession number of nucleotide sequence: NC_001145.3 (684467 . . . 685798, LOCUS TAG YMR208W, accession number of amino acid sequence: NP_013935.1)) in *E. coli* was constructed by the following procedures. PCR with pUC57-IspSK as a template was carried out using synthesized oligonucleotides consisting of nucleotide sequences of SEQ ID NO:20 and SEQ ID NO:21 as primers and using Prime Star polymerase (supplied from TAKARA BIO Inc.). A reaction solution was prepared according to a composition attached to a kit, and DNA was amplified through 40 cycles of reactions at 98° C. for 10 seconds, 54° C. for 20 seconds and 68° C. for 120 seconds. As a result, a PCR product containing the IspSK gene was obtained. Likewise, pSTV28-Ptac-Ttrp was amplified by PCR using synthesized oligonucleotides consisting of nucleotide sequences of SEQ ID NO:22 and SEQ ID NO:23 and using Prime Star polymerase (supplied from TAKARA BIO Inc.). A reaction solution was prepared according to the composition attached to the kit, and DNA was amplified through 40 cycles of reactions at 98° C. for 10 seconds, 54° C. for 20 seconds and 68° C. for 210 seconds. As a result, a PCR product containing pSTV28-Ptac-Ttrp was obtained. Subsequently, the purified IspSK gene fragment was ligated to the PCR product of pSTV28-Ptac-Ttrp using In-Fusion HD Cloning Kit (supplied from Clontech). The obtained plasmid for expressing the IspSK gene was designated as pSTV28-Ptac-IspSK. Subsequently, PCR with pUC57-Mpdmvk, pUC57-Cvamvk, pUC57-Mclmvk, pUC57-Nmrmvk, or pUC57-Mmamvk as the template was carried out using synthesized oligonucleotides consisting of nucleotide sequences of SEQ ID NO:24 and SEQ ID NO:25, synthesized oligonucleotides consisting of nucleotide sequences of SEQ ID NO:26 and SEQ ID NO:27, synthesized oligonucleotides consisting of nucleotide sequences of SEQ ID NO:28 and SEQ ID NO:29, synthesized oligonucleotides consisting of nucleotide sequences of SEQ ID NO:30 and SEQ ID NO:31, or synthesized oligonucleotides consisting of nucleotide sequences of SEQ ID NO:32 and SEQ ID NO:33, respectively, as the primers, and using Prime Star polymerase (supplied from TAKARA BIO Inc.). A reaction solution was prepared according to the composition attached to the kit, and DNA was amplified through 30 cycles of the reactions at 98° C. for 10 seconds, 55° C. for 5 seconds and 72° C. for one minute per kb. The ERG12 gene encoding mevalonate kinase was amplified by PCR with genomic DNA of *Saccharomyces cerevisiae* as the template using synthesized oligonucleotides consisting of nucleotide sequences of SEQ ID NO:34 and SEQ ID NO:35 as the primers and using KOD plus polymerase (supplied from TOYOBO Co., Ltd.). A reaction solution was prepared according to the composition attached to the kit, and DNA was amplified through 30 cycles of the reactions at 94° C. for 15 seconds, 45° C. for 30 seconds and 68° C. for one minute per kb. As a result, a PCR product containing the Mpdmvk gene, the Cvamvk gene, the Mclmvk gene, the Nmrmvk gene, the Mmamvk gene or the ERG12 gene was obtained. Likewise, pSTV28-Ptac-IspSK was amplified by PCR using synthesized oligonucleotides consisting of nucleotide sequences of SEQ ID NO:36 and SEQ ID NO:37 as the primers and using Prime Star polymerase (supplied from TAKARA BIO Inc.). A reaction solution was prepared according to the composition attached to the kit, and DNA was amplified through 30 cycles of the reactions at 98° C. for 10 seconds, 55° C. for 5 seconds and 72° C. for one minute per kb. As a result, a PCR product containing pSTV28-Ptac-IspSK was obtained. Subsequently, the purified Mpdmvk gene, Cvamvk gene, Mclmvk gene, Nmrmvk gene, Mmamvk gene or ERG12 gene fragment was ligated to the PCR product of pSTV28-Ptac-IspSK using In-Fusion HD Cloning Kit (supplied from Clontech). The obtained plasmid for expressing the IspSK gene and the Mpdmvk gene was designated as pSTV28-Ptac-ispSK-Mpdmvk. The plasmid for expressing the IspSK gene and the Cvamvk gene was designated as pSTV28-Ptac-ispSK-Cvamvk. The plasmid for expressing the IspSK gene and the Mclmvk gene was designated as pSTV28-Ptac-ispSK-Mclmvk. The plasmid for expressing the IspSK gene and the Nmrmvk gene was designated as pSTV28-Ptac-ispSK-Nmrmvk. The plasmid for expressing the IspSK gene and the Mmamvk gene was designated as pSTV28-Ptac-ispSK-Mmamvk. The plasmid for expressing the IspSK gene and the ERG12mvk gene was designated as pSTV28-Ptac-ispSK-ERG12mvk.

Example 2

Introduction of Mevalonate Kinase Candidate Gene Derived from Microorganism and Confirmation of its Function as Mevalonate Kinase in *E. coli* MG1655 Strain (ATCC700926) in which Mevalonic Acid Pathway was Introduced Concerning the expression plasmids for the genes encoding mevalonate kinase, which were constructed in Example 1, functions of the genes that were chosen were based on presumption by homology search. Thus, it was experimentally confirmed that the function of the gene was mevalonate kinase. Specifically, a microbial strain in which isoprene could be produced only when mevalonate kinase was present was constructed, the expression plasmid for the gene encoding mevalonate kinase, which had been constructed in Example 1, was introduced into this microbial strain, and the production of isoprene was confirmed. Details are shown below.

2.1 Construction of Mevalonate Kinase Gene Deficient Strain from Strain in which Genes Downstream of Mevalonic Acid Pathway were Fixed on Chromosome An ERG12 gene deficient strain was produced from MG1655 Ptac-KKDyI strain (see, Example 7-5) of WO2013/179722) in which an artificial operon consisting of an ERG12 gene encoding mevalonate kinase, an ERG8 gene encoding phosphomevalonate kinase, an ERG19 gene encoding diphosphomevalonate decarboxylase and an IDI1 gene encoding isopentenyl diphosphate delta isomerase which are derived from S. cerevisiae had been fixed on a chromosome.

A plasmid pKD46 having a temperature sensitive replication capacity was introduced into MG1655 Ptac-KKDyI strain by an electroporation method. The plasmid pKD46 (Proc. Natl. Acad. Sci. USA, 2000, vol. 97, No. 12, pp. 6640-6645) contains a DNA fragment of total 2154 nucleotides of a k phage including a genes in a λ red system controlled by an alabinose-inducible ParaB promoter (GenBank/EMBL accession number J02459, 31088th to 33241st nucleotides). Competent cells of MG1655 Ptac-KKDyI strain were prepared, then pKD46 was introduced thereto by the electroporation method, and the cells were evenly applied onto an LB plate containing 100 mg/L of ampicillin and cultured at 37° C. for 18 hours. Subsequently, a transformant exhibiting ampicillin resistance was acquired from the resulting plate. The strain in which pKD46 had been introduced into E. coli MG1655 Ptac-KDDyI strain was designated as MG1655 Ptac-KDDyI/pKD46 strain. PCR with an attL-tetR-attR-Ptac gene fragment (SEQ ID NO:38) as the template was carried out using synthesized oligonucleotides consisting of SEQ ID NO:39 and SEQ ID NO:40 as the primers and using Prime Star polymerase (supplied from TAKARA BIO Inc.). A reaction solution was prepared according to the composition attached to the kit, and DNA was amplified through 30 cycles of reactions at 98° C. for 10 seconds, 55° C. for 5 seconds and 72° C. for one minute per kb. As a result, an MVK gene deficient fragment containing attL-tetR-attR-Ptac was obtained. Competent cells of MG1655 Ptac-KDDyI/pKD46 were prepared, and then the purified MVK gene deficient fragment containing attL-tetR-attR-Ptac was introduced thereto by the electroporation method. After the electroporation, a colony that had acquired tetracycline resistance was obtained. PCR was carried out using synthesized oligonucleotides consisting of SEQ ID NO:41 and SEQ ID NO:42 as the primers to confirm that the ERG12 gene on the chromosome was deficient. The obtained mutant was designated as E. coli MG1655 Ptac-KDyI.

2.2 Introduction of Mevalonate Kinase Derived from Microorganism into E. coli MG1655 Ptac-KDyI Strain Competent cells of E. coli MG1655 Ptac-KDyI strain were prepared, and then pSTV28-Ptac-ispSK-Mpdmvk, pSTV28-Ptac-ispSK-Cvamvk, pSTV28-Ptac-ispSK-Mclmvk, pSTV28-Ptac-ispSK-Nmrmvk, pSTV28-Ptac-ispSK-ERG12mvk, pSTV28-Ptac-Mmamvk, or pSTV28-Ptac-Ttrp was introduced thereto by the electroporation method. The cells were evenly applied onto an LB plate containing 60 mg/L of chloramphenicol and cultured at 37° C. for 18 hours. Subsequently, transformants exhibiting chloramphenicol resistance were obtained from the resulting plates. A strain in which pSTV28-Ptac-ispSK-Mpdmvk had been introduced into E. coli MG1655 Ptac-KDyI strain was designated as E. coli MG1655 Ptac-KDyI/pSTV28-Ptac-ispSK-Mpdmvk strain. A strain in which pSTV28-Ptac-ispSK-Cvamvk had been introduced into E. coli MG1655 Ptac-KDyI strain was designated as E. coli MG1655 Ptac-KDyI/pSTV28-Ptac-ispSK-Cvamvk strain. A strain in which pSTV28-Ptac-ispSK-Mclmvk had been introduced into E. coli MG1655 Ptac-KDyI strain was designated as E. coli MG1655 Ptac-KDyI/pSTV28-Ptac-ispSK-Mclmvk strain. A strain in which pSTV28-Ptac-ispSK-Nmrmvk had been introduced into E. coli MG1655 Ptac-KDyI strain was designated as E. coli MG1655 Ptac-KDyI/pSTV28-Ptac-ispSK-Nmrmvk strain. A strain in which pSTV28-Ptac-ispSK-Mmamvk had been introduced into E. coli MG1655 Ptac-KDyI strain was designated as E. coli MG1655 Ptac-KDyI/pSTV28-Ptac-ispSK-Mmamvk strain. A strain in which pSTV28-Ptac-ispSK-ERG12mvk had been introduced into E. coli MG1655 Ptac-KDyI strain was designated as E. coli MG1655 Ptac-KDyI/pSTV28-Ptac-ispSK-ERG12mvk strain.

2.3 Chemical Synthesis of mvaE Gene Derived from Enterococcus faecalis

A nucleotide sequence and an amino acid sequence of mvaE encoding acetyl-CoA acetyltransferase and hydroxymethylglutaryl-CoA reductase and derived from Enterococcus faecalis are known (accession number of nucleotide sequence: AF290092.1 (1479 . . . 3890); accession number of amino acid sequence: AAG02439) (J. Bacteriol., 182 (15), 4319-4327 (2000)). The amino acid sequence of the mvaE protein derived from Enterococcus faecalis and the nucleotide sequence of the gene encoding it are shown in SEQ ID NO:43 and SEQ ID NO:44, respectively. To efficiently express the mvaE gene, an mvaE gene in which the codon usage in E. coli had been optimized was designed and this was designated as EFmvaE. This nucleotide sequence is shown in SEQ ID NO:45. The mvaE gene was chemically synthesized, then cloned into pUC57 (supplied from GenScript), and the resulting plasmid was designated as pUC57-EFmvaE.

2.4 Chemical Synthesis of mvaS Gene Derived from Enterococcus faecalis

A nucleotide sequence and an amino acid sequence of mvaS encoding hydroxymethylglutaryl-CoA synthase derived from Enterococcus faecalis are known (accession number of nucleotide sequence: AF290092.1 complement (142 . . . 1293); accession number of amino acid sequence: AAG02438) (J. Bacteriol., 182 (15), 4319-4327 (2000)). The amino acid sequence of the mvaS protein derived from Enterococcus faecalis and the nucleotide sequence of the gene encoding it are shown in SEQ ID NO:46 and SEQ ID NO:47, respectively. To efficiently express the mvaS gene, an mvaS gene in which the codon usage in E. coli had been optimized was designed and this was designated as EFmvaS. This nucleotide sequence is shown in SEQ ID NO:48. The mvaS gene was chemically synthesized, then cloned into pUC57 (supplied from GenScript), and the resulting plasmid was designated as pUC57-EFmvaS.

2.5 Construction of Arabinose-inducible mvaES Expression Vector

An arabinose-inducible expression vector for mevalonate pathway upstream genes was constructed by the following procedure. A PCR fragment containing Para consisting of araC and araBAD promoter sequences derived from *E. coli* was obtained by PCR with the plasmid pKD46 as the template using synthesized oligonucleotides represented by SEQ ID NO:49 and SEQ ID NO:50 as the primers. A PCR fragment containing the EFmvaE gene was obtained by PCR with the plasmid pUC57-EFmvaE as the template using synthesized oligonucleotides represented by SEQ ID NO:51 and SEQ ID NO:52 as the primers. A PCR fragment containing the EFmvaS gene was obtained by PCR with the plasmid pUC57-EFmvaS as the template using synthesized oligonucleotides represented by SEQ ID NO:53 and SEQ ID NO:54 as the primers. A PCR fragment containing a Ttrp sequence was obtained by PCR with the plasmid pSTV-Ptac-Ttrp as the template (source of the plasmid) using synthesized oligonucleotides represented by SEQ ID NO:55 and SEQ ID NO:56 as the primers. Prime Star polymerase (TAKARA BIO Inc.) was used for PCR for obtaining these four PCR fragments. Reaction solutions were prepared according to the composition attached to the kit, and DNA was amplified through 30 cycles of the reactions at 98° C. for 10 seconds, 55° C. for 5 seconds and 72° C. for one minute per kb. PCR with the purified PCR product containing Para and the PCR product containing the EFmvaE gene as the template was carried out using synthesized oligonucleotides represented by SEQ ID NO:49 and SEQ ID NO:52 as the primers. PCR with the purified PCR product containing the EFmvaS gene and the PCR product containing Ttrp as the template was also carried out using synthesized oligonucleotides represented by SEQ ID NO:53 and SEQ ID NO:56 as the primers. As a result, a PCR product containing Para and the EFmvaE gene and a PCR product containing the EFmvaS gene and Ttrp were obtained. A plasmid pMW219 (supplied from Nippon Gene Co., Ltd.) was digested with SmaI according to a standard method. Then, pMW219 after being digested with SmaI was ligated to the PCR product containing Para and the EFmvaE gene and the PCR product containing the EFmvaS gene and Ttrp using In-Fusion HD Cloning Kit (supplied from Clontech). The obtained plasmid was designated as pMW-Para-mvaES-Ttrp.

2.6 Construction of Strain in which Arabinose-inducible Expression Vector for mvaES is Introduced into *E. coli* MG1655 KDyI Strain Introduced with Mevalonate Kinase Derived from Microorganism Competent cells of *E. coli* MG1655 Ptac-KDyI/pSTV28-Ptac-ispSK-Mpdmvk strain, *E. coli* MG1655 Ptac-KDyI/pSTV28-Ptac-ispSK-Cvamvk strain, *E. coli* MG1655 Ptac-KDyI/pSTV28-Ptac-ispSK-Mclmvk strain, *E. coli* MG1655 Ptac-KDyI/pSTV28-Ptac-ispSK-Nmrmvk strain, *E. coli* MG1655 Ptac-KDyI/pSTV28-Ptac-ispSK-Mmamvk strain, or *E. coli* MG1655 Ptac-KDyI/pSTV28-Ptac-ispSK-ERG12mvk strain were prepared, then pMW-Para-mvaES-Ttrp was introduced thereto by the electroporation method. The cells were evenly applied onto an LB plate containing 60 mg/L of chloramphenicol and 50 mg/L of kanamycin and cultured at 37° C. for 18 hours. Subsequently, transformants exhibiting chloramphenicol resistance and kanamycin resistance were obtained from the resulting plates. A strain in which pMW-Para-mvaES-Ttrp had been introduced into *E. coli* MG1655 Ptac-KDyI/pSTV28-Ptac-ispSK-Mpdmvk strain was designated as *E. coli* MG1655 Ptac-KDyI/pMW-Para-mvaES-Ttrp/pSTV28-Ptac-ispSK-Mpdmvk strain. A strain in which pMW-Para-mvaES-Ttrp had been introduced into *E. coli* MG1655 Ptac-KDyI/pSTV28-Ptac-ispSK-Cvamvk was designated as *E. coli* MG1655 Ptac-KDyI/pMW-Para-mvaES-Ttrp/pSTV28-Ptac-ispSK-Cvamvk strain. A strain in which pMW-Para-mvaES-Ttrp had been introduced into *E. coli* MG1655 Ptac-KDyI/pSTV28-Ptac-ispSK-Mclmvk was designated as *E. coli* MG1655 Ptac-KDyI/pMW-Para-mvaES-Ttrp/pSTV28-Ptac-ispSK-Mclmvk strain. A strain in which pMW-Para-mvaES-Ttrp had been introduced into *E. coli* MG1655 Ptac-KDyI/pSTV28-Ptac-ispSK-Nmrmvk was designated as *E. coli* MG1655 Ptac-KDyI/pMW-Para-mvaES-Ttrp/pSTV28-Ptac-ispSK-Nmrmvk strain. A strain in which pMW-Para-mvaES-Ttrp had been introduced into *E. coli* MG1655 Ptac-KDyI/pSTV28-Ptac-ispSK-Mmamvk was designated as *E. coli* MG1655 Ptac-KDyI/pMW-Para-mvaES-Ttrp/pSTV28-Ptac-ispSK-Mmamvk strain. A strain in which pMW-Para-mvaES-Ttrp had been introduced into *E. coli* MG1655 Ptac-KDyI/pSTV28-Ptac-ispSK-ERG12mvk was designated as *E. coli* MG1655 Ptac-KDyI/pMW-Para-mvaES-Ttrp/pSTV28-Ptac-ispSK-ERG12mvk strain.

2.7 Effect of Introducing Mevalonate Kinase Derived from Microorganism in *E. coli* MG1655 Strain having Ability to Produce Isoprene Cells of *E. coli* MG1655 Ptac-KDyI/pMW-Para-mvaES-Ttrp/pSTV28-Ptac-ispSK-Mpdmvk strain, *E. coli* MG1655 Ptac-KDyI/pMW-Para-mvaES-Ttrp/pSTV28-Ptac-ispSK-Cvamvk strain, *E. coli* MG1655 Ptac-KDyI/pMW-Para-mvaES-Ttrp/pSTV28-Ptac-ispSK-Mclmvk strain, *E. coli* MG1655 Ptac-KDyI/pMW-Para-mvaES-Ttrp/pSTV28-Ptac-ispSK-Nmrmvk strain, *E. coli* MG1655 Ptac-KDyI/pMW-Para-mvaES-Ttrp/pSTV28-Ptac-ispSK-Mmamvk strain, or *E. coli* MG1655 Ptac-KDyI/pMW-Para-mvaES-Ttrp/pSTV28-Ptac-ispSK-ERG12mvk strain were evenly applied onto an LB plate containing 60 mg/L of chloramphenicol and 50 mg/L of kanamycin and cultured at 37° C. for 18 hours. One loopful of microbial cells obtained from the resulting plate was inoculated to 1 mL of M9 glucose+arabinose medium in a headspace vial, which was then sealed with a cap with butyl rubber septum (CRIMPS Cat #B0104240 supplied from Perkin Elmer) for the headspace vial. Subsequently, the cells were cultured at 30° C. for 24 hours on a reciprocal shaking culture apparatus (120 rpm). A composition of the M9 glucose+arabinose medium is as shown in

TABLE 1

| Composition of M9 glucose + arabinose medium | |
|---|---|
| Glucose | 1.0 g/L |
| Arabinose | 3.0 g/L |
| $Na_2HPO_4$ | 6.0 g/L |
| $KH_2PO_4$ | 3.0 g/L |
| NaCl | 0.5 g/L |
| $NH_4Cl$ | 1.0 g/L |
| 1M $MgSO_4$ (autoclaved) | 1.0 mL |
| 1M $CaCl_2$ (autoclaved) | 0.1 mL |

Further, chloramphenicol and kanamycin were added at final concentrations of 60 mg/L and 50 mg/L, respectively. A total volume was adjusted to 1 L, which was then sterilized by filtration.

After the culture, a concentration of isoprene in the headspace in the vial was measured by gas chromatography. Also, an OD value was measured at 600 nm using a spectrophotometer (HITACHI U-2900). The concentration of isoprene and the OD value when the culture of each microbial strain was terminated are described in Table 2. Analysis conditions of the gas chromatography are described below.

Headspace sampler (Turbo Matrix 40, supplied from Perkin Elmer)

Heat retention temperature for vial: 40° C.
Heat retention time for vial: 30 minutes
Pressurization time: 3.0 minutes
Injection time: 0.02 minute
Needle temperature: 70° C.
Transfer temperature: 80° C.
Carrier gas pressure (highly purified helium): 124 kPa
Gas chromatography (GC-2010 Plus AF supplied from Shimadzu Corporation)
Column (Rxi (registered trademark)-1 ms: length 30 m, inner diameter: 0.53 mm, liquid phase membrane thickness: 1.5 µm, Cat #13370)
Column temperature: 37° C.
Pressure: 24.8 kPa
Column flow amount: 5 mL/minute
Inflow method: Split 1:0 (actual measurement 1:18)
Transfer flow amount: 90 mL
GC injection amount: 1.8 mL (transfer flow amount× injection time)
Sample amount injected into column: 0.1 mL
Inlet temperature: 250° C.
Detector FID (hydrogen 40 mL/minute, air 400 mL/minute, makeup gas helium 30 mL/minute)
Detector temperature: 250° C.

Preparation of Isoprene Standard Samples

A reagent isoprene (specific gravity: 0.681) was diluted with cooled methanol to 10, 100, 1,000, 10,000 and 100,000 times to prepare standard solutions for addition. Subsequently, each 1 µL of each standard solution for the addition was added to a headspace vial in which 1 mL of water had been already added, and used as a standard sample.

TABLE 2

OD value and amount of produced isoprene (mg/L) when culture of each microbial strain was terminated

| Strains | OD$_{600}$ | Isoprene (mg/L) |
|---|---|---|
| (1) | 3.29 ± 0.01 | 0.53 ± 0.0 |
| (2) | 3.63 ± 0.01 | 38.0 ± 1.2 |
| (3) | 2.56 ± 0.60 | 437.8 ± 65.3 |
| (4) | 2.08 ± 0.10 | 327.7 ± 100.4 |
| (5) | 2.83 ± 0.21 | 369.0 ± 58.3 |
| (6) | 3.05 ± 0.05 | 453.3 ± 9.0 |
| (7) | 3.08 ± 0.01 | 52.4 ± 1.7 |

The strains as shown below were used:
(1) MG1655::Ptac-KdyI/pWM-Para-mvaES-Ttrp/pSTV-Ptac-ispSK;
(2) MG1655::Ptac-KdyI/pWM-Para-mvaES-Ttrp/pSTV-Ptac-ispSK-ERG12mvk;
(3) MG1655::Ptac-KdyI/pWM-Para-mvaES-Ttrp/pSTV-Ptac-ispSK-Cvamvk;
(4) MG1655::Ptac-KdyI/pWM-Para-mvaES-Ttrp/pSTV-Ptac-ispSK-Mclmvk;
(5) MG1655::Ptac-KdyI/pWM-Para-mvaES-Ttrp/pSTV-Ptac-ispSK-Nmrmyk;
(6) MG1655::Ptac-KdyI/pWM-Para-mvaES-Ttrp/pSTV-Ptac-ispSK-Mmamvk; and
(7) MG1655::Ptac-KdyI/pWM-Para-mvaES-Ttrp/pSTV-Ptac-ispSK-Mpdmvk.

*E. coli* MG1655 KdyI/pMW-Para-mvaES-Ttrp/pSTV-Ptac-ispSK strain having no gene encoding mevalonate kinase scarcely produced isoprene. On the other hand, the protein encoded by the ERG12 gene from the yeast and the protein encoded by the mvk gene from *M. mazei* are known to have a mevalonate kinase activity. *E. coli* MG1655 KdyI/pMW-Para-mvaES-Ttrp/pSTV-Ptac-ispSK-ERG12 strain and *E. coli* MG1655 KdyI/pMW-Para-mvaES-Ttrp/pSTV-Ptac-ispSK-Mmamvk strain in which these genes had been introduced accumulated isoprene in an amount of 38.0 mg/L and 453 mg/L, respectively. This confirmed that the reason why *E. coli* MG1655 KdyI/pMW-Para-mvaES-Ttrp/pSTV-Ptac-ispSK strain having no gene encoding mevalonate kinase scarcely produced isoprene is that the strain does not have the gene encoding mevalonate kinase. Also, the results shown in Table 2 indicate that it could be experimentally confirmed that the genes which were chosen as the genes encoding mevalonate kinase from genomic sequence information for *Methanocella paludicola, Corynebacterium variabile, Methanosaeta concilii,* and *Nitrosopumilus maritimus* actually encoded mevalonate kinase. That is, *E. coli* MG1655 KdyI/pMW-Para-mvaES-Ttrp/pSTV-Ptac-ispSK-Mpdmvk, *E. coli* MG1655 KdyI/pMW-Para-mvaES-Ttrp/pSTV-Ptac-ispSK-Cvamvk, *E. coli* MG1655 KdyI/pMW-Para-mvaES-Ttrp/pSTV-Ptac-ispSK-Mclmvk, and *E. coli* MG1655 KdyI/pMW-Para-mvaES-Ttrp/pSTV-Ptac-ispSK-Nmrmvk each produced isoprene in an amount of 52.4 mg/L, 437.8 mg/L, 327.7 mg/L and 369.0 mg/L. These amounts of produced isoprene were higher than the amounts in the case of introducing the ERG12 gene derived from the yeast. In particular, the amounts of isoprene produced by the strains introduced with each of the Cvamvk, Mclmvk and Nmrmvk genes are almost equivalent to the amount in the case of introducing the mvk gene derived from *M. mazei*.

Example 3

Production of Isoprene Monomer Using *Pantoea ananatis*

3.1 Construction of MVK Expression Plasmid

MVK expression plasmids (pMW-Ptac-mvk-Ttrp) were constructed.

PCR was performed with Prime Star polymerase (supplied from Takara Bio Inc.) using synthetic oligonucleotides consisting of the nucleotide sequences of cva_mvk_N (SEQ ID NO:57) and cva_mvk_C (SEQ ID NO:58) as the primers with pUC57-Cvamvk as the template, using synthetic oligonucleotides consisting of the nucleotide sequences of Mcl_mvk N (SEQ ID NO:59) and Mcl_mvk_C (SEQ ID NO:60) as the primers with pUC57-Mclmvk as the template, using synthetic oligonucleotides consisting of the nucleotide sequences of Nmr_mvk_N (SEQ ID NO:61) and Nmr_mvk_C (SEQ ID NO:62) as the primers with pUC57-Nmrmvk as the template, and using synthetic oligonucleotides consisting of the nucleotide sequences of MMVKf (SEQ ID NO:63) and MMVKr (SEQ ID NO:64) as the primers with pUC57-Mmamvk as the template. A reaction solution was prepared according to the composition attached to the kit, and the reaction at 98° C. for 10 seconds, 55° C. for 5 seconds and 72° C. for one minute per kb was performed in 30 cycles. As a result, PCR products containing a Cvamvk gene, an Mclmvk gene, an Nmrmvk gene, or an Mmamvk gene were obtained. Likewise, pMW219-Ptac-Ttrp (see WO2013/069634A1) was amplified by PCR performed with Prime Star polymerase (supplied from Takara Bio Inc.) using synthetic oligonucleotides consisting of the nucleotide sequences of PtTt219f (SEQ ID NO:65) and PtTt219r (SEQ ID NO:66) as the primers. A reaction solution was prepared according to the composition attached to the kit, and the reaction at 98° C. for 10 seconds, 55° C. for 5 seconds and 72° C. for one minute per kb was performed in 30 cycles. As a result, a PCR product containing pMW219-Ptac-Ttrp was obtained. Subsequently, the purified PCR product of the Cvamvk gene, Mclmvk gene, Nmrmvk gene or Mmamvk gene was ligated to the PCR product of pMW219-Ptac-Ttrp using In-Fusion HD Cloning Kit (supplied from Clontech). The resulting expression plasmids for the Cvamvk gene, Mclmvk gene, Nmrmvk gene and Mmamvk gene were designated as pMW-Ptac-Cvamvk-Ttrp, pMW-Ptac-Mclmvk-Ttrp, pMW-Ptac-Nmrmvk-Ttrp, and pMW-Ptac-Mmamvk-Ttrp, respectively.

3.2 Construction of pTrc-KKDyI-ispS(K)

First, an expression vector comprising a sequence in which mevalonate kinase, phosphomevalonate kinase, diphosphomevalonate dexarboxylase and isopentenyl diphosphate delta isomerase were aligned linearly was constructed by an In-fusion cloning method. A sequence of the mevalonate kinase and a sequence of the phosphomevalonate kinase were amplified by PCR using primers consisting of nucleotide sequences of SEQ ID NOS:67 to 70 with pUC-mvk-pmk (see, Example 7-2) of WO2013/179722A1) as a template. A sequence of the diphosphomevalonate dexarboxylase and a sequence of isopentenyl diphosphate delta isomerase were amplified by PCR using primers consisting of nucleotide sequences of SEQ ID NOS:67 to 70 with pTWV-dmd-yidi (see, Example 7-2) of WO2013/179722A1) as a template. Subsequently, these PCR products were cloned into pTrcHis2B vector by the In-fusion cloning method to construct an expression plasmid in which the four enzyme genes were aligned linearly. Prime Star HS DNA polymerase commercially available from Takara Bio Inc. was used as a PCR enzyme. The reaction at 98° C. for 2 minutes, (the reaction at 98° C. for 10 seconds, 52° C. for 5 seconds and 72° C. for one minute per kb)×30 cycles, and the reaction at 72° C. for 10 minutes were performed. The PCR fragments were inserted into pTrcHis2B vector digested with the restriction enzymes NcoI and PstI by the In-fusion cloning method to construct the expression vector. E. coli JM109 was transformed with the expression vector, a clone having an objective sequence length was selected, and subsequently the plasmid was extracted according to a standard method and sequence of the clone was confirmed. The constructed expression vector was designated as pTrc-KKDyI(α). A nucleotide sequence of pTrc-KKDyI(α) is shown in SEQ ID NO:71.

Next, the plasmid pTrc-KKDyI-ispS(K) in which IspS(K) is added to pTrc-KKDyI(α) (SEQ ID NO:71) was constructed by the following procedure.

pTrc-KKDyI(α) was digested with the restriction enzyme PstI (supplied from TAKARA BIO Inc.) to obtain pTrc-KKDyI(α)/PstI. PCR with pUC57-ispSK as the template was carried out using pTrcKKDyIkSS_6083-10-1 (SEQ ID NO:72) and pTrcKKDyIkSA_6083-10-2 (SEQ ID NO:73) as the primers and using Prime Star polymerase (supplied from TAKARA BIO Inc.). A reaction solution was prepared according to the composition attached to the kit, and the reaction at 98° C. for 10 seconds, 54° C. for 20 seconds and 68° C. for 120 seconds was carried out in 30 cycles. As a result, a PCR product containing the IspSK gene was obtained. Subsequently, the purified IspSK gene fragment was ligated to pTrc-KKDyI(α)/PstI using In-Fusion HD Cloning Kit (supplied from Clontech). The resulting plasmid was designated as pTrc-KKDyI-ispS(K) (SEQ ID NO:74).

3.3 Construction of the Integrative Conditionally Replicated Plasmids Carrying Genes of Upper and Lower Mevalonate Pathways To construct the integrative plasmids carrying genes of upper and lower mevalonate pathways the pAH162-λattL-TcR-λattR vector (Minaeva, N. I., et al., BMC Biotechnol., 2008; 8: 63) was used.

KpnI-SalI fragment of pMW-Para-mvaES-Ttrp was cloned into SphI-SalI recognition sites of pAH162-λattL-TcR-λattR. As a result, the pAH162-Para-mvaES plasmid carrying mvaES operon from E. faecalis under control of the E. coli Para promoter and repressor gene araC were constructed (FIG. 1).

Figure 2:
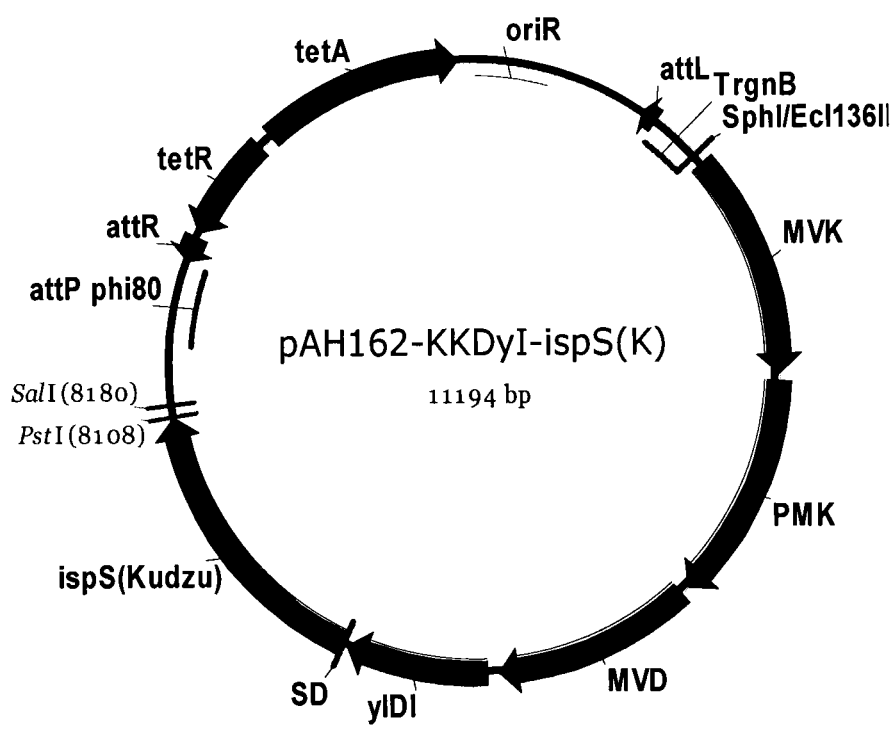
FIG. 2 is a schematic depiction of pAH162-KKDyI-ispS (K)

Ecl136II-SalI fragment of the pTrc-KKDyI-ispS(K) plasmid including coding parts of the mevalonate kinase, phosphomevalonate kinase, diphosphomevalonate decarboxylase and IPP isomerase genes from S. cerevisiae and ispS gene from Kudzu was sub-cloned into SphI-SalI sites of pAH162-λattL-TcR-λattR. The resulting plasmid was designated pAH162-KKDyI-ispS(K) (FIG. 2).

Figure 3:
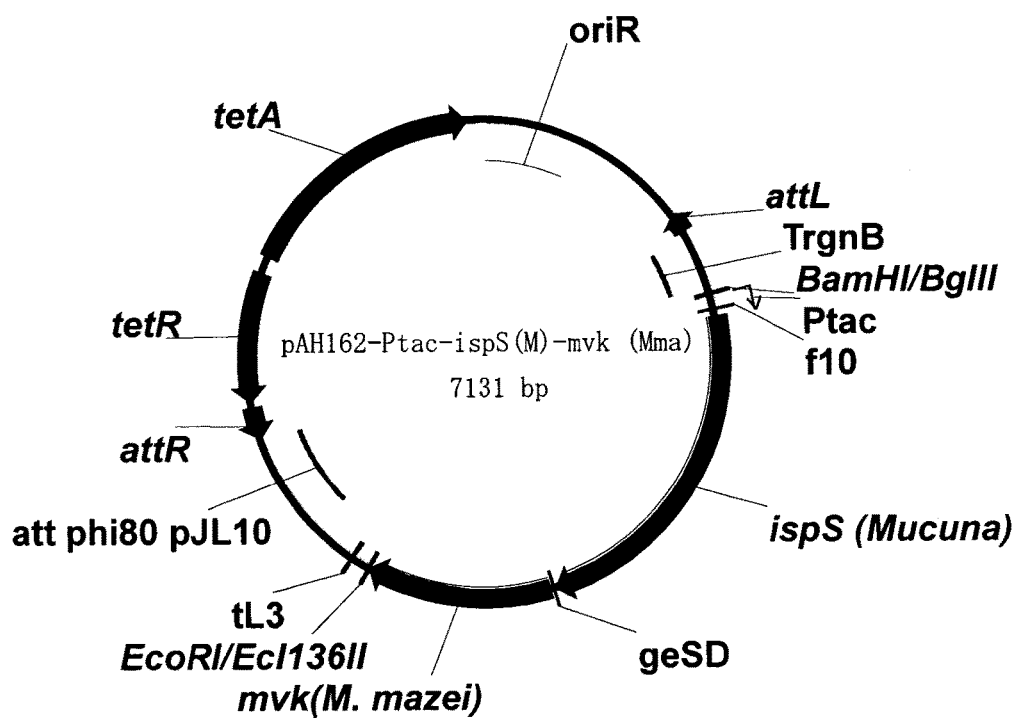
FIG. 3 is a schematic depiction of pAH162-Ptac-ispS(M)-mvk(Mma)

BglII-EcoRI fragment of the pSTV28-Ptac-ispS-Mmamvk containing the ispS (mucuna) and mvk (M. mazei) genes under control of Ptac has been sub-cloned into BamHI-Ecl136II recognition sites of the integrative vector pAH162-λattL-TcR-λattR. The obtained plasmid pAH162-Ptac-ispS(M)-mvk(Mma) is depicted in FIG. 3.

Figure 4:
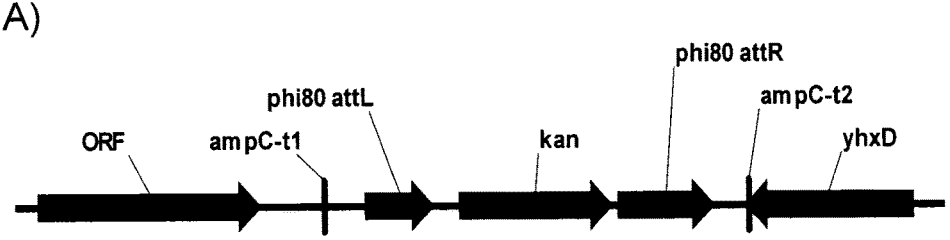
FIG. 4 is a schematic depiction of construction of the ΔampC::KKDyI-ispS(K) chromosome modification: A) λRed-dependent substitution of the ampC gene by attLphi80-kan-attRphi80 PCR-generated DNA fragment; B) phi80Int-dependent integration of the pAH162-KKDyI-ispS (K) plasmid; and C) phi80Int/Xis-dependent elimination of vector part of pAH162-KKDyI-ispS(K)
Figure 4:
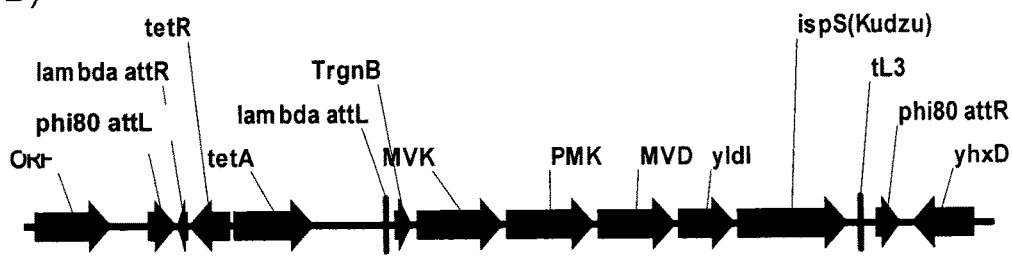
Figure 4:
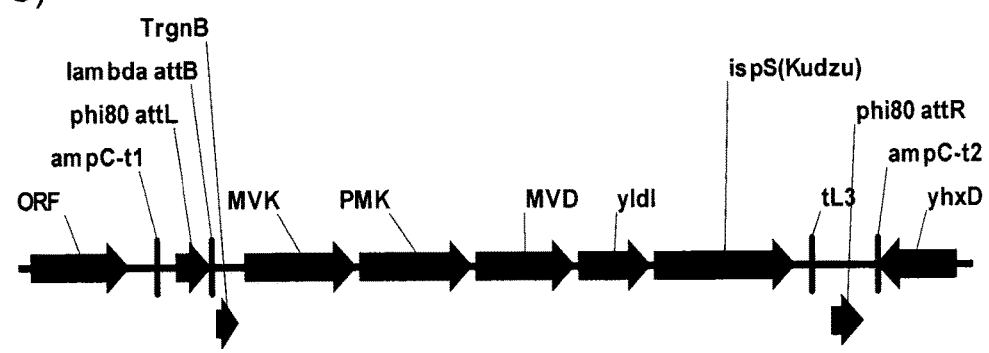

3.4 Construction of P. Ananatis SC17(0) Derivatives Carrying attB Site of phi80 Phage in Different Points of Genome The derivatives of P. ananatis SC17(0) carrying attB site of phi80 phage substituted for the ampC gene, ampH gene or crt operon have been constructed (annotated complete genome sequence of P. ananatis AJ13355 is available as PRJDA162073 or GeneBank accession numbers AP012032.1 and AP012033.1). To obtain these strains, λRed-dependent integration of the PCR-amplified DNA fragments carrying attLphi80-kan-attRphi80 flanked by 40 by regions homologous to the target sites in genome has been performed according to the previously reported procedure (Katashkina, J. I., et al., BMC Mol Biol., 2009; 10: 34). After electroporation, cells were plated on L-agar containing 50 mg/l kanamycin. DNA fragments used for substitution of ampC, ampH genes and crt operon by attLphi80-kan-attRphi80 were amplified in reactions with oligonucleotides 1 (SEQ ID NO:79) and 2 (SEQ ID NO:80), 3 (SEQ ID NO:81) and 4 (SEQ ID NO:82), and 5 (SEQ ID NO:83) and 6 (SEQ ID NO:84), respectively (Table 3). The pMWattphi plasmid (Minaeva, N. I. et al., BMC Biotechnol., 2008; 8: 63) was used as a template in these reactions. The obtained integrants were named SC17(0)ΔampC::attLphi80-kan-attRphi80, SC17(0)ΔampH::attLphi80-kan-attRphi80 and SC17(0)Δcrt::attLphi80-kan-attRphi80. Oligonucleotides 7 (SEQ ID NO:85) and 8 (SEQ ID NO:86), 9 (SEQ ID NO:87) and 10 (SEQ ID NO:88), and 11 (SEQ ID NO:89) and 12 (SEQ ID NO:90) (Table 3) were used for PCR-verification of the SC17(0)ΔampC::attLphi80-kan-attRphi80, SC17(0)ΔampH::attLphi80-kan-attRphi80 and SC17(0)Δcrt::attLphi80-kan-attRphi80 strains, respectively. Maps of the obtained ΔampC::attLphi80-kan-attRphi80, ΔampH::attLphi80-kan-attRphi80 and Δcrt::attLphi80-kan-attRphi80 genome modifications are depicted in FIG. 4A), FIG. 5A) and FIG. 6B), respectively.

Removal of the kanamycin resistance marker from constructed strains was performed according to the procedure and using the pAH129-cat helper plasmid as previously reported (Andreeva, I. G., et al., FEMS Microbiol Lett., 2011; 318(1): 55-60). Oligonucleotides 7 and 8, 9 and 10, and 11 and 12 (Table 3) were used for PCR-verification of the resulting SC17(0)ΔampC::attBphi80, SC17(0)ΔampH::attBphi80, and SC17(0)Δcrt::attBphi80 strains, respectively.

3.5 Construction of the ISP3-S Strain

The pAH162-KKDyI-ispS(K) plasmid described in 3-3) was integrated to the SC17(0)ΔampC::attBphi80 strain described in 3-4) according to the procedure and using the helper plasmid pAH123-cat as previously reported (Andreeva, I. G., et al., FEMS Microbiol Lett., 2011; 318(1): 55-60). Pairs of oligonucleotides 13 (SEQ ID NO:91) and 7, and 14 (SEQ ID NO:92) and 8 (Table 3) were used for PCR verification of the obtained integrant. The vector part of pAH162-KKDyI-ispS(K) was removed from the resulting strain SC17(0)ΔampC::pAH162-KKDyI-ispS(K) using the pMWintxis-cat helper plasmid carrying int and xis genes of λ phage as previously reported (Katashkina, J. I., et al., BMC Mol Biol., 2009; 10: 34). As a result, the SC17(0)ΔampC::KKDyI-ispS(K) strain was obtained. Oligonucleotides 7 and 15 (SEQ ID NO:93) (Table 3) were used for PCR verification of the tetracycline sensitive derivative. Construction of SC17(0)ΔampC::KKDyI-ispS(K) is illustrated in FIG. 4C.

Genomic DNA isolated from the SC17(0)ΔampH::attLphi80-kan-attRphi80 strain described above using GeneElute Bacterial Genomic DNA Kit (Sigma) was electroporated to the SC17(0)ΔampC::KKDyI-ispS(K) strain according to the method of chromosome electroporation as previously reported (Katashkina, J. I., et al., BMC Mol Biol., 2009; 10:3 4). Transfer of the ΔampH::attLphi80-kan-attRphi80 mutation was confirmed in PCR with primers 9 and 10 (Table 3).

The kanamycin resistance marker was excised from the obtained strain using the phi80 Int/Xis-dependent procedure (Andreeva, I. G., et al., FEMS Microbiol Lett., 2011; 318(1): 55-60). After PCR verification of the ΔampC::KKDyI-ispS(K) modification in the obtained KmS recombinants using primers 7 and 15 (Table 3), the SC17(0)ΔampC::KKDyI-ispS(K) ΔampH::attBphi80 strain has been selected.

Figure 5:
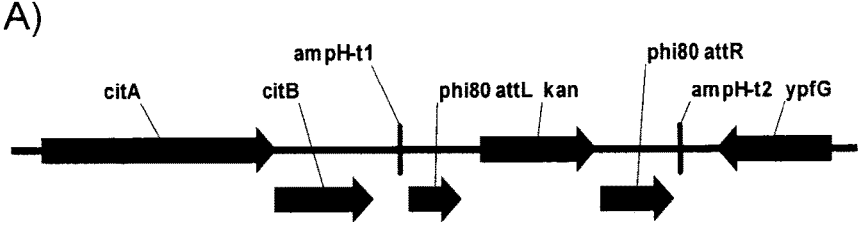
FIG. 5 is a schematic depiction of construction of the ΔampH::Para-mvaES chromosome modification: A) λRed-dependent substitution of the ampH gene by attLphi80-kan-attRphi80 PCR-generated DNA fragment; B) phi80Int-dependent integration of the pAH162-Para-mvaES plasmid; and C) phi80Int/Xis-dependent elimination of vector part of pAH162-Para-mvaES.
Figure 5:
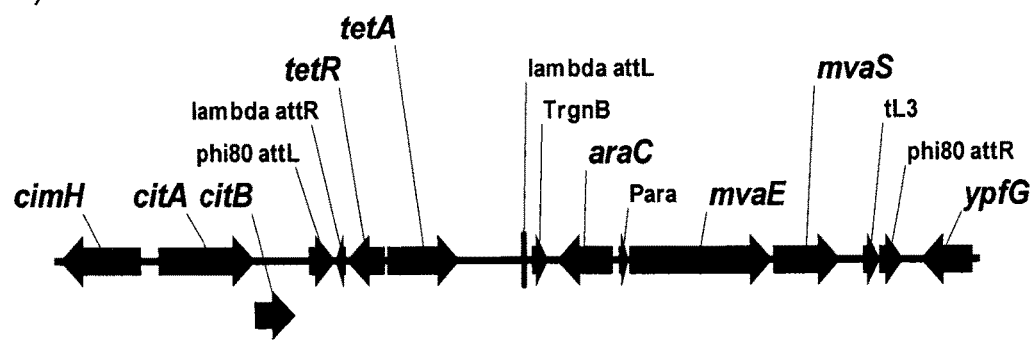
Figure 5:
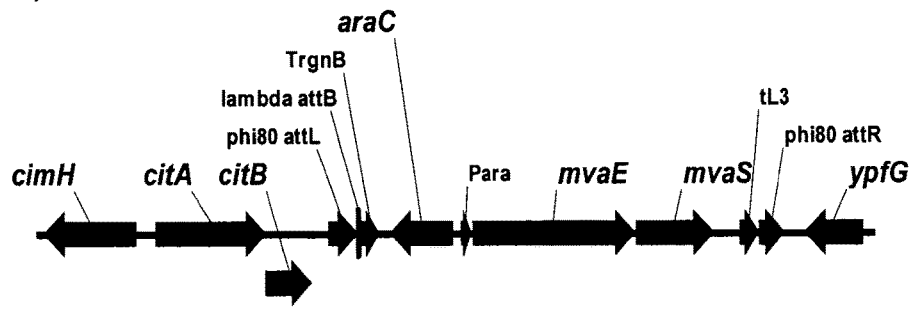
Figure 6:
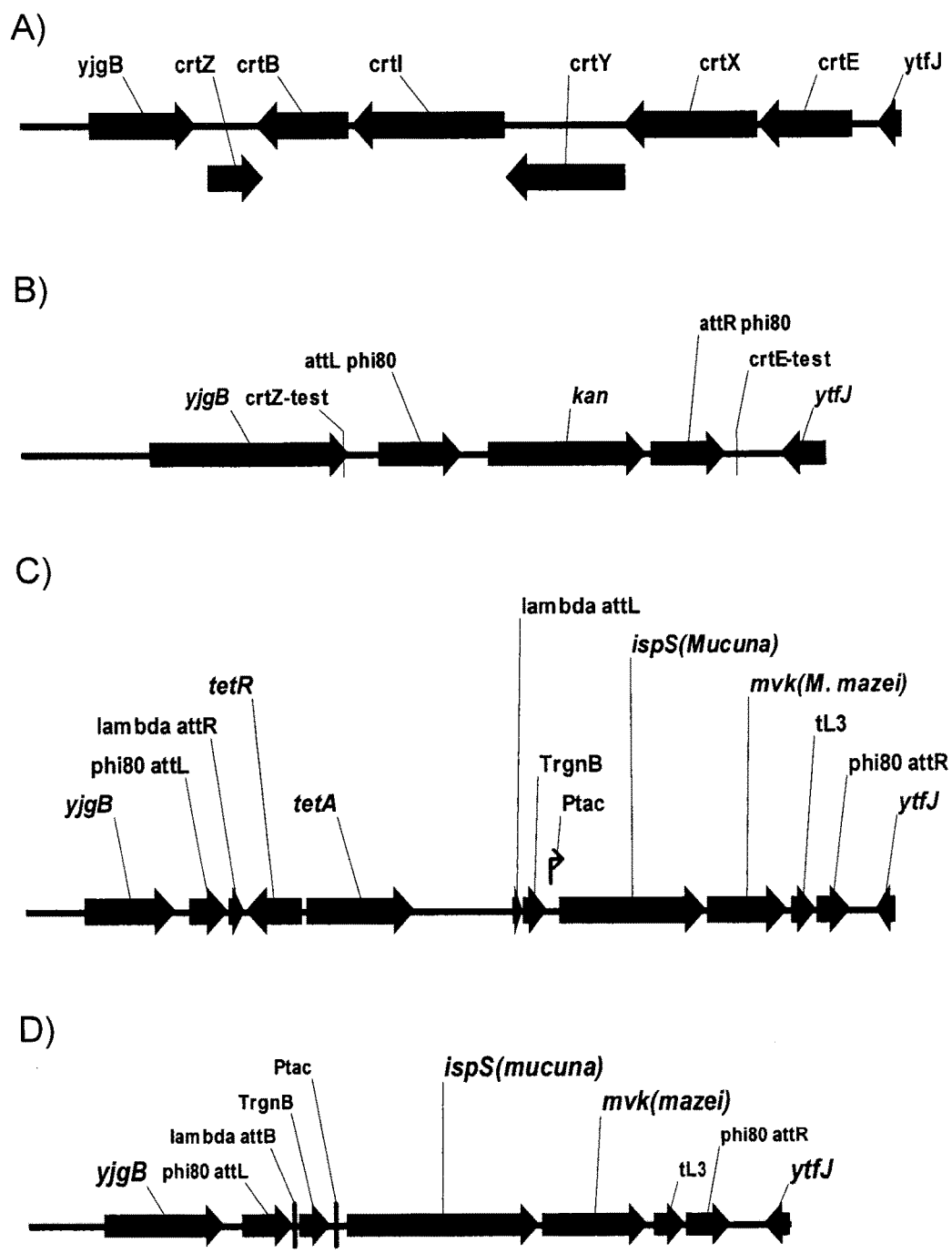
FIG. 6 is a schematic depiction of construction of the Δcrt::KKDyI-ispS(K) modification of pEA320 megaplasmid: A) Structure of the P. ananatis crt locus located in the pEA320 megaplasmid; B) λRed-dependent substitution of the crt operon by attLphi80-kan-attRphi80 PCR-generated DNA fragment; C) phi80Int-dependent integration of the pAH162-Ptac-ispS(M)-mvk(Mma) plasmid; and D) phi80Int/Xis-dependent elimination of vector part of pAH162-Ptac-ispS(M)-mvk(Mma)

The pAH162-Para-mvaES plasmid described above was integrated to SC17(0)ΔampC::KKDyI-ispS(K)ΔampH::attBphi80 using the pAH123-cat helper plasmid (Andreeva, I. G., et al., FEMS Microbiol Lett., 2011; 318(1): 55-60). Pairs of oligonucleotides 13 and 9 and 14 and 10 (Table 3) were used for PCR verification of the obtained integrant. The vector part of pAH162-Para-mvaES was removed from integrants using the phage λ Int/Xis-dependent technique (Katashkina, J. I., et al., BMC Mol Biol., 2009; 10: 34); elimination of vector from chromosome was confirmed in PCR with primers 9 and 94 (SEQ ID NO:79) (Table 3). As a result, the marker-less SC17(0)ΔampC::KKDyI-ispS(K)ΔampH::Para-mvaES strain was obtained. Construction of the ΔampH::Para-mvaES chromosome modification is illustrated in FIG. 5C.

The pAH162-Ptac-ispS(M)-mvk(Mma) plasmid described in 3-4) was integrated to genome of SC17(0)Δcrt::attBphi80 using the previously reported protocol (Andreeva, I. G., et al., FEMS Microbiol Lett. 2011; 318(1): 55-60). Plasmid integration was confirmed in polymerase chain reactions with primers 11 and 13, and 12 and 14 (Table 3).

The chromosome modification SC17(0)Δcrt::pAH162-Ptac-ispS(M)-mvk(Mma) as constructed above has been transferred to the SC17(0)ΔampC::KKDyI-ispS(K)ΔampH::Para-mvaES strain using the method of electroporation with genomic DNA as previously reported (Katashkina, J. I., et al., BMC Mol Biol., 2009; 10: 34). The vector part of pAH162-Ptac-ispS(M)-mvk(Mma) was excised from the obtained integrant using phage Int/Xis-dependent technique as previously reported (Katashkina, J. I., et al., BMC Mol Biol., 2009; 10: 34). Structure of the final construction Δcrt::Ptac-ispS(M)-mvk(Mma) (FIG. 6D) has been confirmed in PCR with primers 11 and 17 (SEQ ID NO:95) (Table 3).

Re-examination of all integrative expression cassettes introduced to this final strain by PCR revealed some unexpected rearrangement at the 5'-portion of the KKDyI operon, containing MVK, PMK, MVD and yldI genes from S. cerevisiae. To restore this cassette, the strain was electroporated with genomic DNA isolated from the SC17(0)ΔampC::pAH162-KKDyI-ispS(K) strain using GeneElute Bacterial Genomic DNA Kit (Sigma) according to the previously reported procedure (Katashkina, J. I., et al., BMC Mol Biol., 2009; 10: 34). The resulting strain contained all genes necessary for isoprene production.

After phage λ Int/Xis-dependent excision of the vector part of pAH162-KKDyI-ispS(K) (see above), the marker-less ISP3-S strain (P. ananatis SC17(0) ΔampC::attLphi80-KKDyI-ispS(K)-attRphi80 ΔampH::attLphi80-Para-mvaES-attRphi80 Δcrt::attLphi80-Ptac-ispS(M)-mvk(Mma)-attRphi80) was obtained.

3.6 Insertion of Tac Promoter

Subsequently, tac promoter was introduced into P. ananatis SC17(0) ΔampC::KKDyI-ispS(K) (hereinafter AG9579) by a λ Red method. A method referred to as "Red-driven integration" or "Red-mediated integration" (Proc. Natl. Acad. Sci. USA., 97. 6640-6645 (2000)) was used in order to perform promoter substitution in Pantoea ananatis. P. ananatis SC17(0) is known to be used as a recipient strain suitable for Red-dependent integration into a chromosome of Pantoea ananatis (U.S. Pat. No. 7,919,284 B2). The helper plasmid RSF-Red-TER that expressed λ gam, bet and exo genes (hereinafter "λ Red genes") was used for the Red-dependent integration (U.S. Pat. No. 7,919,284 B2). The RSF-Red-TER plasmid contains a levansucrase gene (sacB) and this gene allows to recover the plasmid from cells in medium containing sucrose.

The RSF-Red-TER plasmid was introduced into AG9579 by electroporation according to the standard method. The resulting strain was designated as AG9579/RSF-Red-TER. Genomic DNA was extracted from P. ananatis SC17(0) strain Ptac-lacZ (RU application 2006134574, WO2008/090770, US2010062496) and used as the template in PCR. In P. ananatis SC 17(0) strain Ptac-lacZ, λattL-Km$^r$-λattR-Ptac where Ptac promoter was linked downstream of λattL-Km$^r$-λattR is incorporated upstream of a lacZ gene (see WO2011/87139 A1). PCR was carried out using P4071R_6083-54-1 (SEQ ID NO:75) and P4071F(2)_6083-54-3 (SEQ ID NO:76) as the primers and using Prime Star polymerase (supplied from TAKARA BIO Inc.). A reaction solution was prepared according to the composition attached to the kit, and the reaction at 98° C. for 10 seconds, 54° C. for 20 seconds and 68° C. for 120 seconds was carried out in 30 cycles. As a result, a PCR fragment containing a kanamycin resistant gene and the tac promoter was obtained. This PCR fragment was purified and then introduced into AG9579/RSF-Red-TER by electroporation according to the standard method.

AG9579/RSF-Red-TER strain in which the PCR fragment had been introduced was selected in an L medium (10 g of bactotrypsin, 5 g of yeast extract, 5 g of NaCl, 15 g of agar are contained in 1 of pure water, pH 7.0) containing 40 mg/L of kanamycin, and about 20 colonies were obtained as transformants. By PCR using two synthesized DNA primers represented by FCK_6038-52-3 (SEQ ID NO:77) and RCK_6038-52-4 (SEQ ID NO:78), it was confirmed that the sequence derived from the PCR fragment had been inserted upstream of the KKDyI operon. The microbial strain confirmed to have the insertion of the fragment was obtained. Subsequently, the helper plasmid RSF-Red-TER was deleted. This microbial strain was inoculated to the L medium containing 5 g/L of sucrose and 1 mM IPTG to form a single colony. After forming the single colony, this was replicated in both the L medium containing 25 mg/L of chloramphenicol and 40 mg/L of kanamycin and the L medium containing 40 mg/L of kanamycin, and a chloramphenicol sensitive colony was obtained. The microbial strain thus obtained was designated as *P. ananatis* SC17(0) Ptac-KKDyI-ispS(K)(Kmr).

3.7 Construction of Integrative Plasmids Carrying Different Mevalonate Kinase Genes KpnI-BamHI fragments of pMW-Ptac-Mclmvk-Ttrp, pMW-Ptac-Nmrmvk-Ttrp, and pMW-Ptac-Mmamvk-Ttrp plasmids (see Example 3-1) have been sub-cloned into KpnI-Ecl136II recognition sites of the pAH162-λattL-TcR-λattR integrative vector.

BglII-BamHI fragment of pMW-Ptac-Cvamvk-Ttrp (see Example 3-1) was sub-cloned into BamHI-Ecl136II recognition sites of the pAH162-λattL-TcR-λattR integrative vector.

Figure 7:
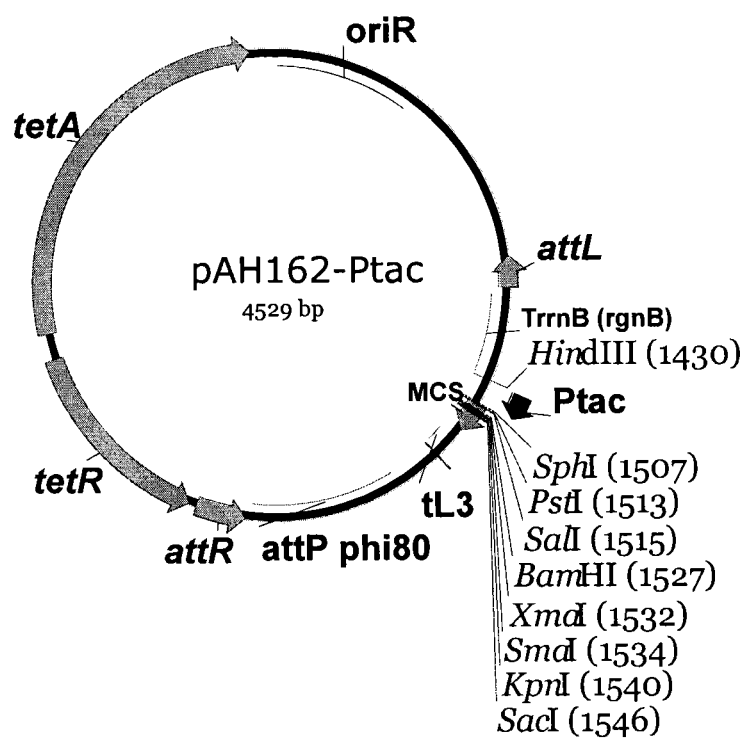
FIG. 7 is a schematic depiction of the pAH162-Ptac integrative expression vector.

A DNA fragment containing Ptac promoter was amplified in PCR with primers 18 (SEQ ID NO:96) and 19 (SEQ ID NO:97) (Table 3) and cloned into the HindIII-SphI recognition sites of the pAH162-λattL-TcR-λattR integrative vector. The cloned promoter fragment was sequenced. Map of the resulting integrative expression vector pAH162-Ptac is represented in FIG. 7.

A chemically synthesized DNA fragment containing putative mvk gene from *Methanocella paludicola* strain SANAE (see GeneBank accession number AP011532 for complete genome sequence) linked to canonical SD sequence was cloned into PstI-KpnI recognition sites of pAH162-Ptac.

Figure 8:
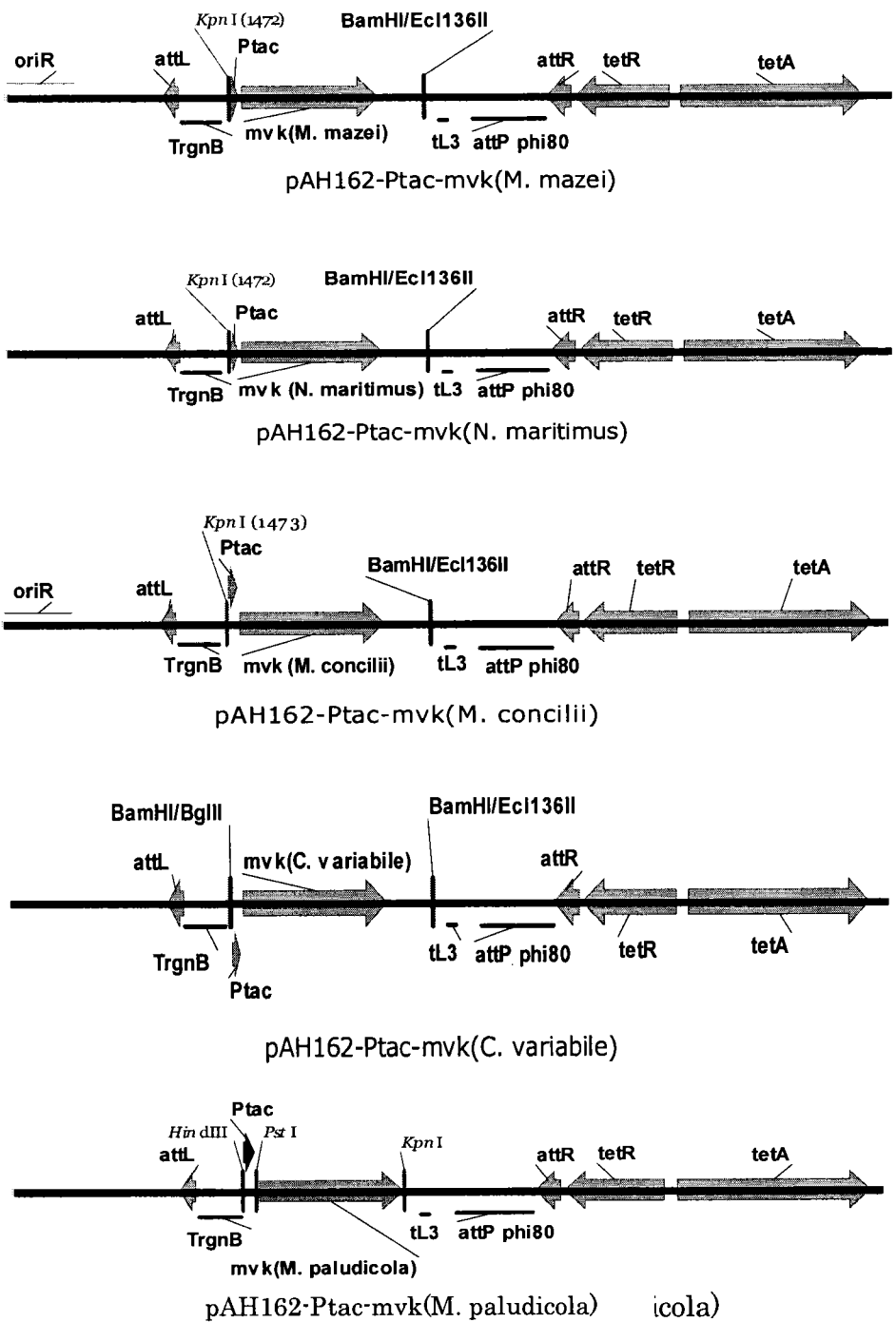
FIG. 8 is a schematic depiction of integrative plasmids carrying mevalonate kinase genes.

Maps of the integrative plasmids carrying different mvk genes are depicted in FIG. 8.

3.8 Construction of ISP3-mvk(Mpd) Strain

The pAH162-Ptac-mvk(*M. paludicola*) plasmid obtained as above was integrated into genome of SC17(0)Δcrt::attBphi80 using pAH123-cat helper plasmid (see above).

The constructed Δcrt::pAH123-Ptac-mvk(*M. paludicola*) chromosome modification was transferred to the ISP3-S strain (see above) via electroporation of genomic DNA isolated from SC17(0)Δcrt::pAH162-Ptac-mvk(*M. paludicola*). The resulting integrant was named ISP3-mvk(Mpd).

3.9 Construction of ISP2 Strain

The pAH162-Ptac-mvk(*M. paludicola*) integrative plasmid was removed from ISP3-mvk(Mpd) using pAH129-cat helper plasmid (see above). Presence of *P. ananatis* SC17 (0)ΔampC::KKDyI-ispS(K) modification in the selected TcS clones was confirmed in PCRs with primers 7 and 13, and 8 and 14 (Table 3), ΔampH::attLphi80-Para-mvaES-attRphi80 modification was confirmed by PCRs with primers 9 and 13, and 10 and 14 (Table 3). As a result, the ISP2 strain (*P. ananatis* SC17(0) ΔampC::attLphi80-KKDyI-ispS(K)-attRphi80 ΔampH::attLphi80-Para-mvaES-attRphi80 Δcrt::attBphi80) was selected.

3.10 Construction of Set of ISP2 Derivatives Carrying Different Mvk Genes

Figure 9:
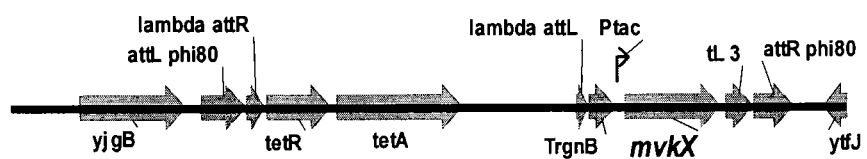
FIG. 9 is a schematic depiction of phi80Int-dependent integration of the pAH162-Ptac-mvk(X) plasmids.

The pAH162-Ptac-mvk(*M. mazei*), pAH162-Ptac-mvk(*C. variabile*), pAH162-Ptac-mvk(*N. maritimus*) and pAH162-Ptac-mvk(*M. concilii*) (see above) were integrated to the ISP2 strain using pAH123-cat helper plasmid as previously reported (Andreeva, I. G., et al., FEMS Microbiol Lett., 2011; 318(1): 55-60). As a result, a set of strains named ISP3-mvk(Mma), ISP3-mvk(Cva), ISP3-mvk(Nmr) and ISP3-mvk(Mcl), respectively, was obtained. FIG. 9 illustrates structures of the Δcrt::pAH162-Ptac-mvk(X) where mvk(X) is any of the mvk genes listed above.

3.11 Construction of ISP3.2-mvk(Mpd) Strain

Genomic DNA isolated from *P. ananatis* SC17(0) ΔampC::Ptac-KKDyI-ispS(K)(Kmr) strain was electroporated to the ISP3-mvk(Mpd) strain. As a result, the ISP3.2-mvk(Mpd)-KmR strain (*P. ananatis* SC17(0) ΔampC::λattL-kan-λattR-Ptac-KKDyI-ispS(K) ΔampH::attLphi80-Para-mvaES-attRphi80 Δcrt::pAH162-Ptac-mvk(*M. paludicola*)) was obtained.

Kanamycin resistance gene was removed from the strain using λInt/Xis-dependent procedure (Katashkina, J. I., et al., BMC Mol Biol., 2009; 10: 34). As a result, the ISP3.2-mvk (Mpd) strain was obtained.

3.12 Construction of ISP2.2 Strain

The pAH162-Ptac-mvk(*M. paludicola*) plasmid was removed from the ISP3.2-mvk(Mpd) strain using pAH129 helper plasmid (Andreeva, I. G., et al., FEMS Microbiol Lett., 2011; 318(1): 55-60). Presence of ΔampC::Ptac-KKDyI-ispS(K) modification in the selected TcS clones was confirmed in PCRs with primers 7 and 13, and 8 and 14 (Table 3), ΔampH::attLphi80-Para-mvaES-attRphi80 modification was confirmed by PCRs with primers 9 and 13, and 10 and 14 (Table 3). As a result, the ISP2.2 strain (*P. ananatis* SC17(0) ΔampC::Ptac-KKDyI-ispS(K) ΔampH:: attLphi80-Para-mvaES-attRphi80 Δcrt::attBphi80) was selected.

3.13 Construction of Set of ISP2.2 Derivatives Carrying Different Mvk Genes

The pAH162-Ptac-mvk(*M. mazei*) and pAH162-Ptac-mvk(*M. concilii*) (see above) were integrated to the ISP2.2 strain using pAH123-cat helper plasmid as previously reported (Andreeva, I. G., et al., FEMS Microbiol Lett., 2011; 318(1): 55-60). As a result, strains named ISP3.2-mvk (Mma) and ISP3.2-mvk(Mcl), respectively, were obtained.

TABLE 3

| | | Oligonucleotides used for primers |
|---|---|---|
| 1 | DampC-phL | 5'-CTGATGAACTGTCACCTGAATGAGTGCTGATGAAAATATAGA AAGGTCATTTTTCCTGAATATGCTCA-3' (SEQ ID NO: 79) |
| 2 | DampC-phR | 5'-ATTCGCCAGCATAACGATGCCGCTGTTGAGCTGAGGAACACG TTTGTTGACAGCTGGTCCAATG-3' (SEQ ID NO: 80) |
| 3 | ampH-attL-phi80 | 5'-ATGCGCACTCCTTACGTACTGGCTCTACTGGTTTCTTTGCGAA AGGTCATTTTTCCTGAATATGCTCACA-3' (SEQ ID NO: 81) |
| 4 | ampH-attR-phi80 | 5'-TTAAGGAATCGCCTGGACCATCATCGGCGAGCCGTTCTGACGT TTGTTGACAGCTGGTCCAATG-3' (SEQ ID NO: 82) |

TABLE 3-continued

Oligonucleotides used for primers

| | | |
|---|---|---|
| 5 | crtZ-attLphi80 | 5'-ATGTTGTGGATTTGGAATGCCCTGATCGTTTTCGTTACCGGAA<br>AGGTCATTTTTCCTGAATATGCTCA-3' (SEQ ID NO: 83) |
| 6 | crtE-attRphi80 | 5'-ATGACGGTCTGCGCAAAAAAACACGTTCATCTCACTCGCGCGT<br>TTGTTGACAGCTGGTCCAATG-3' (SEQ ID NO: 84) |
| 7 | ampC-t1 | 5'-GATTCCCACTTCACCGAGCCG-3' (SEQ ID NO: 85) |
| 8 | ampC-t2 | 5'-GGCAGGTATGGTGCTCTGACG-3' (SEQ ID NO: 86) |
| 9 | ampH-t1 | 5'-GCGAAGCCCTCTCCGTTG-3' (SEQ ID NO: 87) |
| 10 | ampH-t2 | 5'-AGCCAGTCAGCCTCATCAGCG-3' (SEQ ID NO: 88) |
| 11 | crtZ-test | 5'-CCGTGTGGTTCTGAAAGCCGA-3' (SEQ ID NO: 89) |
| 12 | crtE-test | 5'-CGTTGCCGTAAATGTATCCGT-3' (SEQ ID NO: 90) |
| 13 | ag-phL-test | 5'-GTTCGCAGAGTGTTATGGTTTACATCC-3' (SEQ ID NO: 91) |
| 14 | ag-phR-test | 5'-GATTGGTGGTTGAATTGTCCGTAAC-3' (SEQ ID NO: 92) |
| 15 | KKDyI-s-3' | 5'-TGGAAGGATTCGGATAGTTGAG-3' (SEQ ID NO: 93) |
| 16 | mvaES-s-3' | 5'-GGCAATCAGCACTTCCGC-3' (SEQ ID NO: 94) |
| 17 | ispS-Seq2 | 5'-GGTTCGTATTTATCCAGCAGCCA-3' (SEQ ID NO: 95) |
| 18 | tac5HindIII | 5'-GCTTAAAGCTTCCCTGTTGACAATTAATCATCGG-3' (SEQ ID NO: 96) |
| 19 | tac3SphI | 5'-CTGTTGCATGCTGTGTGAAATTGTTATCCGCTCAC-3' (SEQ ID NO: 97) |

3.14 Isoprene Fermentation Utilizing Isoprene-producing Strain Derived from *P. Ananatis*

3.14.1 Construction of Microbial Strain

Isoprene-producing strain was constructed by introducing the IspS plasmid to above strains (Table 4).

TABLE 4

Isoprene-producing strain of *P. ananatis*

| Name | Parent strain | Microbial species from which MVK was derived | IspS plasmid |
|---|---|---|---|
| ISP3-mvk(Mma) | ISP2 | *M. mazei* | pSTV28-Ptac-IspSK |
| ISP3-mvk(Mpd) | ISP3-S | *M. paludicola* | pSTV28-Ptac-IspSK |
| ISP3-mvk(Mcl) | ISP2 | *M. concilii* | pSTV28-Ptac-IspSK |
| ISP3-mvk(Cva) | ISP2 | *C. variable* | pSTV28-Ptac-IspSK |
| ISP3-mvk(Nmr) | ISP2 | *N. maritimus* | pSTV28-Ptac-IspSK |
| ISP3.2-mvk(Mma) | ISP2.2 | *M. mazei* | pSTV28-Ptac-IspSK |
| ISP3.2-mvk(Mpd) | ISP3-mvk(Mpd) | *M. paludicola* | pSTV28-Ptac-IspSK |
| ISP3.2-mvk(Mcl) | ISP2.2 | *M. concilii* | pSTV28-Ptac-IspSK |

3.14.2 Condition for Jar Culture of *P. Ananatis* Isoprene-producing Strain

A fermentation jar having a 1 volume was used for the culture of the *P. ananatis* isoprene-producing strain. A glucose medium was prepared in a composition shown in Table 5. The novel MVK-introduced strain was applied onto an LB plate containing 60 mg/L of chrolamphenicol, and cultured at 34° C. for 16 hours. 0.3 L of the glucose medium was added to the fermentation jar having the 1 L volume, and microbial cells sufficiently grown on one plate were inoculated thereto, and the culture was started. The culture was carried out under a condition at pH 7.0 (controlled by ammonia gas) at 30° C. with ventilation at 150 mL/minute or 300 mL/minute. A stirring control was carried out so that a concentration of oxygen in the medium was 5% or more. During the culture, a solution of glucose adjusted at 500 g/L was continuously added so that a concentration of glucose was 10 g/L or more. In the case of cultivating ISP3-mvk(X) (where mvk(X) is any of the microbial species from which MVK was derived and listed in Table 4), ISP3-mvk (Mpd), ISP3-mvk (Mma), ISP3-mvk (Cva), ISP3-mvk (Mcl) and ISP3-mvk (Nmr) finally consumed 64.1 g, 71.7 g, 79.1 g, 64.3 g and 71.3 g of glucose, respectively, in the culture for 70 hours. Also, in the case of cultivating ISP3.2-mvk(X) (where mvk(X) is any of the microbial species from which MVK was derived and listed in Table 4), ISP3.2-mvk (Mma), ISP3.2-mvk (Mpd) and ISP3.2-mvk (Mcl) finally consumed 64.3 g, 60.1 g and 67.2 g of glucose, respectively, in the culture for 48 hours.

TABLE 5

Composition of glucose medium

| | Final concentration |
|---|---|
| Group A | |
| Glucose | 80 g/L |
| MgSO4•7H2O | 2.0 g/L |
| Group B | |
| (NH4)2SO4 | 2.0 g/L |
| KH2PO4 | 2.0 g/L |
| FeSO4•7H2O | 20 mg/L |
| MnSO4•5H2O | 20 mg/L |
| Yeast Extract | 4.0 g/L |

0.15 L each of Group A and Group B was prepared, and then sterilized with heat at 115° C. for 10 minutes. After cooling, Group A and Group B were mixed, and chloramphenicol (60 mg/L) was added, and used as the medium.

3.14.3 Method for Inducing Isoprene Production Phase

In *P. ananatis* isoprene-producing strain, genes upstream of the mevalonic acid pathway are expressed by an arabinose inducible promoter, and thus an amount of isoprene produced in the presence of L-arabinose (Wako Pure Chemical Industries, Ltd.) is notably enhanced. To induce to an isoprene production phase, a broth in the fermentation jar was analyzed with time, and L-arabinose was added so that its final concentration was 20 mM at a time point when an absorbance at 600 nm was 16.

3.14.4 Method for Measuring Concentration of Isoprene in Fermentation Gas

After the addition of L-arabinose, fermentation gas was collected in a gas bag on a timely basis, and the concentration of isoprene gas was quantified by gas chromatography (GC-2010 Plus AF supplied from Shimadzu Corporation) or multi gas analyzer (F10 supplied from GASERA Ltd.).

3.15 Amount of Isoprene Produced in Jar Culture of MVK Introduced Strain (Evaluation 1)

Figure 10:
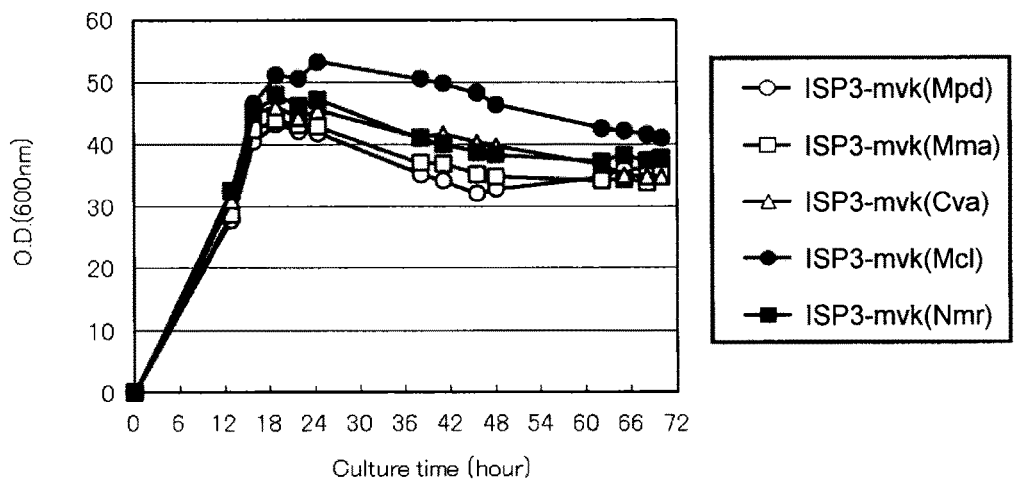
FIG. 10 is a graph showing growth with time of MVK-introduced strains, ISP3-mvk (Mma), ISP3-mvk (Mpd), ISP3-mvk (Mcl), ISP3-mvk (Cva), and ISP3-mvk (Nmr) in jar culture.
Figure 11:
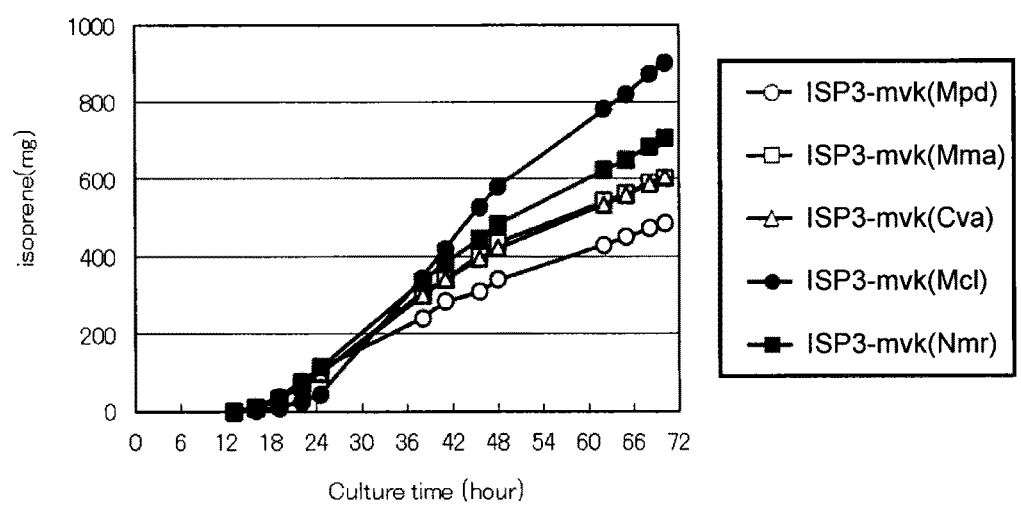
FIG. 11 is a graph showing amounts (mg) of isoprene produced by cultivation of the MVK-introduced strains, ISP3-mvk (Mma), ISP3-mvk (Mpd), ISP3-mvk (Mcl), ISP3-mvk (Cva), and ISP3-mvk (Nmr) in jar culture.

Novel MVK introduced strains, ISP3-mvk (Mma), ISP3-mvk (Mpd), ISP3-mvk (Mcl), ISP3-mvk (Cva) and ISP3-mvk (Nmr) were cultured under the above jar culture condition, and amounts of produced isoprene were measured. The amount of total isoprene produced until 70 hours after starting the culture was measured as shown in FIGS. 10 and 11. The strains arranged in descending order of total produced isoprene amount were as follows: ISP3-mvk (Mcl), ISP3-mvk (Nmr), ISP3-mvk (Cva), ISP3-mvk (Mma) and ISP3-mvk (Mpd) (FIGS. 10 and 11). The each total amounts of isoprene produced in ISP3-mvk (Mcl), ISP3-mvk (Nmr), ISP3-mvk (Cva), ISP3-mvk (Mma) and ISP3-mvk (Mpd) were 903 mg, 707 mg, 606 mg, 603 mg and 486 mg, respectively. This indicates that *P. ananatis* isoprene-producing strain in which MVK derived from *M. concilii*, *N. maritimus*, or *C. variabile* was introduced has more excellent ability to produce isoprene than *P. ananatis* isoprene-producing strain in which known MVK derived from *M. mazei* was introduced.

3.16 Amount of Isoprene Produced in Jar Culture of MVK Introduced Strain (Evaluation 2)

Figure 12:
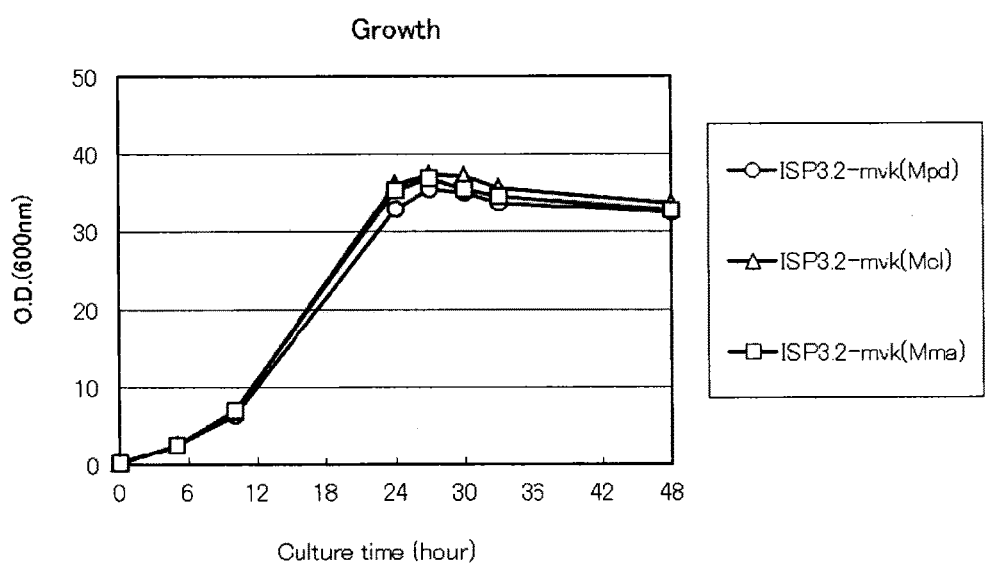
FIG. 12 is a graph showing growth with time of MVK-introduced strains, ISP3.2-mvk (Sce), ISP3.2-mvk (Mma), ISP3.2-mvk (Mpd) and ISP3.2-mvk (Mcl) in jar culture.
Figure 13:
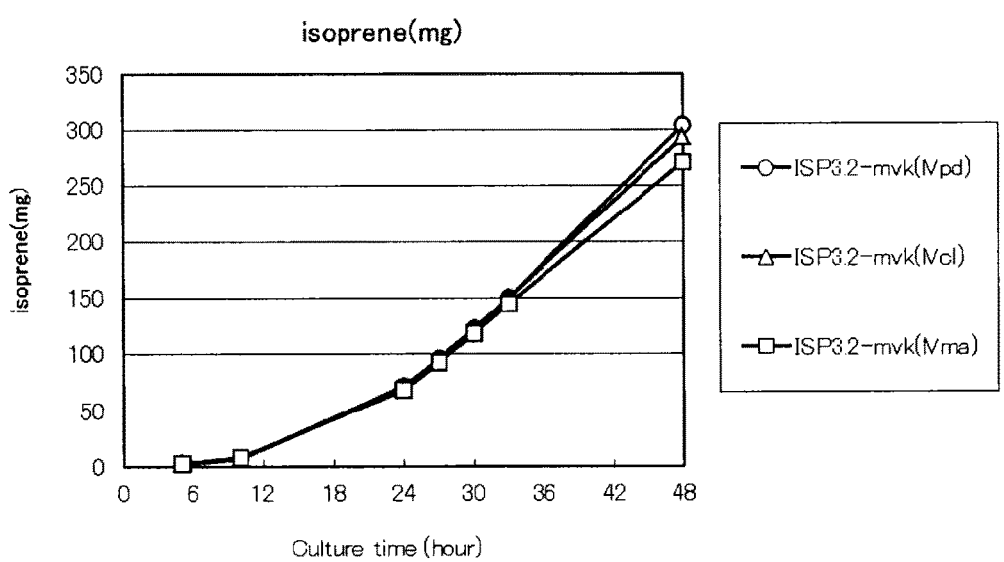
FIG. 13 is a graph showing amounts (mg) of isoprene produced by cultivation of the MVK-introduced strains, ISP3.2-mvk (Sce), ISP3.2-mvk (Mma), ISP3.2-mvk (Mpd) and ISP3.2-mvk (Mcl) in jar culture.

Novel MVK-introduced strains, ISP3.2-mvk (Mma), ISP3.2-mvk (Mpd), and ISP3.2-mvk (Mcl) were cultured under the above jar culture condition, and amounts of produced isoprene were measured. As shown in FIGS. 12 and 13, total amounts of isoprene produced for 48 hours after starting the cultivation were measured. The strains arranged in descending order of the total amount of the isoprene produced were as follows: ISP3.2-mvk (Mpd), ISP3.2-mvk (Mcl) and ISP3.2-mvk (Mma) (FIGS. 12 and 13). The total amounts of the isoprene produced in ISP3.2-mvk (Mpd), ISP3.2-mvk (Mcl) and ISP3.2-mvk (Mma) was 307 mg, 301 mg and 275 mg, respectively. This indicates that *P. ananatis* isoprene-producing strain in which MVK derived from *M. paludicola* or *M. concilii* was introduced has more excellent ability to produce isoprene than *P. ananatis* isoprene-producing strain in which known MVK derived from *M. mazei* was introduced.

Example 4

Purification and Activity Assay of Mevalonate Kinase 4.1 Cloning of Mevalonate Kinase Genes Each mevalonate kinase gene was cloned in pET-21a(+) (for C-terminal His-Tag: Novagen) and pET-28b(+) (for N-terminal His-Tag: Novagen). Using the plasmids shown in Table 6 as template, PCR was performed with oligonucleotides shown in Table 7. Since mpd-mvk includes NdeI site in ORF, silent mutation was introduced in NdeI site by overlap PCR. KOD plus DNA polymerase (TOYOBO) was used for PCR. Obtained DNA fragments were digested with NdeI and HindIII and inserted in the corresponding sites of pET-21a(+) and pET-28b(+). Inserted DNA sequences were confirmed by DNA sequencing. An ERG12 gene (sce-mvk in Table 6) encoding the mevalonate kinase in *Saccharomyces cerevisiae* was amplified by PCR performed with Prime Star polymerase (supplied from Takara Bio Inc.) using synthetic oligonucleotides consisting of the nucleotide sequences of SMVKf (SEQ ID NO:100) and SMVKr (SEQ ID NO:101) as the primers with genomic DNA from *Saccharomyces cerevisiae* as the template. A reaction solution was prepared according to the composition attached to the kit, and the reaction at 98° C. for 10 seconds, 55° C. for 5 seconds and 72° C. for one minute per kb was performed in 30 cycles. As a result, PCR products containing an ERG12 gene was obtained. Likewise, pMW219-Ptac-Ttrp was amplified by PCR performed with Prime Star polymerase (supplied from Takara Bio Inc.) using synthetic oligonucleotides consisting of the nucleotide sequences of PtTt219f (SEQ ID NO:65) and PtTt219r (SEQ ID NO:66) as the primers. As a result, a PCR product containing pMW219-Ptac-Ttrp was obtained. Subsequently, the purified PCR product of ERG12 gene was ligated to the PCR product of pMW219-Ptac-Ttrp using In-Fusion HD Cloning Kit (supplied from Clontech). The resulting expression plasmids for ERG12 gene was designated as pMW-Ptac-Scemvk-Ttrp.

Primer 1 for amplifying ERG12mvk gene (SMVKf) (SEQ ID NO:100)

5'-tttcacacaa ggagactccc atgtcattac cgttcttaac-3'

Primer 2 for amplifying ERG12mvk gene (SMVKr) (SEQ ID NO:101)

5'-cagcggaact ggcggctccc ttatgaagtc catggtaaat-3'

TABLE 6

Plasmids, coding genes and their gene sources

| Plasmid name | Coding gene | mvk gene source |
|---|---|---|
| pUC57-Mclmvk | mcl-mvk | *Methanosaeta concilii* |
| pSTV-Ptac-ispSK-Mpdmvk | mpd-mvk | *Methanocella paludicola* |
| pUC57-Nmrmvk | nmr-mvk | *Nitrosopumilus maritimus* |
| pUC57-Cvamvk | cva-mvk | *Corynebacterium variabile* |
| pMW-Ptac-Mmamvk-Ttrp | mma-mvk | *Methanosarcina mazei* |
| pMW-Ptac-Scemvk-Ttrp | sce-mvk | *Saccharomyces cerevisiae* |

TABLE 7

Primers used for PCR of each mvk gene

| Gene | Name | Sequence (5'-3') |
|---|---|---|
| mcl-mvk | mcl-mvk-Nde-F | GCAATTCCATATGACGATGGCTTCCGCTCCGGGCAA (SEQ ID NO: 102) |

TABLE 7-continued

Primers used for PCR of each mvk gene

| Gene | Name | Sequence (5'-3') |
|---|---|---|
| mcl-mvk | mcl-mvk-Hind-R | CCCAAGCTTACGCGACTTCCAGGCGAACACCTT (SEQ ID NO: 103) |
| mpd-mvk | mpd-mvk-NdeI-F | GCAATTCCATATGACGATGTGTTCAGCCCCCGGTAA (SEQ ID NO: 104) |
| mpd-mvk | mpd-mvk-NdeI-mut-F | GGATGCATGGTGGCCATTTGCGATGACAAA (SEQ ID NO: 105) |
| mpd-mvk | mpd-mvk-Nd I-mut-R | TTTGTCATCGCAAATGGCCACCATGCATCC (SEQ ID NO: 106) |
| mpd-mvk | mpd-mvk-Hind-R | CCCAAGCTTATTGGATGAATATTCCCTCCGCCGTT (SEQ ID NO: 107) |
| nmr-mvk | nmr-mvk-NdeI-F | GCAATTCCATATGAAGAGCAAGGCATCTGCGCC (SEQ ID NO: 108) |
| nmr-mvk | nmr-mvk-Hind-R | CCCAAGCTTAAAACGTGTCCAGGCCCTTGAAATC (SEQ ID NO: 109) |
| cva-mvk | cva-mvk-NdeI-F | GCAATTCCATATGGCCCCGCACGTCGGTCA (SEQ ID NO: 110) |
| cva-mvk | cva-mvk-Hind-R | CCCAAGCTTATTGCATCACTTCACCTGCCATCTGACC (SEQ ID NO: 111) |
| mma-mvk | mma-mvk-NdeI-F | GCAATTCCATATGGTATCCTGTTCTGCGCCGG (SEQ ID NO: 112) |
| mma-mvk | mma-mvk-Hind-R | CCCAAGCTTAATCTACTTTCAGACCTTGCTCGGTC (SEQ ID NO: 113) |
| sce-mvk | sce-mvk-NdeI-F | GCAATTGCATATGTCATTACCGTTCTTAACTTCTGC (SEQ ID NO: 114) |
| sce-mvk | sce-mvk-Hind-R | CCCAAGCTTATGAAGTCCATGGTAAATTCGTGTT (SEQ ID NO: 115) |
| mcl-mvk | mcl-mvk-H-HindR(pET21) | CCCAAGCTTCGCGACTTCCAGGCGAACACCTT (SEQ ID NO: 116) |
| mpd-mvk | mpd-mvk-H-HindR(pET21) | CCCAAGCTTTTGGATGAATATTCCCTCCGCCGTT (SEQ ID NO: 117) |
| nmr-mvk | nmr-mvk-H-Hind-R(pET21) | CCCAAGCTTAAACGTGTCCAGGCCCTTGAAATC (SEQ ID NO: 118) |
| cva-mvk | cva-mvk-H-Hind-R(pET21) | CCCAAGCTTTTGCATCACTTCACCTGCCATCTGACC (SEQ ID NO: 119) |
| mma-mvk | mma-mvk-H-Hind-R(pET21) | CCCAAGCTTATCTACTTTCAGACCTTGCTCGGTC (SEQ ID NO: 120) |
| sce-mvk | ce-mvk-H-Hind-R(pET21) | CCCAAGCTTATGAAGTCCATGGTAAATTCGTGTT (SEQ ID NO: 121) |

4.2 Preparation of Mevalonate from Mevalonolactone and Verification by HPLC 260 mg of mevalonolactone (ADEKA) was mixed well with 5 ml of water, and then with 0.6 ml of 10N KOH. The mixed solution was then incubated at 37° C. for 2 hours. After incubation, pH of the solution was adjusted to 8.0 by neutralization with hydrochloric acid. Then, the solution was topped up to a final volume of 20 ml, and designated as 100 mM potassium mevalonate solution. Obtained potassium mevalonate solution was subdivided into about 2 ml each, and then stored at −20° C.

The obtained 100 mM potassium mevalonate solution was verified by HPLC. Analysis was performed by using 50 mM (R)-lithium mevalonate (authentic preparation, SIGMA) as the standard and the prepared potassium mevalonate (diluted to 50 mM with water) as a sample. HPLC used for the verification was HITACH High-Performance Liquid Chromatography (L-2000). HPLC was performed by using YMC-Pack ODS-A (150×4.6 mm I.D.: YMC CO., LTD.) as stationary phase and phosphoric acid (pH2.5) as mobile phase. Detection was performed at 210 nm.

In HPLC chromatograms of 50 mM solutions of mevalonolactone, lithium mevalonate standard and potassium mevalonate obtained from alkaline hydrolysis, it was confirmed that the peak at 11.2 min found in authentic mevalonolactone preparation almost disappeared and the peak at 8.8 min found in the authentic mevalonate preparation was the chief component of the prepared mevalonate (data not shown). After frozen storage, the prepared mevalonate was again analyzed by HPLC for stability verification. Peak area of lithium mevalonate standard is almost comparable to that of prepared potassium mevalonate (data not shown), showing that the prepared mevalonate was stable even after frozen storage.

4.3 Expression Analysis and Activity Confirmation

Each obtained plasmid was used for transformation of *E. coli* BL21(DE3). For the analysis of the expression of mevalonate kinases cloned in pET-21a(+) and pET-28b(+), each transfectant was cultured at 20° C. by reciprocal shaking at 140 rpm (TITEC reciprocal shaker) in LB medium in LB medium (tryptone 10 g/L, yeast extract 5 g/L, NaCl 5 g/L) containing 0.1 mg/ml ampicillin (for pET-21a (+)) or 0.05 mg/ml kanamycin (for pET-28b(+)). When OD600 reached approximately 0.5, IPTG was added to the solution to final concentration of 1 mM. It was then cultured overnight at 20° C. Harvested cells were suspended in the buffer solution consisting of 50 mM sodium phosphate, 0.3 M NaCl and 20 mM Imidazol. Then the cells were disrupted with an ultrasonic disruptor (TOMY: UD-201, output level=3.5). After centrifugation (20,000×g, 20 min), disrupted cells were adsorbed to His-spinTrap (GE Healthcare). After washing with the same buffer solution, protein was eluted with the buffer solution consisting of 50 mM sodium phosphate, 0.3 M NaCl and 0.5 M imidazole (pH7.5). Eluate was dialyzed overnight at 4° C. with the external solution composed of 20 mM Tris-HCl (pH7.5) and 50 mM NaCl. Then, enzyme activity of each eluate in the internal dialysis solution was measured.

Activity of the internal dialysate (about 0.2 ml each) was measured with the 10 μl of enzyme solution (Table 8). Enzyme expression level was compared on activity basis between pET-21a(+) and pET-28b(+). Enzyme expressed in pET-28b(+) showed higher activity. It is inferred that expression level is higher in pET-28b(+). Therefore, purified enzyme expressed in pET-28b(+) was used in the further examinations.

TABLE 8

Comparison of the enzyme activity in the cell extract expressed in pET systems

|  | pET28 system (N terminal Tag) | pET21 system (C terminal Tag) |
| --- | --- | --- |
| cva-mvk | 0.211 | 0.019 |
| mcl-mvk | 0.023 | 0.003 |
| mma-mvk | 0.231 | 0.225 |
| mpd-mvk | 0.031 | 0.011 |
| nmr-mvk | 0.247 | 0.137 |
| sce-mvk | 0.127 | 0.001 |

Values were presented by decrease in absorbance per unit time per 10 μl in the enzyme reaction measurement system (dABS/min/10 μl).

4.4 Expression and Purification of Mevalonate Kinase

Each obtained plasmid was used for transformation of *E. coli* BL21(DE3). For the analysis of the expression of mevalonate kinase derived from cva, mma, nmr and sce, each transfectant was cultured at 20° C. in 20 ml of LB medium in a thick test tube (3 cm I.D.×20 cm) by reciprocal shaking at 140 rpm (TAITEC reciprocal shaker). For the analysis of the expression of mevalonate kinase derived from mcl and mpd, each transfectant was cultured at 20° C. in 2 L LB medium in 3 L shaking flask with baffles by gyratory culture at 140 rpm (INOVA44, 2-inch stroke, Newbrunswick sceientific). When OD600 reached approximately 0.5, 0.1 mM IPTG (for cva, mma, nmr, and sce) or 1 mM (for mcl and mpd) of IPTG was added, and then the mixture was kept at 20° C. overnight to induce the target protein. Harvested cells were suspended in buffer solution A (50 mM sodium phosphate, 0.3 M NaCl and 20 mM Imidazol), and then the cells were disrupted with an ultrasonic disruptor (TOMY: UD-201). Ultrasonic disruption of the transfectant expressing mevalonate kinase derived from cva, mma, nmr or sce was performed at output level=3.5, while that of the transfectant expressing mevalonate kinase derived from mcl or mpd at output level=8. After centrifugation (28,000×g, 30 min), the supernatant was adsorbed onto His-Trap HP (GE Healthcare) to elute the target protein by linear concentration gradient of Imidazol (final concentration 0.5 M). Obtained protein was dialyzed by using an external solution composed of 20 mM Tris-HCl (pH 8.0) containing 1 mM DTT and 50 mM NaCl. Dialyzed protein was designated as purified enzyme. Protein quantity was measured with Bio-RAD protein assay kit and BSA standard condition.

Figure 14:
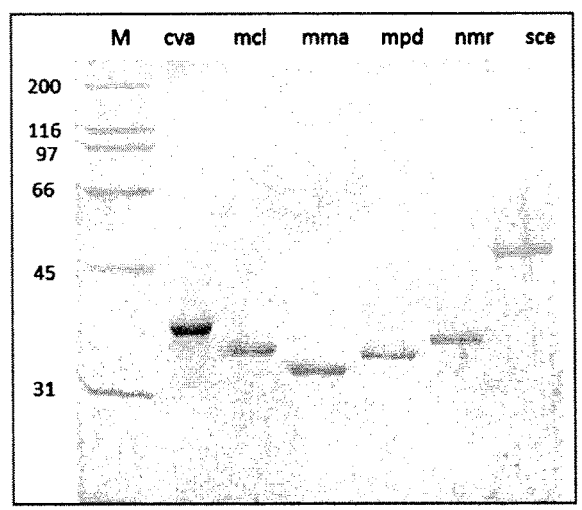
FIG. 14 is a rendering of SDS-PAGE of each purified enzyme; enzymes derived from cva (5 µg), mcl (3 µg), mma (3 µg), mpd (3 µg), nmr (3 µg), sce (3 µg) were loaded on 10% gel; CBB-R250 was used for staining.

As a result, weights of purified cva, mma, nmr and sce-derived enzymes obtained from 20 ml of the culture solutions were 4, 1, 1.8 and 0.2 mg, respectively. Weights of purified mcl and mpd-derived enzymes obtained from 2 L of the culture solutions were 45 and 2 mg, respectively. FIG. 14 shows SDS-PAGE profile of the purified enzymes.

4.5 Measurement of Activity and Km Value of Mevalonate Kinase

For measuring enzyme activity, enzyme was added to the reaction solution containing 50 mM Tris-HCl (pH7.6) (WAKO), 0.4 mM phosphoenolpyruvate (PEP) (SIGMA), 0.33 mM NADH (ORIENTAL YEAT CO., LTD.), 10 mM MgCl2, 0.05 mM DTT, 50 mM NaCl, Lactate Dehydrogenase (LDH) (20 U/ml) (SIGMA), Pyruvate Kinase (PK) (20 U/ml) (SIGMA), 5 mM potassium mevalonate and 5 mM ATP (ORIENTAL YEAT CO., LTD.). Decrease in absorbance at 340 nm at 30° C. was measured to determine the enzyme activity. JASCO Corporation's spectrophotometer (V-650) was used in this study. Millimolar extinction coefficient of NADH used in this study was 6.22 mM$^{-1}$ cm$^{-1}$. Km value (for mevalonate) was measured as follows: ATP concentration in the aforementioned reaction mixture was set at 5 mM, and 3 concentration levels of potassium mevalonate were set in 0.002 mM to 1 mM range. Km value (for ATP) was measured as follows: Potassium mevalonate concentration in the aforementioned reaction mixture was set at 5 mM, and 3 to 4 ATP concentration levels were set in the 0.2 mM to 5 mM range. Km value was calculated by Lineweaver-Burk plot.

Measured activity of each enzyme (JABS/min) was presented on Table 9 for the calculation of apparent Km value (Km app.) of each enzyme. Table 10 presents Km app., Vmax, molecular weight of the enzyme protein, protein concentration in the enzyme solution and calculated $k_{cat}$. The results show that mcl- and mpd-derived enzymes have higher affinity to mevalonate and ATP than the other enzymes.

TABLE 9

Activity data used for the calculation of Km app.

| | mev (mM) | dABS/min | | | ATP(mM) | dABS/min | | |
|---|---|---|---|---|---|---|---|---|
| cva | 0.2 | 0.0771 | 0.07712 | 0.07711 | 5 | 0.03739 | 0.037439 | 0.03741 |
| | 0.04 | 0.03701 | 0.03703 | 0.03697 | 1 | 0.02063 | 0.020153 | 0.02051 |
| | 0.01 | 0.01264 | 0.01267 | 0.01265 | 0.2 | 0.005822 | 0.005967 | 0.005722 |
| mcl | 0.2 | 0.2123 | 0.2125 | 0.2123 | 1 | 0.1584 | 0.15843 | 0.1585 |
| | 0.04 | 0.1675 | 0.1677 | 0.1671 | 0.2 | 0.1223 | 0.122235 | 0.12219 |
| | 0.01 | 0.08427 | 0.0843 | 0.08431 | 0.04 | 0.06058 | 0.06029 | 0.05985 |
| | 0.002 | 0.02277 | 0.02381 | 0.02265 | | | | |
| mma | 0.2 | 0.1761 | 0.1758 | 0.176 | 1 | 0.1533 | 0.15328 | 0.1528 |
| | 0.04 | 0.08012 | 0.08006 | 0.08009 | 0.2 | 0.05835 | 0.058477 | 0.05859 |
| | 0.01 | 0.02921 | 0.02805 | 0.02788 | 0.04 | 0.01326 | 0.013576 | 0.01398 |
| mpd | 0.2 | 0.1506 | 0.1505 | 0.1506 | 5 | 0.05141 | 0.051406 | 0.05155 |
| | 0.04 | 0.1211 | 0.1213 | 0.121 | 1 | 0.04713 | 0.04701 | 0.04689 |
| | 0.01 | 0.06401 | 0.0638 | 0.06377 | 0.2 | 0.03262 | 0.032519 | 0.0325 |
| | | | | | 0.04 | 0.01369 | 0.013523 | 0.01403 |
| nmr | 1 | 0.1521 | 0.1522 | 0.153 | 1 | 0.1089 | 0.108355 | 0.1085 |
| | 0.2 | 0.06788 | 0.06784 | 0.06777 | 0.2 | 0.03637 | 0.03629 | 0.03625 |
| | 0.04 | 0.01691 | 0.01687 | 0.0168 | 0.04 | 0.007781 | 0.00767 | 0.007932 |
| sce | 0.2 | 0.11 | 0.1103 | 0.1103 | 5 | 0.09422 | 0.094105 | 0.09418 |
| | 0.04 | 0.05257 | 0.05264 | 0.05265 | 1 | 0.070325 | 0.070222 | 0.070198 |
| | 0.01 | 0.01813 | 0.01981 | 0.01853 | 0.2 | 0.030413 | 0.030402 | 0.03229 |

Activity was indicated by dABS/min when 10 μl of each enzyme was added to 1 ml of reaction solution.

TABLE 10

Km and $k_{cat}$ of each mevalonate kinase

| | Km app. for mevalonate (μM) | Km app. for ATP (μM) | Vmax (dABS/min) | Molecular Weight (Da) | enzyme concentration (mg/ml) | $k_{cat}$ ($S^{-1}$) | $k_{cat}$/Km app. for mevalonate (μM/S) |
|---|---|---|---|---|---|---|---|
| cva | 74 ± 0.2 | 1347 ± 29 | 0.106 ± 0.001 | 32746 | 0.25 | 3.7 ± 0.003 | 0.050 |
| mcl | 17 ± 0.5 | 74 ± 1.4 | 0.232 ± 0.002 | 35626 | 0.16 | 14 ± 0.11 | 0.824 |
| mma | 83 ± 1.9 | 687 ± 9.3 | 0.249 ± 0.002 | 33575 | 0.115 | 19 ± 0.16 | 0.229 |
| mpd | 15 ± 0.51 | 119 ± 2.1 | 0.163 ± 0.001 | 33908 | 0.204 | 7.3 ± 0.04 | 0.487 |
| nmr | 461 ± 7.5 | 1006 ± 20 | 0.223 ± 0.002 | 36594 | 0.176 | 12 ± 0.11 | 0.026 |
| sce | 73 ± 1.6 | 464 ± 7.6 | 0.1506 ± 0.001 | 50622 | 0.127 | 16 ± 0.11 | 0.219 |

6.22 $mM^{-1}$ $cm^{-1}$ was used as millimolar absorbance coefficient of NADH 4.6 Confirmation of the Inhibition of Each Enzyme by DMAPP, GPP, FPP or DPM Inhibition of mevalonate kinase by terpenyl diphosphate or intermediates of mevalonate pathway was confirmed as follows: Dimethylallyl diphosphate ammonium salt (DMAPP: 5 mM) (Cayman, 63180), geranyl phyrophosphate ammonium salt (GPP: 0.1 mM) (SIGMA, 6772-5VL), farnesyl pyrophosphate ammonium salt (FPP: 0.1 mM) (SIGMA, F6892-5VL) or (±)-mevalonic acid 5-diphosphate tetralithium salt (DPM: 1 mM) (SIGMA, 94259-10MG) were separately mixed in the reaction solution consisting of 50 mM Tris-HCl, 0.4 mM PEP, 0.33 mM NADH, 10 mM MgCl$_2$, 0.05 mM DTT, 50 mM NaCl, LDH (20 U/ml), PK (20 U/ml), 5 mM potassium mevalonate and 5 mM ATP to measure enzyme activity. Since GPP and FPP solutions contain methanol, methanol which was needed to keep the same methanol level at the addition to the reaction system was added to the reaction solution, which was designated as control.

Figure 15:
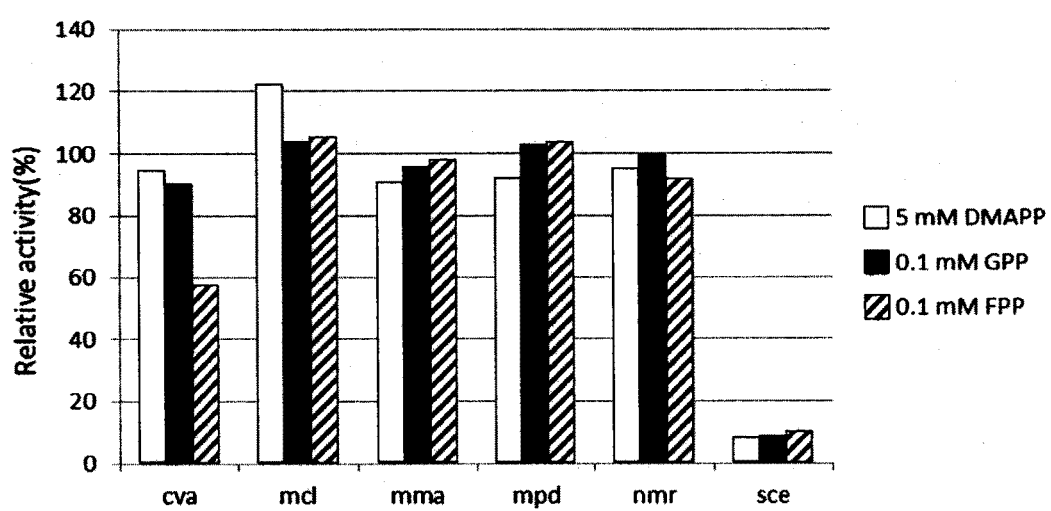
FIG. 15 is a graph showing respective effects of DMAPP, GPP, and FPP on the activity of each enzyme; relative activity of each enzyme when enzyme activity without terpenyldiphosphate was designated as 100%.

Respective effect of the added 5 mM DMAPP, 0.1 mM GPP, and 0.1 mM FPP on the activity of each enzyme was measured. Table 11 presents the activity of each enzyme (dABS/min) and FIG. 15 shows activity relative to the control. Every one of the three terpenyl diphosphates strongly inhibited sce-derived enzyme. Though FPP inhibited cva-derived enzyme, no other enzymes were inhibited strongly by FPP. Contrarily, mcl-derived enzyme was activated by 5 mM DMAPP and its activity increased by 20% from that of the control.

TABLE 11

Respective effects of DMAPP, GPP, and FPP on the activity of each enzyme

| | 5 mM DMAPP | 0.1 mM GPP | 0.1 mM FPP | Control |
|---|---|---|---|---|
| Cva | 0.0786 | 0.07532 | 0.04775 | 0.08338 |
| Mcl | 0.1806 | 0.1538 | 0.1562 | 0.1482 |
| Mma | 0.1904 | 0.20095 | 0.2059 | 0.21 |
| Mpd | 0.15282 | 0.1589 | 0.15943 | 0.15734 |
| Nmr | 0.231 | 0.24275 | 0.22405 | 0.2438 |
| Sce | 0.01102 | 0.01197 | 0.01398 | 0.1365 |

Figure 16:
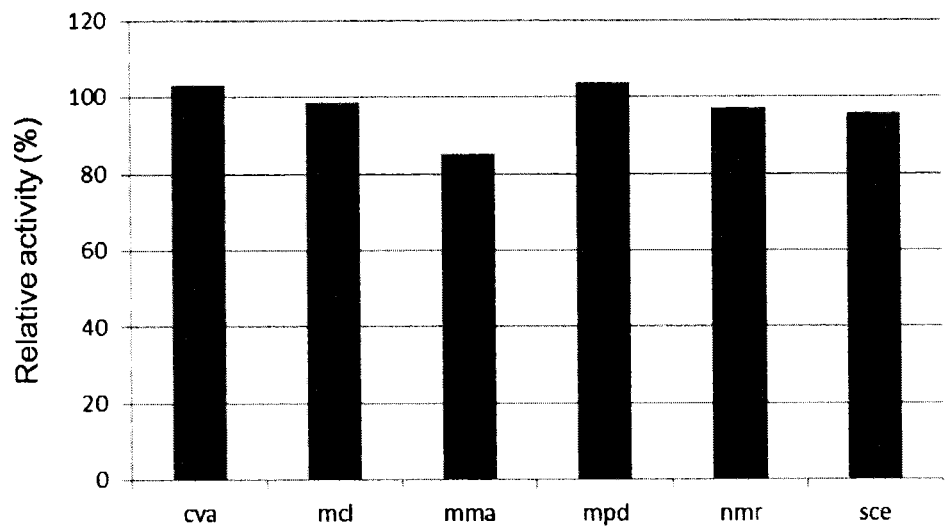
FIG. 16 is a graph showing effects of DPM on the activity of each MVK; enzyme activity was measured by adding 1 mM DPM to the reaction solution; activity without DPM measured in the same manner was used as control to present relative activity.

Activity when 10 μl of each enzyme was added to 1 ml of the reaction system was represented by dABS/min Effect of 1 mM diphosphomevalonate (DPM) on each enzyme was also studied. Slight inhibitory activity was confirmed only mma-derived enzyme (Table 12 and FIG. 16).

TABLE 12

Effect of DPM on the activity of each MVK

|     | Control  | 1 mM DPM |
| --- | -------- | -------- |
| cva | 0.073275 | 0.07555  |
| mcl | 0.1373   | 0.1353   |
| mma | 0.1604   | 0.1368   |
| mpd | 0.148    | 0.15604  |
| Nmr | 0.2064   | 0.2      |
| sce | 0.1028   | 0.0984   |

Activity when 10 µl of each enzyme was added to 1 ml of the reaction system was represented by dABS/min 4.7 Effect of Isopentenyl Diphosphate (IPP) on Mcl-derived Mevalonate Kinase Activity Isopentenyl pyrophosphate tri-ammonium salt solution (SIGMA, I0503-1VL) was used as IPP. IPP was added to the reaction solution (50 mM Tris-HCl, 0.4 mM PEP, 0.33 mM NADH, 10 mM MgCl$_2$, 0.05 mM DTT, 50 mM NaCl, LDH (20 U/ml), PK (20 U/ml)) to final concentrations of 33.6 µM and 168 µM to measure mevalonate kinase activity. Since IPP solution contained 70% methanol solution, the same quantity of 70% methanol solution was added to the reaction system as a control. Since 5 mM DMAPP was confirmed to increase activity, its effect on mcl-derived mevalonate kinase activity at 33.6 µM and 168 µM was examined.

Figure 17:
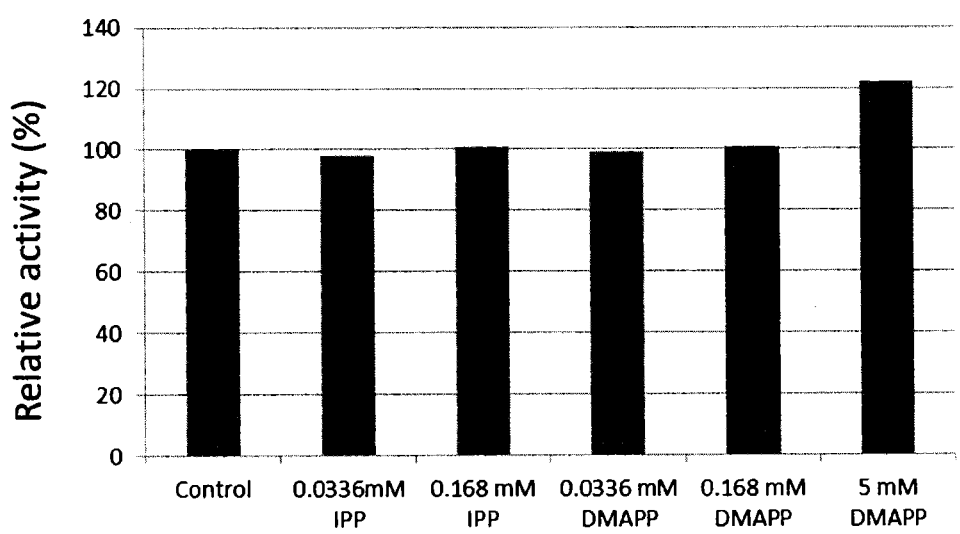
FIG. 17 is a graph showing influence of the respective addition of IP and DMAPP on mcl-derived enzyme activity.

Effect of IPP on mcl-derived enzyme which activity was confirmed to increase by DMAPP addition was examined (Table 13). FIG. 17 presents the relative activity when the control was designated as 100. Relative activities when the same concentrations of DMAPP and high-concentration (5 mM) DMAPP were separately added were measured simultaneously. Neither IPP nor DMAPP affected the enzyme activity at 33.6 µM and 168 µM. Addition of 5 mM DMAPP increased relative activity by 20%.

TABLE 13

Influence of low-concentration IPP and DMAPP on mcl-derived enzyme activity

|                         | dABS/min |
| ----------------------- | -------- |
| Control (MeOH)          | 0.15939  |
| 33.6 µM IPP             | 0.15795  |
| 168 µM IPP              | 0.16056  |
| Control (H$_2$O)        | 0.15403  |
| 33.6 µM DMAPP           | 0.15271  |
| 168 µM DMAPP            | 0.15515  |

4.8 Examination of Product Inhibition on Each Mevalonate Kinase

Preparation of Phosphomevalonate Kinase (PMK)

An ERG8 gene (NCBI Reference Sequence: NM_001182727.1) encoding the phosphomevalonate kinase in Saccharomyces cerevisiae was amplified by PCR performed with PrimeSTAR MAX Premix (supplied from TAKARA Bio) using synthetic oligonucleotides consisting of the nucleotide sequence of PMK-IFS_5742-33-3 (SEQ ID NO:122) and PMK-IFA_5742-33-4 (SEQ ID NO:123) as the primers with genomic DNA from *Saccharomyces cerevisiae* as the template. A reaction solution was prepared according to the composition attached to the kit, and the reaction at 98° C. for 10 seconds, 55° C. for 5 seconds and 72° C. for 5 seconds per kb was performed in 30 cycles. As a result, PCR products containing an ERG8 gene was obtained. A plasmid pSTV28-Ptac-Ttrp was digested with SmaI according to a standard method. Then, pSTV28-Ptac-Ttrp after being digested with SmaI was ligated to the PCR product containing an ERG8 gene by In-Fusion HD Cloning Kit (Supplied from Clontech). The obtained plasmid was designated as pSTV-Ptac-PMK-Ttrp.

PMK-IFS_5742-33-3 (SEQ ID NO:122)
5'-ACACAAGGAGACTCCCATGTCAGAGTT-GAGAGCCTTCA-3'
PMK-IFA_5742-33-4 (SEQ ID NO:123)
5'-GGAACTGGCGGCTCCCGGGTTATTATTTAT-CAAGATAAGTTTCCGG-3'

PMK-coding DNA was prepared by PCR using PMK-coding plasmid pSTV-Ptac-PMK-Ttrp as a template and oligonucleotide (5'-TCAGAGTTGAGAGCCTTCAGTGC-CCCAG-3' (SEQ ID NO:124) and 5'-GGAATTCTCTTTAT-CAAGATAAGTTTCCGGATCTTTTT-3' (SEQ ID NO:125)) as primers. Obtained DNA fragments were digested by EcoRI and cloned in pET21d. After NcoI digestion, pET21d underwent smoothing and then further digested with EcoRI to use for cloning. Inserted DNA sequence was confirmed by DNA sequencing. *E. coli* BL21 (DE3) was transformed with the obtained plasmid and cultured in 20 ml of LB medium at 30° C. by reciprocal shaking (140 rpm, TAITEC reciprocal shaker). When OD600=approx. 0.7, IPTG was added so that the final concentration is 0.1 mM. Then the mixture was cultured overnight under the same condition. Harvested cells were suspended in buffer solution A (50 mM sodium phosphate, 0.3 M NaCl, 20 mM Imidazol) and disrupted with an ultrasonic disruptor (TOMY: UD-201). Ultrasonic disruption was accomplished at output level=3.5. After centrifugation, resultant supernatant was adsorbed onto His-spin Trap (GE Healthcare) and the adsorbed proteins were eluted with an eluting solution, buffer solution A with imidazole concentration of 0.5 M. Eluate was dialyzed by using 20 mM Tris-HCl(pH8.0) containing 50 mM NaCl as external solution and then designated as purified enzyme.

Examination of Product Inhibition on Mevalonate Kinase

Enzyme was added to the reaction solution (100 mM Tris-HCl (pH7.6), 100 mM NaCl, 1 mM DTT, 10 mM MgCl$_2$, 50 mM ATP, 2.5 mM NADH, 40 mM PEP, LDH (20 U/ml), PK (20 U/ml), 1 mM mevalonate), and decrease in absorbance at 386 nm was measured. When decrease in absorbance stopped, purified PMK was added to measure further decrease in absorbance at 386 nm.

Figure 18:
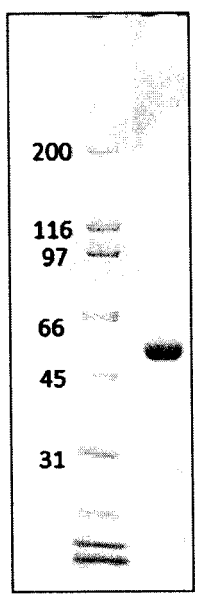
FIG. 18 is a rendering of SDS-PAGE of purified PMK; 5 µg of protein was loaded on 5 to 20% gel.
Figure 19:
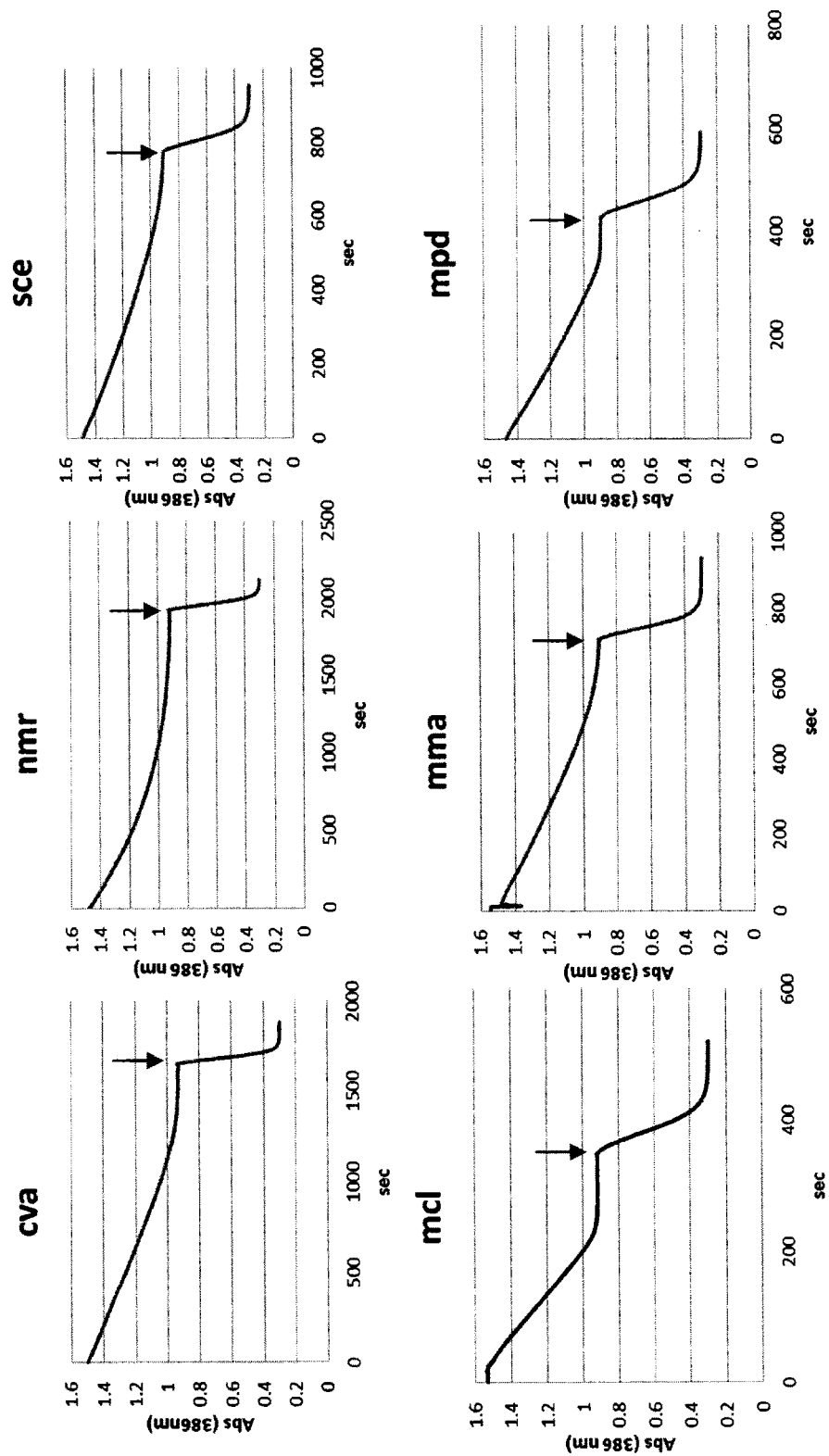
FIG. 19 includes graphs showing examination of product inhibition on each MVK; enzyme was added to the reaction solution and then decrease in absorbance at 386 nm was plotted; purified PMK was added at the points indicated by arrows; conversion of phosphomevalonate produced by MVK into diphosphomevalonate was confirmed by absorbance at 386 nm.

FIG. 18 presents the SDS-PAGE profile of the purified PMK. In order to examine possible product inhibition on each enzyme, decrease in absorbance at 386 nm resulting from the enzyme reaction using 1 mM mevalonate as a substrate was measured (FIG. 19). When 0.61 mM$^{-1}$ cm$^{-1}$ was designated as millimolar absorption coefficient of NADH at 386 nm, decrease in absorbance comparable to the substrate concentration (1 mM) (1.5-0.9=0.6) was observed in all enzymes. PMK was further added when mevalonate was depleted (or when absorbance stopped decreasing). Then, absorbance decreased further and finally absorbance at 386 nm decreased to 0.3 in all reaction systems. Therefore, it is inferred that mevalonate is converted into diphosphomevalonate via phosphomevalonate by adding PMK to each MVK. In the reactions of cva-, sce-, mcl-, mma- and mpd-derived MVK, almost linear decrease in absorbance was observed until PMK addition. Meanwhile, nmr-derived enzyme showed decrease in the rate of reaction associated with the progression of reaction (accumulation of the product). It suggests that DPM-induced inhibition is not observed in nmr-derived enzyme, but phosphomevalonate may cause product inhibition on nmr-derived enzyme.

Example 5

Production of Polyisoprene

Isoprene is collected with a trap cooled with liquid nitrogen by passing the fermentation exhaust. Collected of isoprene is mixed with 35 g of hexane (Sigma-Aldrich, catalog No. 296090) and 10 g of silica gel (Sigma-Aldrich, catalog No. 236772) and 10 g of alumina (Sigma-Aldrich, catalog No. 267740) under a nitrogen atmosphere in 100 mL glass vessel that is sufficiently dried. Resulting mixture is left at room temperature for 5 hours. Then supernatant liquid is skimmed and is added into 50 ml glass vessel that is sufficiently dried.

Meanwhile, in a glove box under a nitrogen atmosphere, 40.0 µmol of Tris[bis(trimethylsilyl)amido]gadolinium, 150.0 µmol of tributylaluminium, 40.0 µmol of Bis[2-(diphenylphosphino)phenyl]amine, 40.0 µmol of triphenylcarbonium tetrakis(pentafluorophenyl)borate (($Ph_3CBC_6F_5)_4$) are provided in a glass container, which was dissolved into 5 mL of toluene (Sigma-Aldrich, catalog No. 245511), to thereby obtain a catalyst solution. After that, the catalyst solution is taken out from the glove box and added to the monomer solution, which is then subjected to polymerization at 50° C. for 120 minutes.

After the polymerization, 1 mL of an isopropanol solution containing, by 5 mass %, 2,2'-methylene-bis(4-ethyl-6-t-butylphenol) (NS-5), is added to stop the reaction. Then, a large amount of methanol is further added to isolate the polymer, and the polymer is vacuum dried at 70° C. to obtain a polymer.

Example 6

Production of Rubber Compound

The rubber compositions formulated as shown in Table 14 are prepared, which are vulcanized at 145° C. for 35 minutes.

TABLE 14

| Rubber compositions of Example 6 | |
| --- | --- |
|  | Parts by mass |
| Polyisoprene | 100 |
| Stearic Acid | 2 |
| Carbon Black (HAF class) | 50 |
| Antioxidant (*1) | 1 |
| Zinc Oxide | 3 |
| Cure Accelerator (*2) | 0.5 |
| Sulfur | 1.5 |

(*1) N-(1,3-dimethylbutyl)-N'-p-phenylenediamine
(*2) N-cyclohexyl-2-benzothiazolesulfenamide Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A host cell, comprising a first heterogeneous expression unit and a second heterogeneous expression unit, wherein:
   the first heterogenous expression unit comprises:
   (a1) a polynucleotide encoding a mevalonate kinase derived from a microorganism belonging to a genus selected from the group consisting of *Methanocella, Corynebacterium, Methanosaeta*, and *Nitrosopumilus*; and
   (b1) a promoter operatively linked to the polynucleotide; and
   the second heterogenous expression unit comprises:
   (a2) polynucleotide encoding an enzyme involved in a methylerythritol phosphate pathway; and
   (b2) a promoter operatively linked to the polynucleotide.

2. The host cell according to claim 1; wherein the mevalonate kinase comprises an amino acid sequence having 70% or greater identity with an amino acid sequence selected from the group consisting of SEQ ID NO:1, SEQ ID NO:3, SEQ ID NO:6, and SEQ ID NO:9.

3. The host cell according to claim 1, wherein the host cell is a microorganism belonging to the family *Enterobacteriaceae*.

4. The host cell according to claim 3, wherein the host cell is a microorganism belonging to the genus *Eycherichia*.

5. The host cell according to claim 4, wherein the host cell is *Escherichia coli*.

6. The host cell according to claim 3, wherein the host cell is a microorganism belonging to the genus *Pantoea*.

7. The host cell according to claim 6, wherein the host cell is *Pantoea ananatis*.

8. The host cell according to claim 1, wherein the host cell comprises a genomic region in which a crt operon is disrupted.

9. The host cell according to claim 1, comprising a third heterogenous expression unit, the third heterogenous expression unit comprising:
   (a3) a polynucleotide encoding an isoprene synthase; and
   (b3) a promoter operatively linked to the polynucleotide.

10. A method of producing a mevalonate kinase, comprising:
    culturing the host cell according to claim 1; and
    extracting or purifying the mevalonate kinase from the culture.

11. A method of producing mevalonate-5-phosphate, comprising:
    culturing the host cell according to claim 1 in the presence of mevalonic acid or a precursor to mevalonic acid; and
    extracting or purifying mevalonate-5-phosphate from the culture.

12. A method of producing an isoprenoid compound, comprising:
    culturing the host cell according to claim 1; and
    extracting or purifying the isoprenoid compound from the culture.

13. The method of claim 12, wherein the isoprenoid compound is an isoprene monomer.

14. A method of producing an isoprene polymer, comprising:
    preparing an isoprene monomer by the method according to claim 12; and
    polymerizing the isoprene monomer to form the isoprene polymer.

15. A method for producing a rubber composition, comprising:
    (A) preparing an isoprene polymer by the method of claim 14; and
    (B) mixing the isoprene polymer with one or more rubber composition components.

16. A method for producing a tire, comprising:
    (i) producing a rubber composition by the method of claim 15; and
    (ii) applying the rubber composition to manufacture a tire.

17. A host cell, comprising a first heterogeneous expression unit and a second heterogeneous expression unit, wherein:
    the first heterogenous expression unit comprises:
    (a1) a polynucleotide encoding a mevalonate kinase derived from a microorganism belonging to a genus selected from the group consisting of *Methanocella, Corynebacterium, Methanosaeta*, and *Nitrosopumilus*; and
    (b1) a promoter operatively linked to the polynucleotide;
    the second heterogenous expression unit comprises:
    (a2) a polynucleotide encoding an enzyme involved in a mevalonate pathway; and
    (b2) a promoter operatively linked to the polynucleotide.

18. The host cell according to claim 17, wherein the mevalonate kinase comprises an amino acid sequence having 70% or greater identity with an amino acid sequence selected from the group consisting of SEQ ID NO:1, SEQ ID NO:3, SEQ ID NO:6, and SEQ ID NO:9.

19. The host cell according to claim 17, wherein the host cell is a microorganism belonging to the family *Enterobacteriaceae*.

20. The host cell according to claim 19, wherein the host cell is a microorganism belonging to the genus *Escherichia*.

21. The host cell according to claim 20, wherein the host cell is *Escherichia coli*.

22. The host cell according to claim 19, wherein the host cell is a microorganism belonging to the genus *Pantoea*.

23. The host cell according to claim 22, wherein the host cell is *Pantoea ananatis*.

24. The host cell according to claim 17, wherein the host cell comprises a genomic region in which a crt operon is disrupted.

25. The host cell according to claim 17, comprising a third heterogenous expression unit, the third heterogenous expression unit comprising:
    (a3) a polynucleotide encoding an isoprene synthase; and
    (b3) a promoter operatively linked to the polynucleotide.

26. A method of producing a mevalonate kinase, comprising:
   culturing the host cell according to claim 17; and
   extracting or purifying the mevalonate kinase from the culture.

27. A method of producing mevalonate-5-phosphate, comprising:
   culturing the host cell according to claim 17 in the presence of mevalonic acid or a precursor to mevalonic acid; and
   extracting or purifying mevalonate-5-phosphate from the culture.

28. A method of producing an isoprenoid compound, comprising:
   culturing the host cell according to claim 17; and
   extracting or purifying the isoprenoid compound from the culture.

29. The method of claim 28, wherein the isoprenoid compound is an isoprene monomer.

30. A method of producing an isoprene polymer, comprising:
   preparing an isoprene monomer by the method according to claim 28; and
   polymerizing the isoprene monomer to form the isoprene polymer.

31. A method for producing a rubber composition, comprising:
   (A) preparing an isoprene polymer by the method of claim 30; and
   (B) mixing the isoprene polymer with one or more rubber composition components.

32. A method for producing a tire, comprising:
   (i) producing a rubber composition by the method of claim 31; and
   (ii) applying the rubber composition to manufacture a tire.

* * * * *

SEQUENCE LISTING

```
<160> NUMBER OF SEQ ID NOS: 125

<210> SEQ ID NO 1
<211> LENGTH: 299
<212> TYPE: PRT
<213> ORGANISM: Methanocella paludicola

<400> SEQUENCE: 1

Met Thr Met Cys Ser Ala Pro Gly Lys Val Phe Leu Phe Gly Glu His
1               5                   10                  15

Ala Val Val Tyr Gly Lys Arg Ala Ile Ala Cys Ala Ile Asp Leu Arg
            20                  25                  30

Thr Thr Val Glu Val Ser Arg Lys Ser Arg Gly Val His Ile His Ser
        35                  40                  45

Ala Phe Lys Asp Glu Pro Asp Lys Asn Leu Tyr Ile Lys Thr Ala Val
    50                  55                  60

Lys Arg Met Gln Lys Cys Ala Asp Ile Arg Asn Val Asn Ile Ala Val
65                  70                  75                  80

Ser Ser Arg Ile Pro Val Ala Ser Gly Leu Gly Ser Ser Ala Ala Val
                85                  90                  95

Thr Val Ala Thr Ile Gly Ala Leu Asn Glu Glu Phe Ser Ala Gly Leu
            100                 105                 110

Ser Lys Lys Asp Ile Ala Tyr Met Ala Tyr Gln Thr Glu Leu Glu Val
        115                 120                 125

Gln Gly Ala Ala Ser Pro Thr Asp Thr Phe Val Ser Thr Met Gly Gly
    130                 135                 140
```

```
Thr Val Val Pro Asp Met Arg Thr Leu Pro Pro Ile Thr Cys Gly
145                 150                 155                 160

Ile Val Val Gly His Thr Gly Ile Ser Lys Ser Thr Ser Arg Met Val
                165                 170                 175

Ser Arg Val Arg Thr Leu Lys Glu Lys Tyr Pro Asp Val Ile Asp Gly
            180                 185                 190

Ile Met Asp Ser Ile Gly Asp Ile Ser Ala Arg Gly Glu Asp Leu Ile
            195                 200                 205

Lys Gln Asn Asp Tyr Arg Ser Ile Gly Glu Leu Met Asn Val Asn Gln
        210                 215                 220

Gly Leu Leu Asp Ala Leu Gly Ile Thr Ile Pro Glu Leu Ser Leu Gln
225                 230                 235                 240

Ile Tyr Ala Ala Arg Gln His Gly Ala Tyr Gly Ala Lys Ile Thr Gly
                245                 250                 255

Ala Gly Gly Gly Cys Met Val Ala Ile Cys Asp Asp Lys Asn Cys
            260                 265                 270

Lys Glu Ile Ala Thr Ala Ile Gly Arg Ser Tyr Gly Asp Ser Phe Ile
        275                 280                 285

Ser Lys Pro Thr Ala Glu Gly Ile Phe Ile Gln
        290                 295

<210> SEQ ID NO 2
<211> LENGTH: 900
<212> TYPE: DNA
<213> ORGANISM: Methanocella paludicola

<400> SEQUENCE: 2
atgacgatgt gttcagcccc cggtaaggtc ttttattcg gcgagcatgc ggtcgtttac      60
ggcaagcgcg cgatcgcatg cgccatcgac ctgcggacca ccgtggaggt atcccgtaaa    120
agccgtggcg tccacattca ctcggccttc aaggacgagc cggataagaa cctgtatatc    180
aagacggccg ttaaaaggat gcagaagtgt gcggatatcc ggaacgtgaa catcgctgtt    240
tcctcgagga tccccgtggc ttcgggcctg ggctcctcgg ctgccgtgac cgtcgccacc    300
atcggcgcct tgaacgagga gttcagcgcc ggcttgagta aaaaagacat cgcgtatatg    360
gcctaccaga cagagctgga agtgcaggga gcggcgagcc cgaccgatac gttcgtgtcc    420
accatgggcg ggaccgttgt cgtgcccgac atgaggacac tgccgcctat cacctgcggc    480
atcgtggtcg gccacaccgg catatcaaaa tccacttcac gcatggtatc ccgggtgaga    540
acgctcaaag aaaaatcccc ggacgtcatc gacggcatca tggactcgat cggggatatc    600
tccgcgcggg gcgaggattt aataaaacag aacgactatc gttccatagg cgagctcatg    660
aacgtcaacc aggggctgct ggacgccctg ggcatcacca tcccgagct ctcactccag    720 atatatgccg cacgccagca cggcgcctac ggcgccaaga tcaccggcgc gggcggaggg    780
ggatgcatgg tggccatatg cgatgacaaa aattgtaaag atcgcgac cgccatcggg    840 cgctcatacg gcgacagctt catcagcaag ccaacggcgg agggaatatt catccaatga    900

<210> SEQ ID NO 3
<211> LENGTH: 319
<212> TYPE: PRT
<213> ORGANISM: Corynebacterium variabile

<400> SEQUENCE: 3

Met Ala Pro His Val Gly His Gly Gln Thr Val Ala Lys Ile Ile Leu
1               5                   10                  15
```

Phe Gly Glu His Ser Val Val Tyr Gly His Pro Ala Ile Ala Met Pro
                 20                  25                  30

Leu Arg Thr Leu Arg Met Ile Ala Arg Val Glu Pro Thr Asp Gly Pro
             35                  40                  45

Gly Thr Leu Ser Gly Leu Gly Trp Thr Gly Pro Ile Thr Glu Ala Pro
         50                  55                  60

Ala Arg Phe Ser Ser Ile Val Lys Ala Ala Glu Val Ala Ser Asp Phe
65                  70                  75                  80

Ala Gly His Pro Gly Ala Gly Leu Asn Ile Ser Thr Glu Ser Glu Phe
                 85                  90                  95

Pro Pro Glu Arg Gly Leu Gly Ser Ala Ala Ala Gly Ala Val
                100                 105                 110

Ile Arg Ala Val Leu Asp Ala Phe Asp Thr Pro Ala Thr Pro Arg Glu
             115                 120                 125

Leu Phe Asp Leu Thr Gln Glu Ala Glu Thr Val Ala His Gly Arg Pro
130                 135                 140

Ser Gly Leu Asp Ala Val Ala Thr Ser Ala Glu Ala Pro Val His Phe
145                 150                 155                 160

Gln Ala Gly Gln Ala Thr Asp Leu Glu Phe Ser Pro Asp Ala Trp Ile
                165                 170                 175

Val Ile Ala Asp Ser Gly Val Glu Gly Ser Thr Arg Glu Thr Val Gly
             180                 185                 190

His Val Arg Gly Arg Phe Glu Ala Glu Pro Asp Ile Ile Thr Ala Leu
         195                 200                 205

Leu Asn Arg Leu Gly Glu Ile Thr Asp Glu Val Val Val Asp Leu Arg
     210                 215                 220

Thr Gly Asp Val Gln Gly Met Gly Ala Arg Met Thr Glu Ala His Gly
225                 230                 235                 240

Ile Leu Gly Gln Leu Gly Val Ser Asn Thr Gln Leu Asp Ala Leu Val
                245                 250                 255

Thr Ala Ser Leu Gly Ala Gly Ala Leu Gly Ala Lys Leu Thr Gly Gly
             260                 265                 270

Gly Arg Gly Gly Cys Val Ile Ala Leu Ala Ala Thr Glu Glu Asp Ala
         275                 280                 285

Glu Asn Val Glu Lys Ala Leu Val Asp Ala Gly Ala Arg Gly Thr Trp
     290                 295                 300

Val His Ala Pro Ala Thr Gly Gln Met Ala Gly Glu Val Met Gln
305                 310                 315

<210> SEQ ID NO 4
<211> LENGTH: 960
<212> TYPE: DNA
<213> ORGANISM: Corynebacterium variabile

<400> SEQUENCE: 4
gtggcacctc acgtcggaca cggccagacc gtggccaaga tcatccttt cggggagcat        60 tccgtggtct acgggcaccc cgctatcgcg atgccgctgc gcacgctgcg catgatcgcg       120
cgcgtcgagc ccaccgacgg tccaggcacc ctctccggcc tgggctggac cggtcccatc       180
actgaggctc cggccaggtt ctccagcatc gtcaaagccg cggaggtcgc ctccgacttc       240
gccggtcacc ccggcgccgg cctgaacatc tccaccgaat ccgagttccc cccggagcgc       300
ggtctcggtt cgtccgccgc cgccgccggt gcagtcatcc gtgcggtgct cgacgccttc       360
gacacacccg ccactccgcg cgagctcttc gatctcaccc aggaagccga gacagtcgcc       420

-continued

```
cacgggcgtc cctccgggct ggatgccgtc gccacatcgg cggaggcacc ggtccacttc      480
caggcgggtc aggccacgga cctggagttc agcccggacg cctggatcgt catcgccgat      540
tccggtgtcg aaggctccac gcgggagacc gtgggacacg tccgtggccg cttcgaggct      600
gagccggaca tcatcacggc actgctcaac cggctcggcg agatcaccga cgaagtcgtc      660
gtcgatctgc gcaccggtga cgtccagggc atgggtgccc ggatgaccga ggcgcacggc      720
atcctgggcc agctcggtgt cagcaacacc cagctggacg ccctggtcac cgcgtccctc      780
ggggcaggcg ccctgggggc gaagctcacc ggcggtggac gcggtggctg cgtcatcgcc      840
ctggcagcca ccgaagagga cgccgagaac gtcgagaagg cactggtgga cgccggtgcc      900
cggggaacct gggtccatgc ccccgccacc ggacagatgg ccggggaggt catgcagtga      960
```

<210> SEQ ID NO 5
<211> LENGTH: 960
<212> TYPE: DNA
<213> ORGANISM: Artificial Sequence
<220> FEATURE:
<223> OTHER INFORMATION: DNA having modified codons, which encodes
      mevalonate kinase derived from Corynebacterium variabile (Cvamvk)

<400> SEQUENCE: 5

```
atggccccgc acgtcggtca cggtcaaacg gtcgccaaaa tcattctgtt cggtgaacac       60
tctgtggtct acgtcatcc ggccatcgcg atgccgctgc gtaccctgcg catgattgcc      120
cgtgttgaac cgaccgatgg tccgggtacg ctgagcggtc tgggttggac cggtccgatt      180
acggaagcac cggcacgctt tagctctatc gttaaagcgg ccgaagtcgc atctgatttc      240
gctggtcatc cgggtgccgg cctgaacatt tcaaccgaat cggaatttcc gccggaacgt      300
ggtctgggta gttccgcagc tgcagcaggt gcagtcatcc gtgccgtgct ggatgcattt      360
gacaccccgg caacgccgcg tgaactgttc gacctgaccc aggaagctga acggtggca      420 catggtcgtc cgagtggtct ggatgcagtt gctacctccg cagaagcacc ggtccacttt      480
caggcaggtc aagccacgga cctggaattc tcaccggatg cttggattgt catcgcggac      540
agcggtgtgg aaggctctac ccgtgaaacg gtgggccatg ttcgtggtcg cttcgaagcc      600
gaaccggata ttatcaccgc actgctgaac cgcctgggcg aaattaccga tgaagtggtt      660
gtcgacctgc gtacgggtga tgttcagggt atgggcgccc gcatgaccga agcacacggt      720
atcctgggcc agctgggtgt gtcaaatacc caactggatg ccctggttac ggcatcgctg      780
ggtgcaggtg ctctgggtgc aaaactgacc ggcggtggcc gtggtggctg cgtgatcgcg      840
ctggcagcta cggaagaaga cgctgaaaat gtggaaaagg cgctggttga tgcaggtgca      900
cgtggtacct gggtccacgc accggctacg ggtcagatgg caggtgaagt gatgcaataa      960
```

<210> SEQ ID NO 6
<211> LENGTH: 317
<212> TYPE: PRT
<213> ORGANISM: Methanosaeta concilii

<400> SEQUENCE: 6

Met Thr Met Ala Ser Ala Pro Gly Lys Ile Ile Leu Phe Gly Glu His
1               5                   10                  15

Ala Val Val Ser Gly Thr Ala Ala Leu Gly Gly Ala Ile Asp Leu Arg
                20                  25                  30

Ala Arg Ala Ile Val Gln Ser Leu Pro Gly Arg Ile Leu Ile Glu Thr
        35                  40                  45

Asp Asp Leu Ser Leu Arg Gly Phe Ser Leu Asp Leu Ser Thr Gly Glu
            50                  55                  60

Ile Arg Ser Ala Ser Ala Ala Tyr Ala Thr Arg Tyr Val Ser Ala Val
65                  70                  75                  80

Leu Lys Glu Leu Gly Ala Arg Asp Val Arg Val Met Ile Glu Ser Asp
                85                  90                  95

Ile Pro Pro Ala Ala Gly Leu Gly Ser Ser Ala Ser Ile Val Val Ala
            100                 105                 110

Thr Val Ala Ala Leu Asn Gly His Leu Gly Leu Glu Leu Ser Gln Lys
            115                 120                 125

Glu Ile Ala Ala Leu Ser Tyr Arg Ile Glu Lys Glu Val Gln Lys Gly
130                 135                 140

Arg Gly Ser Pro Met Asp Thr Ala Leu Ala Thr Tyr Gly Gly Tyr Gln
145                 150                 155                 160

Arg Ile Ala Asp Asp Asn Gln Arg Leu Asp Leu Pro Pro Leu Glu Met
                165                 170                 175

Val Val Gly Tyr Thr Arg Leu Pro His Asp Thr Phe Ser Leu Val Glu
            180                 185                 190

Lys Val Gln Leu Leu Lys Glu Arg Tyr Pro Asp Leu Val Gly Pro Ile
            195                 200                 205

Phe Gln Ala Ile Gly Ala Ile Ser Glu Arg Ala Ala Pro Leu Ile Arg
            210                 215                 220

Glu Gln Arg Leu Lys Asp Leu Gly Leu Met Asp Ile Asn His Gly
225                 230                 235                 240

Leu Leu Glu Ala Leu Gly Val Gly Ser Arg Glu Leu Ser Glu Leu Val
                245                 250                 255

Tyr Ala Ala Arg Asn Thr Gly Gly Ala Leu Gly Ala Lys Leu Thr Gly
            260                 265                 270

Ala Gly Gly Gly Gly Cys Met Ile Ala Leu Pro Gly Met Ala Gly Lys
            275                 280                 285

Asp Ala Leu Leu Val Ala Leu Arg Gln Ala Arg Gly Met Ala Phe Ala
            290                 295                 300

Ala Met Met Gly Cys Glu Gly Val Arg Leu Glu Val Ala
305                 310                 315

<210> SEQ ID NO 7
<211> LENGTH: 954
<212> TYPE: DNA
<213> ORGANISM: Methanosaeta concilii

<400> SEQUENCE: 7

```
atgacgatgg catcggctcc cggcaaaatc atcctcttcg agagcatgc cgttgtctcc      60
ggcactgccg cattgggagg agccatagat ctgcgagcta gggctattgt gcagagcctg    120
ccgggaagga ttttgataga gactgacgac ctttcactac gaggttttc tctggatctc    180
tctaccgggg agatcaggtc agccagtgcg gcctatgcta ccagatatgt atcagctgtt    240
ttaaaggagc ttggtgcaag ggatgttagg gtcatgatcg agtcggacat cccgccggca    300
gcgggtctcg gatcatcggc gtccatagtg gttgccacgg tagctgctct aaacggtcac    360
ctgggcctga aattatcaca aaaagagatt gcagctctct cctaccgcat agagaaggag    420
gttcaaaagg ggagaggcag ccccatggat actgctctgg ccacatatgg cggctaccag    480
aggattgcag atgacaacca gcgtctcgat cttccacctt tagagatggt ggtgggatac    540
accagactgc ctcatgatac cttttccctg gtggagaagg tccagctctt aaaagagcgc    600
```

| | | | |
|---|---|---|---|
| tatccagacc | tggtgggtcc | catattccag | gccataggag | ccatatccga | gagggctgct | 660 |
| cctctgatcc | gagagcagag | actgaaagat | ctgggcgagc | tgatggacat | caaccatggc | 720 |
| ctcttggagg | ccctgggggt | gggctccaga | gagctgtccg | agctagtcta | tgcggcgagg | 780 |
| aataccggag | gagccttagg | ggccaagctg | acgggagcgg | gaggaggagg | atgcatgatc | 840 |
| gcccttcccg | ggatggccgg | aaaggatgca | ttattggtgg | ccttgaggca | ggccagagga | 900 |
| atggcatttg | cagctatgat | gggctgtgag | ggcgtccggc | tggaggttgc | gtga | 954 |

<210> SEQ ID NO 8
<211> LENGTH: 954
<212> TYPE: DNA
<213> ORGANISM: Artificial Sequence
<220> FEATURE:
<223> OTHER INFORMATION: DNA having modified codons, which encodes mevalonate kinase derived from Methanosaeta concilii (Mclmvk)

<400> SEQUENCE: 8

| | | | | | |
|---|---|---|---|---|---|
| atgacgatgg | cttccgctcc | gggcaagatt | attctgtttg | cgaacacgc | tgtggtctcg | 60 |
| ggcacggctg | ctctgggtgg | cgctattgat | ctgcgtgcac | gcgctattgt | gcagtcactg | 120 |
| ccgggccgta | ttctgatcga | aaccgatgac | ctgtcgctgc | gcggcttttc | actggacctg | 180 |
| tcgaccggtg | aaatccgtag | tgcttccgcg | gcctatgcga | cgcgctacgt | gtctgctgtt | 240 |
| ctgaaagaac | tgggtgcacg | tgatgttcgc | gtcatgattg | aaagcgacat | cccgccggca | 300 |
| gctggtctgg | gtagctctgc | ctctattgtg | gttgcaaccg | tcgcagcact | gaacggtcat | 360 |
| ctgggtctgg | aactgagtca | gaaggaaatt | gcagctctgt | cctatcgtat | cgaaaaagaa | 420 |
| gttcaaaagg | gtcgtggtag | cccgatggat | accgcactgg | ccacgtatgg | cggttaccag | 480 |
| cgtattgcgg | atgacaatca | acgcctggat | ctgccgccgc | tggaaatggt | cgtgggctat | 540 |
| acccgtctgc | cgcatgacac | gtttagtctg | gtcgaaaaag | tgcagctgct | gaaggaacgc | 600 |
| tacccggatc | tggtgggccc | gatcttccaa | gcaattggtg | ctatcagcga | acgtgcggcc | 660 |
| ccgctgattc | gtgaacagcg | cctgaaagat | ctgggcgaac | tgatggacat | caaccacggt | 720 |
| ctgctggaag | cactgggtgt | gggtagccgt | gaactgtctg | aactggttta | cgcagctcgt | 780 |
| aataccggcg | gtgcactggg | tgcaaaactg | acgggtgccg | cggtggcgg | ttgcatgatc | 840 |
| gcactgccgg | gcatggcagg | caaggatgct | ctgctggttg | cgctgcgtca | gcccgcggt | 900 |
| atggcattcg | cggccatgat | gggctgtgaa | ggtgttcgcc | tggaagtcgc | gtaa | 954 |

<210> SEQ ID NO 9
<211> LENGTH: 313
<212> TYPE: PRT
<213> ORGANISM: Nitrosopumilus maritimus

<400> SEQUENCE: 9

Met Lys Ser Lys Ala Ser Ala Pro Gly Lys Val Ile Leu Phe Gly Glu
1               5                   10                  15

His Phe Val Val Tyr Gly Val Lys Ala Ile Leu Cys Ala Ile Asn Lys
                20                  25                  30

Arg Ile Ala Val Thr Ala Glu Lys Ile Asp Glu Arg Lys Ile Ser Ile
            35                  40                  45

Lys Ser Asn Ile Gly His Leu Glu Leu Glu Pro Asn Lys Pro Ile Ser
        50                  55                  60

Glu Ile Asn Ser Pro Leu Lys Pro Phe Tyr Tyr Leu Ala Asn Lys Ile
65                  70                  75                  80

Ile Gln Asp Lys Asn Phe Gly Ile Lys Ile Asp Val Glu Ser Glu Ile

```
                        85                  90                  95
Pro Leu Gly Val Gly Leu Gly Ser Ser Ser Ala Cys Cys Val Ala Gly
            100                 105                 110

Ala Ala Ala Ile Ser Asn Leu Phe Glu Asn Asn Ser Lys Glu Glu Ile
            115                 120                 125

Leu Lys Leu Ala Ile Glu Ala Glu Lys Thr Ile Phe Gln Asn Thr Ser
    130                 135                 140

Gly Ala Asp Cys Thr Val Cys Thr Phe Gly Gly Leu Met Glu Tyr Asp
145                 150                 155                 160

Lys Glu Asn Gly Phe Ser Lys Ile Glu Ser Glu Pro Asn Phe His Leu
                165                 170                 175

Val Ile Ala Asn Ser Asn Val Glu His Ser Thr Glu Ser Val Val Ala
            180                 185                 190

Gly Val Arg Lys Phe Lys Lys Asn Asn Glu Ala Glu Phe Ser Lys Leu
        195                 200                 205

Cys Lys Asp Glu Ser His Leu Ile Glu Asn Val Leu Glu Leu Leu Lys
    210                 215                 220

Glu Asn Asn Ile Arg Glu Leu Gly Glu Arg Val Ile Lys Asn Gln Glu
225                 230                 235                 240

Tyr Leu Glu Arg Ile Gly Ile Ser Asn Ala Lys Leu Arg Glu Met Ile
                245                 250                 255

Gln Thr Gly Gln Asn Ser Ser Phe Gly Ala Lys Ile Thr Gly Ala Gly
            260                 265                 270

Gly Gly Gly Cys Ile Phe Ala Leu Thr Asp Glu Ser Asn Leu Glu Asn
        275                 280                 285

Thr Ile Lys Glu Phe Lys Glu Lys Asn His Glu Cys Phe Ser Val Lys
    290                 295                 300

Ile Asp Phe Lys Gly Leu Asp Thr Phe
305                 310

<210> SEQ ID NO 10
<211> LENGTH: 942
<212> TYPE: DNA
<213> ORGANISM: Nitrosopumilus maritimus

<400> SEQUENCE: 10
ttgaaatcta aagcctctgc tcctggaaaa gttattcttt ttggagaaca ttttgttgtg      60
tatggagtta aagcgattct tgtgcaatt aacaaaagaa tcgcagttac tgcagaaaaa     120
attgatgaaa gaaaatttc aatcaaatct aatattggtc accttgaatt agaaccaaac     180
aaaccaattt cagaaattaa ttcaccgcta aaaccatttt attatttggc aaataaaata     240
attcaagata aaattttggg aatcaagata gacgttgaat cagaaattcc attaggtgtt     300
ggtttaggtt catcatctgc ttgttgtgta gcaggagcag ctgcaatttc aaatctattt     360
gaaaataatt caaagaagaa gattctaaaa cttgcaatag aggcagaaaa aacaattttt     420
caaaacacat caggtgcaga ttgtacggtt tgcacttttg gaggattaat ggagtacgac     480
aaggaaaatg gttttccaa atagaatct gagcctaatt ttcatctagt tatagcaaat     540
tcaaatgttg aacattcaac agaaagtgtt gtggcaggag taagaaaatt caaaaaaaac     600
aatgaagcag aatttcaaa attatgtaaa gatgaatcac atcttattga aaatgtatta     660
gaattgttaa aagaaaataa cattagagaa cttggtgaga gagtaattaa gaatcaagag     720
tacttggaga gaattggaat ttcaaatgcc aaactcagag agatgattca aactggacaa     780
aattcatcat ttggtgcaaa aattacaggt gcaggaggag gaggatgtat tttgcccctt     840
```

```
acagatgaat caaatttaga aaatacgatc aagaattca agaaaaaaa tcacgaatgt    900 ttttctgtaa aaattgattt caaaggactg gatactttt aa                       942
```

<210> SEQ ID NO 11
<211> LENGTH: 942
<212> TYPE: DNA
<213> ORGANISM: Artificial Sequence
<220> FEATURE:
<223> OTHER INFORMATION: DNA having modified codons, which encodes
      mevalonate kinase derived from Nitrosopumilus maritimus (Nmrmvk)

<400> SEQUENCE: 11

```
atgaagagca aggcatctgc gccgggcaag gtcatcctgt tggtgaaca tttcgtggtc    60 tacggtgtca aggcaatcct gtgtgcgatt aacaagcgta tcgctgtgac cgcggaaaag   120
atcgatgaac gcaagatctc gatcaagagc aatatcggtc atctggaact ggaaccgaac   180
aagccgattt ccgaaatcaa ttcaccgctg aaaccgttct attacctggc gaacaagatc   240
atccaggata agaacttcgg tatcaagatc gacgttgaaa gcgaaattcc gctgggcgtc   300
ggtctgggca gctctagtgc ttgctgtgtc gcaggtgcag cagcaatctc taacctgttc   360
gaaaacaaca gtaaggaaga atcctgaag ctggccatcg aagcagaaaa aaccattttc    420
caaaatacgt ctggtgctga ttgcaccgtg tgtacgtttg cggtctgat ggaatatgac    480 aaggaaaacg gcttctcgaa aattgaaagc gaaccgaatt tcatctggt catcgccaac   540 agcaatgtgg aacactctac cgaaagtgtg gttgctggtg ttcgtaagtt caaaaagaac   600
aacgaagcga aattttccaa actgtgcaag gatgaatcac atctgattga aaacgtgctg   660
gaactgctga agaaaacaa tattcgtgaa ctgggcgaac gcgttatcaa aaaccaggaa   720
tacctggaac gtattggtat cagtaatgcc aaactgcgcg aatgattca gaccggccaa   780 aactcctcat tcggtgccaa aattacgggc gcaggcggtg gcggttgcat ctttgcactg   840
accgacgaat cgaacctgga aaacacgatc aaggaattca ggaaagaa tcacgaatgt    900 tttagcgtca aaatcgattt caagggcctg gacacgtttt aa                      942
```

<210> SEQ ID NO 12
<211> LENGTH: 301
<212> TYPE: PRT
<213> ORGANISM: Methanosarcina mazei

<400> SEQUENCE: 12

```
Met Val Ser Cys Ser Ala Pro Gly Lys Ile Tyr Leu Phe Gly Glu His
1               5                   10                  15

Ala Val Val Tyr Gly Glu Thr Ala Ile Ala Cys Ala Val Glu Leu Arg
                20                  25                  30

Thr Arg Val Arg Ala Glu Leu Asn Asp Ser Ile Thr Ile Gln Ser Gln
            35                  40                  45

Ile Gly Arg Thr Gly Leu Asp Phe Glu Lys His Pro Tyr Val Ser Ala
        50                  55                  60

Val Ile Glu Lys Met Arg Lys Ser Ile Pro Ile Asn Gly Val Phe Leu
65                  70                  75                  80

Thr Val Asp Ser Asp Ile Pro Val Gly Ser Gly Leu Gly Ser Ser Ala
                85                  90                  95

Ala Val Thr Ile Ala Ser Ile Gly Ala Leu Asn Glu Leu Phe Gly Phe
                100                 105                 110

Gly Leu Ser Leu Gln Glu Ile Ala Lys Leu Gly His Glu Ile Glu Ile
            115                 120                 125
```

Lys Val Gln Gly Ala Ala Ser Pro Thr Asp Thr Tyr Val Ser Thr Phe
    130                 135                 140

Gly Gly Val Val Thr Ile Pro Glu Arg Arg Lys Leu Lys Thr Pro Asp
145                 150                 155                 160

Cys Gly Ile Val Ile Gly Asp Thr Gly Val Phe Ser Ser Thr Lys Glu
                165                 170                 175

Leu Val Ala Asn Val Arg Gln Leu Arg Glu Ser Tyr Pro Asp Leu Ile
                180                 185                 190

Glu Pro Leu Met Thr Ser Ile Gly Lys Ile Ser Arg Ile Gly Glu Gln
        195                 200                 205

Leu Val Leu Ser Gly Asp Tyr Ala Ser Ile Gly Arg Leu Met Asn Val
210                 215                 220

Asn Gln Gly Leu Leu Asp Ala Leu Gly Val Asn Ile Leu Glu Leu Ser
225                 230                 235                 240

Gln Leu Ile Tyr Ser Ala Arg Ala Ala Gly Ala Phe Gly Ala Lys Ile
                245                 250                 255

Thr Gly Ala Gly Gly Gly Gly Cys Met Val Ala Leu Thr Ala Pro Glu
                260                 265                 270

Lys Cys Asn Gln Val Ala Glu Ala Val Ala Gly Ala Gly Gly Lys Val
            275                 280                 285

Thr Ile Thr Lys Pro Thr Glu Gln Gly Leu Lys Val Asp
    290                 295                 300

<210> SEQ ID NO 13
<211> LENGTH: 906
<212> TYPE: DNA
<213> ORGANISM: Methanosarcina mazei

<400> SEQUENCE: 13
atggtttcat gttctgcgcc cgggaaaatc tatcttttcg agaacatgc ggttgtttac       60
ggagaaaccg caatagcgtg tgcagtagag ttaaggaccc gggtgcgggc ggagttaaat     120
gactccataa ctatccagtc tcagatcggc aggacaggtc ttgattttga aaaacatccc     180
tatgtctctg cagtgattga aaaaatgaga aaatctatcc ccataaatgg tgtttttta     240
actgttgatt ccgacattcc tgttgggtca gggctcggct catctgctgc tgttacgatt   300
gcaagcatag gagctctcaa cgaacttttc ggattcgggc tttcgcttca ggaaattgcg    360
aaactggggc atgaaattga dataaaagtt cagggtgcag cgagccctac tgacacctat   420
gtttctactt tcggaggagt cgttaccatc cctgaaagga aaagcttaa gactcctgac    480
tgtggaattg ttataggga caccggagtt ttttcttcta caaagagct tgtggcaaac     540
gtcaggcagc tccgcgaaag ttaccctgat cttatcgaac ctcttatgac ttctattggc   600
aaaatctcca gaatcggtga gcaacttgta ctttccgggg actatgcttc tattggcagg   660
cttatgaatg taaatcaggg actgcttgat gcacttggag ttaatatcct tgagctttca   720
cagcttatct attctgcaag ggcagcagga gctttcgggg caaaaattac tggagcagga   780
ggcggtggtt gtatggttgc gctaactgca ccggagaaat gtaatcaggt agcggaagcc   840
gttgcaggtg caggggggcaa agtgaccatt acaaaaccca cggaacaggg gttgaaggtc   900
gattga                                                                 906

<210> SEQ ID NO 14
<211> LENGTH: 906
<212> TYPE: DNA
<213> ORGANISM: Artificial Sequence
<220> FEATURE:
<223> OTHER INFORMATION: DNA having modified codons, which encodes
     mevalonate kinase derived from Methanosarcina mazei (Mmamvk)

<400> SEQUENCE: 14

```
atggtatcct gttctgcgcc gggtaagatt tacctgttcg gtgaacacgc cgtagtttat      60
ggcgaaactg caattgcgtg tgcggtggaa ctgcgtaccc gtgttcgcgc ggaactcaat     120
gactctatca ctattcagag ccagatcggc cgcaccggtc tggatttcga aaagcaccct     180
tatgtgtctg cggtaattga aaaatgcgc aaatctattc ctattaacgg tgttttcttg     240
accgtcgatt ccgacatccc ggtgggctcc ggtctgggta gcagcgcagc cgttactatc     300
gcgtctattg gtgcgctgaa cgagctgttc ggctttggcc tcagcctgca agaaatcgct     360
aaactgggcc acgaaatcga attaaagta cagggtgccg cgtccccaac cgatacgtat     420
gtttctacct tcggcggcgt ggttaccatc ccggaacgtc gcaaactgaa actccggac     480
tgcggcattg tgattggcga taccggcgtt ttctcctcca ccaaagagtt agtagctaac     540
gtacgtcagc tgcgcgaaag ctacccggat ttgatcgaac cgctgatgac ctctattggc     600
aaaatctctc gtatcggcga caactggttc tgtctggcg actacgcatc catcggccgc     660
ctgatgaacg tcaaccaggg tctcctggac gccctgggcg ttaacatctt agaactgagc     720
cagctgatct attccgctcg tgcggcaggt gcgtttggcg ctaaaatcac gggcgctggc     780
ggcggtggct gtatggttgc gctgaccgct ccggaaaaat gcaaccaagt ggcagaagcg     840
gtagcaggcg ctggcggtaa agtgactatc actaaaccga ccgagcaagg tctgaaagta     900
gattaa                                                                 906
```

<210> SEQ ID NO 15
<211> LENGTH: 608
<212> TYPE: PRT
<213> ORGANISM: Pueraria montana var.lobata

<400> SEQUENCE: 15

```
Met Ala Thr Asn Leu Leu Cys Leu Ser Asn Lys Leu Ser Ser Pro Thr
1               5                   10                  15

Pro Thr Pro Ser Thr Arg Phe Pro Gln Ser Lys Asn Phe Ile Thr Gln
            20                  25                  30

Lys Thr Ser Leu Ala Asn Pro Lys Pro Trp Arg Val Ile Cys Ala Thr
        35                  40                  45

Ser Ser Gln Phe Thr Gln Ile Thr Glu His Asn Ser Arg Arg Ser Ala
    50                  55                  60

Asn Tyr Gln Pro Asn Leu Trp Asn Phe Glu Phe Leu Gln Ser Leu Glu
65                  70                  75                  80

Asn Asp Leu Lys Val Glu Lys Leu Glu Glu Lys Ala Thr Lys Leu Glu
                85                  90                  95

Glu Glu Val Arg Cys Met Ile Asn Arg Val Asp Thr Gln Pro Leu Ser
            100                 105                 110

Leu Leu Glu Leu Ile Asp Asp Val Gln Arg Leu Gly Leu Thr Tyr Lys
        115                 120                 125

Phe Glu Lys Asp Ile Ile Lys Ala Leu Glu Asn Ile Val Leu Leu Asp
    130                 135                 140

Glu Asn Lys Lys Asn Lys Ser Asp Leu His Ala Thr Ala Leu Ser Phe
145                 150                 155                 160

Arg Leu Leu Arg Gln His Gly Phe Glu Val Ser Gln Asp Val Phe Glu
                165                 170                 175
```

-continued

```
Arg Phe Lys Asp Lys Glu Gly Gly Phe Ser Gly Glu Leu Lys Gly Asp
                180                 185                 190
Val Gln Gly Leu Leu Ser Leu Tyr Glu Ala Ser Tyr Leu Gly Phe Glu
            195                 200                 205
Gly Glu Asn Leu Leu Glu Glu Ala Arg Thr Phe Ser Ile Thr His Leu
        210                 215                 220
Lys Asn Asn Leu Lys Glu Gly Ile Asn Thr Lys Val Ala Glu Gln Val
225                 230                 235                 240
Ser His Ala Leu Glu Leu Pro Tyr His Gln Arg Leu His Arg Leu Glu
                245                 250                 255
Ala Arg Trp Phe Leu Asp Lys Tyr Glu Pro Lys Glu Pro His His Gln
            260                 265                 270
Leu Leu Leu Glu Leu Ala Lys Leu Asp Phe Asn Met Val Gln Thr Leu
        275                 280                 285
His Gln Lys Glu Leu Gln Asp Leu Ser Arg Trp Trp Thr Glu Met Gly
    290                 295                 300
Leu Ala Ser Lys Leu Asp Phe Val Arg Asp Arg Leu Met Glu Val Tyr
305                 310                 315                 320
Phe Trp Ala Leu Gly Met Ala Pro Asp Pro Gln Phe Gly Glu Cys Arg
                325                 330                 335
Lys Ala Val Thr Lys Met Phe Gly Leu Val Thr Ile Ile Asp Asp Val
            340                 345                 350
Tyr Asp Val Tyr Gly Thr Leu Asp Glu Leu Gln Leu Phe Thr Asp Ala
        355                 360                 365
Val Glu Arg Trp Asp Val Asn Ala Ile Asn Thr Leu Pro Asp Tyr Met
    370                 375                 380
Lys Leu Cys Phe Leu Ala Leu Tyr Asn Thr Val Asn Asp Thr Ser Tyr
385                 390                 395                 400
Ser Ile Leu Lys Glu Lys Gly His Asn Asn Leu Ser Tyr Leu Thr Lys
                405                 410                 415
Ser Trp Arg Glu Leu Cys Lys Ala Phe Leu Gln Glu Ala Lys Trp Ser
            420                 425                 430
Asn Asn Lys Ile Ile Pro Ala Phe Ser Lys Tyr Leu Glu Asn Ala Ser
        435                 440                 445
Val Ser Ser Ser Gly Val Ala Leu Leu Ala Pro Ser Tyr Phe Ser Val
    450                 455                 460
Cys Gln Gln Gln Glu Asp Ile Ser Asp His Ala Leu Arg Ser Leu Thr
465                 470                 475                 480
Asp Phe His Gly Leu Val Arg Ser Ser Cys Val Ile Phe Arg Leu Cys
                485                 490                 495
Asn Asp Leu Ala Thr Ser Ala Ala Glu Leu Glu Arg Gly Glu Thr Thr
            500                 505                 510
Asn Ser Ile Ile Ser Tyr Met His Glu Asn Asp Gly Thr Ser Glu Glu
        515                 520                 525
Gln Ala Arg Glu Glu Leu Arg Lys Leu Ile Asp Ala Glu Trp Lys Lys
    530                 535                 540
Met Asn Arg Glu Arg Val Ser Asp Ser Thr Leu Leu Pro Lys Ala Phe
545                 550                 555                 560
Met Glu Ile Ala Val Asn Met Ala Arg Val Ser His Cys Thr Tyr Gln
                565                 570                 575
Tyr Gly Asp Gly Leu Gly Arg Pro Asp Tyr Ala Thr Glu Asn Arg Ile
            580                 585                 590
Lys Leu Leu Leu Ile Asp Pro Phe Pro Ile Asn Gln Leu Met Tyr Val
```

<210> SEQ ID NO 16
<211> LENGTH: 3133
<212> TYPE: DNA
<213> ORGANISM: Pueraria montana var.lobata

<400> SEQUENCE: 16

```
aatcaatata taatatttac ggaagatttg atgcctttcc tgattttaat ttattttat      60
ccctgcataa aataattgtg gtcaccgtac actgttcttg tcacttggac aagaaatttg    120
actagcaagc aaggtataat cattcatcta aacttatggt gatttattgc cccacctcat    180
caattttcgt gtgttttatt ttagtgtcct tggatcctcg ttccaatata aaggagaac     240
atggcatcgc aattttagag catatcattg aaaagtcatg gcaaccaacc ttttatgctt    300
gtctaataaa ttatcgtccc ccacaccaac accaagtact agatttccac aaagtaagaa    360
cttcatcaca caaaaaacat ctcttgccaa tcccaaacct tggcgagtta tttgtgctac    420
gagctctcaa tttacccaaa taacagaaca taatagtcgg cgttcagcta attaccagcc    480
aaacctctgg aattttgaat ttctgcagtc tctggaaaat gaccttaagg tgattataca    540
tatattccag ttaattttc ttttttctt ttgtgatttt taaggaatca tttagtttgg      600
gaaagtattt tttttatttg cacttttaat tataaaaatg ttatatcatt ttcacttttt    660
tctattcatt ttcaaaattt tacatagaaa acagtaaatt ttttatttt tttatttct      720
attttcatta tttctcaaat caaacggtat taaagcataa acaagaaat taatattgtt     780
cttttaattt tatttttta caataatggg aacgattata tattaggctg accttaataa     840
gttatttttt ttttataata ttgttcttat tgtaacctaa cgacaggtgg aaaaactaga    900
agagaaggca acaaagctag aggaggaggt acgatgcatg atcaacagag tagacacaca    960
accattaagc ttactagaat tgatcgacga tgtccagcgt ctaggattga cctacaagtt   1020
tgagaaggac ataatcaaag cccttgagaa tattgtttg ctggatgaga ataagaaaaa    1080
taaaagtgac ctccatgcta ctgctctcag cttccgttta cttagacaac atggctttga   1140
ggttccccaa ggtatttatg tatatatatg ttacccactt agcaacatat atatatat     1200
atattatgat tcactgacca tgcatgtggt gcagatgtgt ttgagagatt taaggacaag   1260
gagggaggtt tcagtggtga acttaaaggt gatgtgcaag ggttgctgag tctatatgaa   1320
gcatcctatc ttggctttga gggagaaaat ctcttggagg aggcaaggac attttcaata   1380
acacatctca agaacaacct aaaagaagga ataaacacca aagtggcaga acaagttagt   1440
catgcactgg aacttcccta tcatcaaaga ttgcatagac tagaagcacg atggttcctt   1500
gacaaatatg aaccaaagga accccaccat cagttactac tcgagcttgc aaagctagat   1560
ttcaatatgg tgcaaacatt gcaccagaaa gaactgcaag acctgtcaag gttagaaatt   1620
tcaattctca gtaattatt acctcataag aaattaaata acaataacaa tattgagtgt    1680
agagatttcc aattaaaaat taacatacga gaggatcaat atatattctt aggtatgtgg   1740
tactaatgaa atatatgcta ggtggtggac ggagatgggg ctagcaagca agctagactt   1800
tgtccgagac agattaatgg aagtgtattt ttgggcgttg ggaatggcac ctgatcctca   1860
attcggtgaa tgtcgtaaag ctgtcactaa aatgtttgga ttggtcacca tcatcgatga   1920
tgtatatgac gtttatggta ctttggatga gctacaactc ttcactgatg ctgttgagag   1980
gttcgtaatt gatttcagtc tcgattcagt tggaattaa ttattgctta attaataata    2040
acttgcgtac atgcatacac acagatggga cgtgaatgcc ataaacacac ttccagacta   2100
```

```
catgaagttg tgcttcctag cactttataa caccgtcaat gacacgtctt atagcatcct   2160
taaagaaaaa ggacacaaca acctttccta tttgacaaaa tctgtacata tatactaatt   2220
atctccttgg ttgattaatt agtttagttt agtttagttg gtatgtcaac acaattaatt   2280
aatattatat atggatgttg acagtggcgt gagttatgca aagcattcct tcaagaagca   2340
aaatggtcga caacaaaat cattccagca tttagcaagt acctggaaaa tgcatcggtg    2400
tcctcctccg gtgtggcttt gcttgctcct tcctacttct cagtgtgcca acaacaagaa   2460
gatatctcag accatgctct tcgttcttta actgatttcc atggccttgt gcgctcctca   2520
tgcgtcattt tcagactctg caatgatttg gctacctcag cggtgtgtaa ttaattacct   2580
taattaattt gtaacacttg ttagactaat atatataggt gtgtctgtta attactacag   2640
gctgagctag agaggggtga gacgacaaat tcaataatat cttatatgca tgagaatgac   2700
ggcacttctg aagagcaagc acgtgaggag ttgagaaaat tgatcgatgc agagtggaag   2760
aagatgaacc gagagcgagt ttcagattct acactactcc caaaagcttt tatggaaata   2820
gctgttaaca tggctcgagt ttcgcattgc acataccaat atggagacgg acttggaagg   2880
ccagactacg ccacagagaa tagaatcaag ttgctactta tagacccctt tccaatcaat   2940
caactaatgt acgtgtaaca acacaatata aacactttc tacaagtata tatttgttta   3000
atttcggtgt tgaattaggg gtcaacacag ctatatatac ttcaatggac caactcaacc   3060
aatctgataa gagaaaaaaa ataaaaataa ggttaggtta actttgtata aatccaagtt   3120
agatatcaag ttt                                                       3133

<210> SEQ ID NO 17
<211> LENGTH: 1695
<212> TYPE: DNA
<213> ORGANISM: Artificial Sequence
<220> FEATURE:
<223> OTHER INFORMATION: DNA having modified codons, which encodes
      isoprene synthase derived from Pueraria montana var.lobata and
      lacks chloroplast-localization signal (IspSK gene)

<400> SEQUENCE: 17
atgtgtgcga cctcttctca atttactcag attaccgagc ataattcccg tcgttccgca     60
aactatcagc caaacctgtg gaatttcgaa ttcctgcaat ccctggagaa cgacctgaaa    120
gtggaaaagc tggaggagaa agcgaccaaa ctggaggaag aagttcgctg catgatcaac    180
cgtgtagaca cccagccgct gtccctgctg gagctgatcg acgatgtgca gcgcctgggt    240
ctgacctaca aatttgaaaa agacatcatt aaagccctgg aaaacatcgt actgctggac    300
gaaaacaaaa gaacaaatc tgacctgcac gcaaccgctc tgtctttccg tctgctgcgt    360
cagcacggtt tcgaggtttc tcaggatgtt tttgagcgtt tcaaggataa agaaggtggt    420
ttcagcggtg aactgaaagg tgacgtccaa ggcctgctga gcctgtatga agcgtcttac    480 ctgggttcg agggtgagaa cctgctggag gaggcgcgta ccttttccat cacccacctg    540
aagaacaacc tgaaagaagg cattaatacc aaggttgcag aacaagtgag ccacgccctg    600
gaactgccat atcaccagcg tctgcaccgt ctggaggcac gttggttcct ggataaatac    660
gaaccgaaag aaccgcatca ccagctgctg ctggagctgg cgaagctgga ttttaacatg    720
gtacagaccc tgcaccagaa agagctgcaa gatctgtccc gctggtggac cgagatgggc    780
ctggctagca aactggattt tgtacgcgac cgcctgatgg aagtttattt ctgggcactg    840
ggtatggcgc cagacccgca gtttggtgaa tgtcgcaaag ctgttactaa aatgtttggt    900
```

| | |
|---|---|
| ctggtgacga tcatcgatga cgtgtatgac gtttatggca ctctggacga actgcaactg | 960 |
| ttcaccgatg ctgtagagcg ctgggacgtt aacgctatta acaccctgcc ggactatatg | 1020 |
| aaactgtgtt tcctggcact gtacaacacc gttaacgaca cgtcctattc tattctgaaa | 1080 |
| gagaaaggtc ataacaacct gtcctatctg acgaaaagct ggcgtgaact gtgcaaagcc | 1140 |
| tttctgcaag aggcgaaatg gtccaacaac aaaattatcc cggctttctc caagtacctg | 1200 |
| gaaaacgcca cgtttcctc ctccggtgta gcgctgctgg cgccgtctta cttttccgta | 1260 |
| tgccagcagc aggaagacat ctccgaccac gcgctgcgtt ccctgaccga cttccatggt | 1320 |
| ctggtgcgtt ctagctgcgt tatcttccgc ctgtgcaacg atctggccac ctctgcggcg | 1380 |
| gagctggaac gtggcgagac taccaattct atcattagct acatgcacga aaacgatggt | 1440 |
| accagcgagg aacaggcccg cgaagaactg cgtaaactga tcgacgccga atggaaaaag | 1500 |
| atgaatcgtg aacgcgttag cgactccacc ctgctgccta aagcgttcat ggaaatcgca | 1560 |
| gttaacatgg cacgtgtttc ccactgcacc taccagtatg cgatggtct gggtcgccca | 1620 |
| gactacgcga ctgaaaaccg catcaaactg ctgctgattg accctttccc gattaaccag | 1680 |
| ctgatgtatg tctaa | 1695 |

<210> SEQ ID NO 18
<211> LENGTH: 399
<212> TYPE: DNA
<213> ORGANISM: Artificial Sequence
<220> FEATURE:
<223> OTHER INFORMATION: DNA fragment comprising tac promoter (Ptac) and tryptophan operon terminator (Ttrp) (Ptac-Ttrp)

<400> SEQUENCE: 18

| | |
|---|---|
| ggtaccagat ctccctgttg acaattaatc atcggctcta taatgtgtgg aatcgtgagc | 60 |
| ggataacaat ttcacacaag gagactcccg ggagccgcca gttccgctgg cggcatttta | 120 |
| actttctta atgaagccgg aaaaatccta aattcattta atatttatct ttttaccgtt | 180 |
| tcgcttaccc cggtcgaacg tcaacttacg tcattttcc gcccaacagt aatataatca | 240 |
| aacaaattaa tcccgcaaca taacaccagt aaaatcaata atttctcta agtcacttat | 300 |
| tcctcaggta attgttaata tatccagaat gttcctcaaa atatattttc cctctatctt | 360 |
| ctcgttgcgc ttaatttgac taattctcat tagggatcc | 399 |

<210> SEQ ID NO 19
<211> LENGTH: 3383
<212> TYPE: DNA
<213> ORGANISM: Artificial Sequence
<220> FEATURE:
<223> OTHER INFORMATION: Expression plasmid pSTV28-Ptac-Ttrp

<400> SEQUENCE: 19

| | |
|---|---|
| cgtatggcaa tgaaagacgg tgagctggtg atatgggata gtgttcaccc ttgttacacc | 60 |
| gttttccatg agcaaactga aacgttttca tcgctctgga gtgaatacca cgacgatttc | 120 |
| cggcagtttc tacacatata ttcgcaagat gtggcgtgtt acggtgaaaa cctggcctat | 180 |
| ttccctaaag ggtttattga gaatatgttt ttcgtctcag ccaatccctg ggtgagtttc | 240 |
| accagttttg atttaaacgt ggccaatatg gacaacttct tcgcccccgt tttcaccatg | 300 |
| ggcaaatatt atacgcaagg cgacaaggtg ctgatgccgc tggcgattca ggttcatcat | 360 |
| gccgtttgtg atgcttcca tgtcggcaga atgcttaatg aattacaaca gtactgcgat | 420 |
| gagtggcagg gcggggcgta attttttaa ggcagttatt ggtgccctta aacgcctggt | 480 |

-continued

```
gctacgcctg aataagtgat aataagcgga tgaatggcag aaattcgaaa gcaaattcga    540
cccggtcgtc ggttcagggc agggtcgtta aatagccgct tatgtctatt gctggtttac    600
cggtttattg actaccggaa gcagtgtgac cgtgtgcttc tcaaatgcct gaggccagtt    660
tgctcaggct ctccccgtgg aggtaataat tgacgatatg atcatttatt ctgcctccca    720
gagcctgata aaaacggtta gcgcttcgtt aatacagatg taggtgttcc acagggtagc    780
cagcagcatc ctgcgatgca gatccggaac ataatggtgc agggcgcttg tttcggcgtg    840
ggtatggtgg caggccccgt ggccggggga ctgttgggcg ctgccggcac ctgtcctacg    900
agttgcatga taaagaagac agtcataagt gcggcgacga tagtcatgcc ccgcgcccac    960
cggaaggagc taccggacag cggtgcggac tgttgtaact cagaataaga aatgaggccg    1020
ctcatggcgt tccaatacgc aaaccgcctc tccccgcgcg ttggccgatt cattaatgca    1080
gctggcacga caggtttccc gactggaaag cgggcagtga gcgcaacgca attaatgtga    1140
gttagctcac tcattaggca ccccaggctt tacactttat gcttccggct cgtatgttgt    1200
gtggaattgt gagcggataa caatttcaca caggaaacag ctatgaccat gattacgaat    1260
tcgagctcgg taccagatct ccctgttgac aattaatcat cggctctata atgtgtggaa    1320
tcgtgagcgg ataacaattt cacacaagga gactcccggg agccgccagt tccgctggcg    1380
gcattttaac tttctttaat gaagccggaa aaatcctaaa ttcatttaat atttatcttt    1440
ttaccgtttc gcttaccccg gtcgaacgtc aacttacgtc atttttccgc caacagtaa     1500 tataatcaaa caaattaatc ccgcaacata acaccagtaa aatcaataat tttctctaag    1560
tcacttattc ctcaggtaat tgttaatata tccagaatgt tcctcaaaat atattttccc    1620
tctatcttct cgttgcgctt aatttgacta attctcatta gggatcctct agagtcgacc    1680
tgcaggcatg caagcttggc actggccgtc gttttacaac gtcgtgactg ggaaaaccct    1740
ggcgttaccc aacttaatcg ccttgcagca catccccctt tcgccagctg gcgtaatagc    1800
gaagaggccc gcaccgatcg cccttcccaa cagttgcgca gcctgaatgg cgaatgagct    1860
tatcgatgat aagctgtcaa acatgagaat tacaacttat atcgtatggg gctgacttca    1920
ggtgctacat ttgaagagat aaattgcact gaaatctaga aatatttat ctgattaata    1980 agatgatctt cttgagatcg ttttggtctg cgcgtaatct cttgctctga aaacgaaaaa    2040
accgccttgc agggcggttt ttcgaaggtt ctctgagcta ccaactcttt gaaccgaggt    2100
aactggcttg gaggagcgca gtcaccaaaa cttgtccttt cagtttagcc ttaaccggcg    2160
catgacttca agactaactc ctctaaatca attaccagtg gctgctgcca gtggtgcttt    2220
tgcatgtctt tccgggttgg actcaagacg atagttaccg gataaggcgc agcggtcgga    2280
ctgaacgggg ggtcgtgca tacagtccag cttggagcga actgcctacc cggaactgag    2340
tgtcaggcgt ggaatgagac aaacgcggcc ataacagcgg aatgacaccg gtaaaccgaa    2400
aggcaggaac aggagagcgc acgagggagc cgccagggga aacgcctggt atctttatag    2460
tcctgtcggg tttcgccacc actgatttga gcgtcagatt tcgtgatgct tgtcaggggg    2520
gcggagccta tggaaaaacg gctttgccgc ggccctctca cttccctgtt aagtatcttc    2580
ctggcatctt ccaggaaatc tccgcccgt tcgtaagcca tttccgctcg ccgcagtcga    2640
acgaccgagc gtagcgagtc agtgagcgag gaagcggaat atatcctgta tcacatattc    2700
tgctgacgca ccggtgcagc cttttttctc ctgccacatg aagcacttca ctgacaccct    2760
catcagtgcc aacatagtaa gccagtatac actccgctag cgctgatgtc cggcggtgct    2820
tttgccgtta cgcaccaccc cgtcagtagc tgaacaggag ggacagctga tagaaacaga    2880
```

```
agccactgga gcacctcaaa aacaccatca tacactaaat cagtaagttg gcagcatcac   2940
ccgacgcact ttgcgccgaa taaatacctg tgacggaaga tcacttcgca gaataaataa   3000
atcctggtgt ccctgttgat accgggaagc cctgggccaa cttttggcga aaatgagacg   3060
ttgatcggca cgtaagaggt tccaactttc accataatga aataagatca ctaccgggcg   3120
tattttttga gttatcgaga ttttcaggag ctaaggaagc taaaatggag aaaaaaatca   3180
ctggatatac caccgttgat atatcccaat ggcatcgtaa agaacatttt gaggcatttc   3240
agtcagttgc tcaatgtacc tataaccaga ccgttcagct ggatattacg gcctttttaa   3300
agaccgtaaa gaaaaataag cacaagtttt atccggcctt tattcacatt cttgcccgcc   3360
tgatgaatgc tcatccggaa ttt                                          3383
```

<210> SEQ ID NO 20
<211> LENGTH: 79
<212> TYPE: DNA
<213> ORGANISM: Artificial Sequence
<220> FEATURE:
<223> OTHER INFORMATION: Primer for amplifying IspSK gene

<400> SEQUENCE: 20

```
gataacaatt tcacacaata attttgttta actttaagaa ggagatataa tgtgtgcgac   60
ctcttctcaa tttactcag                                                79
```

<210> SEQ ID NO 21
<211> LENGTH: 42
<212> TYPE: DNA
<213> ORGANISM: Artificial Sequence
<220> FEATURE:
<223> OTHER INFORMATION: Primer for amplifying IspSK gene

<400> SEQUENCE: 21

```
acggccagtg aattcttaga catacatcag ctggttaatc gg                      42
```

<210> SEQ ID NO 22
<211> LENGTH: 29
<212> TYPE: DNA
<213> ORGANISM: Artificial Sequence
<220> FEATURE:
<223> OTHER INFORMATION: Primer for amplifying pSTV28-Ptac-Ttrp
      construct

<400> SEQUENCE: 22

```
gtgtgaaatt gttatccgct cacaattcc                                     29
```

<210> SEQ ID NO 23
<211> LENGTH: 27
<212> TYPE: DNA
<213> ORGANISM: Artificial Sequence
<220> FEATURE:
<223> OTHER INFORMATION: Primer for amplifying pSTV28-Ptac-Ttrp
      construct

<400> SEQUENCE: 23

```
gaattcactg gccgtcgttt tacaacg                                       27
```

<210> SEQ ID NO 24
<211> LENGTH: 60
<212> TYPE: DNA
<213> ORGANISM: Artificial Sequence
<220> FEATURE:
<223> OTHER INFORMATION: Primer for amplifying Mpdmvk gene

<400> SEQUENCE: 24
ctgatgtatg tctaactgca taaaggaggt aaaaaaacat gacgatgtgt tcagcccccg    60

<210> SEQ ID NO 25
<211> LENGTH: 47
<212> TYPE: DNA
<213> ORGANISM: Artificial Sequence
<220> FEATURE:
<223> OTHER INFORMATION: Primer for amplifying Mpdmvk gene

<400> SEQUENCE: 25
ttgtaaaacg acggccagtg aattctcatt ggatgaatat tccctcc    47

<210> SEQ ID NO 26
<211> LENGTH: 60
<212> TYPE: DNA
<213> ORGANISM: Artificial Sequence
<220> FEATURE:
<223> OTHER INFORMATION: Primer for amplifying Cvamvk gene

<400> SEQUENCE: 26
ctgatgtatg tctaactgca taaaggaggt aaaaaaacat ggccccgcac gtcggtcacg    60

<210> SEQ ID NO 27
<211> LENGTH: 47
<212> TYPE: DNA
<213> ORGANISM: Artificial Sequence
<220> FEATURE:
<223> OTHER INFORMATION: Primer for amplifying Cvamvk gene

<400> SEQUENCE: 27
ttgtaaaacg acggccagtg aattcttatt gcatcacttc acctgcc    47

<210> SEQ ID NO 28
<211> LENGTH: 60
<212> TYPE: DNA
<213> ORGANISM: Artificial Sequence
<220> FEATURE:
<223> OTHER INFORMATION: Primer for amplifying Mclmvk gene

<400> SEQUENCE: 28
ctgatgtatg tctaactgca taaaggaggt aaaaaaacat gacgatggct tccgctccgg    60

<210> SEQ ID NO 29
<211> LENGTH: 47
<212> TYPE: DNA
<213> ORGANISM: Artificial Sequence
<220> FEATURE:
<223> OTHER INFORMATION: Primer for amplifying Mclmvk gene

<400> SEQUENCE: 29
ttgtaaaacg acggccagtg aattcttacg cgacttccag gcgaaca    47

<210> SEQ ID NO 30
<211> LENGTH: 60
<212> TYPE: DNA
<213> ORGANISM: Artificial Sequence
<220> FEATURE:
<223> OTHER INFORMATION: Primer for amplifying Nmrmvk gene

<400> SEQUENCE: 30
ctgatgtatg tctaactgca taaaggaggt aaaaaaacat gaagagcaag gcatctgcgc    60

<210> SEQ ID NO 31
<211> LENGTH: 47

```
<212> TYPE: DNA
<213> ORGANISM: Artificial Sequence
<220> FEATURE:
<223> OTHER INFORMATION: Primer for amplifying Nmrmvk gene

<400> SEQUENCE: 31
ttgtaaaacg acggccagtg aattcttaaa acgtgtccag gcccttg        47

<210> SEQ ID NO 32
<211> LENGTH: 53
<212> TYPE: DNA
<213> ORGANISM: Artificial Sequence
<220> FEATURE:
<223> OTHER INFORMATION: Primer for amplifying Mmamvk gene

<400> SEQUENCE: 32
ctgatgtatg tctaactgca taaaggaggt aaaaaaacat ggtatcctgt tct        53

<210> SEQ ID NO 33
<211> LENGTH: 50
<212> TYPE: DNA
<213> ORGANISM: Artificial Sequence
<220> FEATURE:
<223> OTHER INFORMATION: Primer for amplifying Mmamvk gene

<400> SEQUENCE: 33
ttgtaaaacg acggccagtg aattcttaat ctactttcag accttgctcg        50

<210> SEQ ID NO 34
<211> LENGTH: 60
<212> TYPE: DNA
<213> ORGANISM: Artificial Sequence
<220> FEATURE:
<223> OTHER INFORMATION: Primer for amplifying ERG12 gene

<400> SEQUENCE: 34
ctgatgtatg tctaactgca taaaggaggt aaaaaaacat gtcattaccg ttcttaactt        60

<210> SEQ ID NO 35
<211> LENGTH: 48
<212> TYPE: DNA
<213> ORGANISM: Artificial Sequence
<220> FEATURE:
<223> OTHER INFORMATION: Primer for amplifying ERG12 gene

<400> SEQUENCE: 35
ttgtaaaacg acggccagtg aattcttatg aagtccatgg taaattcg        48

<210> SEQ ID NO 36
<211> LENGTH: 20
<212> TYPE: DNA
<213> ORGANISM: Artificial Sequence
<220> FEATURE:
<223> OTHER INFORMATION: Primer for amplifying pSTV28-Ptac-IspSK

<400> SEQUENCE: 36
gaattcactg gccgtcgttt        20

<210> SEQ ID NO 37
<211> LENGTH: 20
<212> TYPE: DNA
<213> ORGANISM: Artificial Sequence
<220> FEATURE:
<223> OTHER INFORMATION: Primer for amplifying pSTV28-Ptac-IspSK

<400> SEQUENCE: 37
```

-continued

```
ttagacatac atcagctggt                                              20
```

<210> SEQ ID NO 38
<211> LENGTH: 2414
<212> TYPE: DNA
<213> ORGANISM: Artificial Sequence
<220> FEATURE:
<223> OTHER INFORMATION: Genomic fragment containing attL-tetR-attR-Ptac

<400> SEQUENCE: 38

```
tgaagcctgc ttttttatac taagttggca ttataaaaaa gcattgctta tcaatttgtt     60
gcaacgaaca ggtcactatc agtcaaaata aaatcattat ttgatttcga attccccgga    120
tccgtcgacc tgcagggaaa aaggttatgc tgcttttaag acccactttc acatttaagt    180
tgttttcta atccgcatat gatcaattca aggccgaata agaaggctgg ctctgcacct     240
tggtgatcaa ataattcgat agcttgtcgt aataatggcg gcatactatc agtagtaggt    300
gtttccctt cttctttagc gacttgatgc tcttgatctt ccaatacgca acctaaagta     360
aaatgcccca cagcgctgag tgcatataat gcattctcta gtgaaaaacc ttgttggcat    420
aaaaaggcta attgattttc gagagtttca tactgttttt ctgtaggccg tgtacctaaa    480
tgtacttttg ctccatcgcg atgacttagt aaagcacatc taaaacttt agcgttatta     540
cgtaaaaaat cttgccagct ttccccttct aaagggcaaa agtgagtatg gtgcctatct    600
aacatctcaa tggctaaggc gtcgagcaaa gcccgcttat tttttacatg ccaatacaat    660
gtaggctgct ctacacctag cttctgggcg agtttacggg ttgttaaacc ttcgattccg    720
acctcattaa gcagctctaa tgcgctgtta atcactttac ttttatctaa tctagacatc    780
attaattcct aattttgtt gacactctat cattgataga gttatttac cactccctat      840
cagtgataga gaaagtgaa atgaatagtt cgacaaagat cgcattggta attacgttac    900
tcgatgccat ggggattggc cttatcatgc cagtcttgcc aacgttatta cgtgaattta    960
ttgcttcgga agatatcgct aaccactttg gcgtattgct tgcactttat gcgttaatgc   1020
aggttatctt tgctccttgg cttggaaaaa tgtctgaccg atttggtcgg cgcccagtgc   1080
tgttgttgtc attaataggc gcatcgctgg attacttatt gctggctttt tcaagtgcgc   1140
tttggatgct gtatttaggc cgtttgcttt cagggatcac aggagctact ggggctgtcg   1200
cggcatcggt cattgccgat accacctcag cttctcaacg cgtgaagtgg ttcggttggt   1260
tagggcaag ttttgggctt ggtttaatag cggggcctat tattggtggt tttgcaggag    1320
agatttcacc gcatagtccc tttttttatcg ctgcgttgct aaatattgtc actttccttg   1380
tggttatgtt ttggttccgt gaaaccaaaa atacacgtga atatacagat accgaagtag   1440
gggttgagac gcaatcgaat tcggtataca tcactttatt taaaacgatg cccatttttgt   1500
tgattattta ttttttcagcg caattgatag gccaaattcc cgcaacggtg tgggtgctat   1560
ttaccgaaaa tcgttttgga tggaatagca tgatggttgg cttttcatta gcgggtcttg   1620
gtcttttaca ctcagtattc caagcctttg tggcaggaag aatagccact aaatggggcg   1680
aaaaaacggc agtactgctc gaatttattg cagatagtag tgcatttgcc ttttttagcgt   1740
ttatatctga aggttggtta gatttccctg ttttaatttt attggctggt ggtgggatcg   1800
ctttacctgc attacaggga gtgatgtcta tccaaacaaa gagtcatgag caaggtgctt   1860
tacagggatt attggtgagc cttaccaatg caaccggtgt tattggccca ttactgtttta   1920
ctgttattta taatcattca ctaccaattt gggatggctg gatttggatt attggtttag   1980
cgttttactg tattattatc ctgctatcga tgaccttcat gttaaccccct caagctcagg   2040
```

```
ggagtaaaca ggagacaagt gcttagttat ttcgtcacca aatgatgtta ttccgcgaaa    2100
tataatgacc ctcttgataa cccaagaggg catttttttac gataaagaag atttagcttc   2160
tgcagtctgt tacaggtcac taataccatc taagtagttg attcatagtg actgcatatg    2220
ttgtgtttta cagtattatg tagtctgttt tttatgcaaa atctaattta atatattgat    2280
atttatatca ttttacgttt ctcgttcagc tttttttatac taacttgagc gagatctccc   2340
tgttgacaat taatcatcgg ctctataatg tgtggaatcg tgagcggata acaatttcac    2400
acaaggagac tgcc                                                      2414

<210> SEQ ID NO 39
<211> LENGTH: 78
<212> TYPE: DNA
<213> ORGANISM: Artificial Sequence
<220> FEATURE:
<223> OTHER INFORMATION: Primer for amplifying genomic fragment
      containing attL-tetR-attR-Ptac

<400> SEQUENCE: 39
tcatcgataa ggtcgcggcg acaacagttg cgacggtggt acgcataact tgaagcctgc    60 tttttttatac taagttgg                                                 78

<210> SEQ ID NO 40
<211> LENGTH: 78
<212> TYPE: DNA
<213> ORGANISM: Artificial Sequence
<220> FEATURE:
<223> OTHER INFORMATION: Primer for amplifying genomic fragment
      containing attL-tetR-attR-Ptac

<400> SEQUENCE: 40
ccagctagta acgctttccc tggggcactg aaggctctca actctgacat ggcagtctcc    60
ttgtgtgaaa ttgttatc                                                  78

<210> SEQ ID NO 41
<211> LENGTH: 20
<212> TYPE: DNA
<213> ORGANISM: Artificial Sequence
<220> FEATURE:
<223> OTHER INFORMATION: Primer for confirming deletion of ERG12 gene

<400> SEQUENCE: 41
agtgtcagcc catttggcat                                                20

<210> SEQ ID NO 42
<211> LENGTH: 20
<212> TYPE: DNA
<213> ORGANISM: Artificial Sequence
<220> FEATURE:
<223> OTHER INFORMATION: Primer for confirming deletion of ERG12 gene

<400> SEQUENCE: 42
gctacagcat gcattcttgc                                                20

<210> SEQ ID NO 43
<211> LENGTH: 803
<212> TYPE: PRT
<213> ORGANISM: Enterococcus faecalis

<400> SEQUENCE: 43

Met Lys Thr Val Val Ile Ile Asp Ala Leu Arg Thr Pro Ile Gly Lys
1               5                   10                  15
```

-continued

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

Leu Ala Lys Gln Leu Ile Gln Leu Gly Glu Ala Glu Val Leu Ile Ala
                100                 105                 110

Gly Gly Ile Glu Asn Met Ser Gln Ala Pro Lys Leu Gln Arg Phe Asn
            115                 120                 125

Tyr Glu Thr Glu Ser Tyr Asp Ala Pro Phe Ser Ser Met Met Tyr Asp
130                 135                 140

Gly Leu Thr Asp Ala Phe Ser Gly Gln Ala Met Gly Leu Thr Ala Glu
145                 150                 155                 160

Asn Val Ala Glu Lys Tyr His Val Thr Arg Glu Glu Gln Asp Gln Phe
                165                 170                 175

Ser Val His Ser Gln Leu Lys Ala Ala Gln Ala Gln Ala Glu Gly Ile
            180                 185                 190

Phe Ala Asp Glu Ile Ala Pro Leu Glu Val Ser Gly Thr Leu Val Glu
            195                 200                 205

Lys Asp Glu Gly Ile Arg Pro Asn Ser Ser Val Glu Lys Leu Gly Thr
210                 215                 220

Leu Lys Thr Val Phe Lys Glu Asp Gly Thr Val Thr Ala Gly Asn Ala
225                 230                 235                 240

Ser Thr Ile Asn Asp Gly Ala Ser Ala Leu Ile Ile Ala Ser Gln Glu
                245                 250                 255

Tyr Ala Glu Ala His Gly Leu Pro Tyr Leu Ala Ile Ile Arg Asp Ser
            260                 265                 270

Val Glu Val Gly Ile Asp Pro Ala Tyr Met Gly Ile Ser Pro Ile Lys
            275                 280                 285

Ala Ile Gln Lys Leu Leu Ala Arg Asn Gln Leu Thr Thr Glu Glu Ile
290                 295                 300

Asp Leu Tyr Glu Ile Asn Glu Ala Phe Ala Ala Thr Ser Ile Val Val
305                 310                 315                 320

Gln Arg Glu Leu Ala Leu Pro Glu Glu Lys Val Asn Ile Tyr Gly Gly
                325                 330                 335

Gly Ile Ser Leu Gly His Ala Ile Gly Ala Thr Gly Ala Arg Leu Leu
            340                 345                 350

Thr Ser Leu Ser Tyr Gln Leu Asn Gln Lys Glu Lys Lys Tyr Gly Val
            355                 360                 365

Ala Ser Leu Cys Ile Gly Gly Gly Leu Gly Leu Ala Met Leu Leu Glu
            370                 375                 380

Arg Pro Gln Gln Lys Lys Asn Ser Arg Phe Tyr Gln Met Ser Pro Glu
385                 390                 395                 400

Glu Arg Leu Ala Ser Leu Leu Asn Glu Gly Gln Ile Ser Ala Asp Thr
                405                 410                 415

Lys Lys Glu Phe Glu Asn Thr Ala Leu Ser Ser Gln Ile Ala Asn His
            420                 425                 430

Met Ile Glu Asn Gln Ile Ser Glu Thr Val Pro Met Gly Val Gly
            435                 440                 445

Leu His Leu Thr Val Asp Glu Thr Asp Tyr Leu Val Pro Met Ala Thr
450                 455                 460

Glu Glu Pro Ser Val Ile Ala Ala Leu Ser Asn Gly Ala Lys Ile Ala
465                 470                 475                 480

Gln Gly Phe Lys Thr Val Asn Gln Gln Arg Leu Met Arg Gly Gln Ile
                485                 490                 495

Val Phe Tyr Asp Val Ala Asp Ala Glu Ser Leu Ile Asp Glu Leu Gln
                500                 505                 510

Val Arg Glu Thr Glu Ile Phe Gln Gln Ala Glu Leu Ser Tyr Pro Ser
            515                 520                 525

Ile Val Lys Arg Gly Gly Leu Arg Asp Leu Gln Tyr Arg Ala Phe
        530                 535                 540

Asp Glu Ser Phe Val Ser Val Asp Phe Leu Val Asp Val Lys Asp Ala
545                 550                 555                 560

Met Gly Ala Asn Ile Val Asn Ala Met Leu Glu Gly Val Ala Glu Leu
                565                 570                 575

Phe Arg Glu Trp Phe Ala Glu Gln Lys Ile Leu Phe Ser Ile Leu Ser
            580                 585                 590

Asn Tyr Ala Thr Glu Ser Val Val Thr Met Lys Thr Ala Ile Pro Val
        595                 600                 605

Ser Arg Leu Ser Lys Gly Ser Asn Gly Arg Glu Ile Ala Glu Lys Ile
        610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
                645                 650                 655

Gly Asn Asp Thr Arg Ala Val Ser Ala Ser Cys His Ala Phe Ala Val
            660                 665                 670

Lys Glu Gly Arg Tyr Gln Gly Leu Thr Ser Trp Thr Leu Asp Gly Glu
        675                 680                 685

Gln Leu Ile Gly Glu Ile Ser Val Pro Leu Ala Leu Ala Thr Val Gly
        690                 695                 700

Gly Ala Thr Lys Val Leu Pro Lys Ser Gln Ala Ala Ala Asp Leu Leu
705                 710                 715                 720

Ala Val Thr Asp Ala Lys Glu Leu Ser Arg Val Val Ala Ala Val Gly
                725                 730                 735

Leu Ala Gln Asn Leu Ala Ala Leu Arg Ala Leu Val Ser Glu Gly Ile
            740                 745                 750

Gln Lys Gly His Met Ala Leu Gln Ala Arg Ser Leu Ala Met Thr Val
        755                 760                 765

Gly Ala Thr Gly Lys Glu Val Glu Ala Val Ala Gln Gln Leu Lys Arg
770                 775                 780

Gln Lys Thr Met Asn Gln Asp Arg Ala Leu Ala Ile Leu Asn Asp Leu
785                 790                 795                 800

Arg Lys Gln

<210> SEQ ID NO 44
<211> LENGTH: 2412
<212> TYPE: DNA
<213> ORGANISM: Enterococcus faecalis

<400> SEQUENCE: 44

```
atgaaaacag tagttattat tgatgcatta cgaacaccaa ttggaaaata taaaggcagc    60
ttaagtcaag taagtgccgt agacttagga acacatgtta caacacaact tttaaaaaga   120
cattccacta tttctgaaga aattgatcaa gtaatctttg gaaatgtttt acaagctgga   180
aatggccaaa atcccgcacg acaaatagca ataaacagcg gtttgtctca tgaaattccc   240
gcaatgacgg ttaatgaggt ctgcggatca ggaatgaagg ccgttatttt ggcgaaacaa   300
ttgattcaat taggagaagc ggaagtttta attgctggcg ggattgagaa tatgtcccaa   360
gcacctaaat tacaacgttt taattacgaa acagaaagct acgatgcgcc ttttcctagt   420
atgatgtatg atggattaac ggatgccttt agtggtcagg caatgggctt aactgctgaa   480
aatgtggccg aaaagtatca tgtaactaga gaagagcaag atcaatttc tgtacattca    540 caattaaaag cagctcaagc acaagcgaaa gggatattcg ctgacgaaat agccccatta   600
gaagtatcag gaacgcttgt ggagaaagat gaagggattc gccctaattc gagcgttgag   660
aagctaggaa cgcttaaaac agttttaaa gaagacggta ctgtaacagc agggaatgca    720
tcaaccatta tgatggggc ttctgctttg attattgctt cacaagaata tgccgaagca    780
cacggtcttc cttatttagc tattattcga gacagtgtgg aagtcggtat tgatccagcc   840
tatatgggaa tttcgccgat taaagccatt caaaaactgt tagcgcgcaa tcaacttact   900
acggaagaaa ttgatctgta tgaaatcaac gaagcatttg cagcaacttc aatcgtggtc   960
caaagagaac tggctttacc agaggaaaag gtcaacattt atggtggcgg tatttcatta  1020
ggtcatgcga ttggtgccac aggtgctcgt ttattaacga gtttaagtta tcaattaaat  1080
caaaaagaaa agaaatatgg agtggcttct ttatgtatcg gcggtggctt aggactcgct  1140
atgctactag agagacctca gcaaaaaaaa acagccgat tttatcaaat gagtcctgag   1200
gaacgcctgg cttctcttct taatgaaggc cagatttctg ctgatacaaa aaagaatt   1260 gaaaatacgg ctttatcttc gcagattgcc aatcatatga ttgaaaatca atcagtgaa   1320 acagaagtgc cgatgggcgt tggcttacat ttaacagtgg acgaaactga ttatttggta  1380
ccaatggcga cagaagagcc ctcagttatt gcggctttga gtaatggtgc aaaaatagca  1440
caaggattta aaacagtgaa tcaacaacgc ttaatgcgtg acaaatcgt ttttttacgat   1500 gttgcagatc ccgagtcatt gattgataaa ctacaagtaa gagaagcgga agttttcaa   1560 caagcagagt taagttatcc atctatcgtt aaacggggcg gcggcttaag agatttgcaa  1620
tatcgtactt ttgatgaatc atttgtatct gtcgactttt tagtagatgt taaggatgca  1680 atggggggcaa atatcgttaa cgctatgttg gaaggtgtgg ccgagttgtt ccgtgaatgg  1740
tttgcggagc aaaagatttt attcagtatt ttaagtaatt atgccacgga gtcggttgtt  1800
acgatgaaaa cggctattcc agtttcacgt ttaagtaagg ggagcaatgg ccgggaaatt  1860
gctgaaaaaa ttgtttttagc ttcacgctat gcttcattag atccttatcg ggcagtcacg  1920
cataacaaag gaatcatgaa tggcattgaa gctgtagttt tagctacagg aaatgataca  1980
cgcgctgtta gcgcttcttg tcatgctttt gcggtgaagg aaggtcgcta ccaaggcttg  2040
actagttgga cgctggatgg cgaacaacta attggtgaaa tttcagttcc gcttgcttta  2100
gccacggttg gcggtgccac aaaagtctta cctaaatctc aagcagctgc tgatttgtta  2160
gcagtgacgg atgcaaaaga actaagtcga gtagtagcgg ctgttggttt ggcacaaaat  2220
ttagcggcgt tacgggcctt agtctctgaa ggaattcaaa aaggacacat ggctctacaa  2280
gcacgttctt tagcgatgac ggtcggagct actggtaaag aagttgaggc agtcgctcaa  2340
caattaaaac gtcaaaaaac gatgaaccaa gaccgagcca tggctatttt aaatgattta  2400
```
agaaaacaat aa                                                                          2412

<210> SEQ ID NO 45
<211> LENGTH: 2412
<212> TYPE: DNA
<213> ORGANISM: Artificial Sequence
<220> FEATURE:
<223> OTHER INFORMATION: DNA having modified codons, which encodes mvaE
      derived from Enterococcus faecalis

<400> SEQUENCE: 45

```
atgaaaaccg tggttattat cgatgcgctg cgcacgccga ttggtaaata taaaggcagc      60
ctgtctcaag tgagcgccgt tgatctgggt acgcatgtga ccacgcagct gctgaaacgt     120
cacagcacca tctctgaaga aattgatcag gtgatctttg gtaacgttct gcaagccggt     180
aatggtcaga atccggcacg tcagattgca atcaacagtg gcctgagcca tgaaattccg     240
gcgatgaccg tgaatgaagt ttgcggtagc ggcatgaaag cggttattct ggccaaacag     300
ctgatccagc tgggtgaagc ggaagtgctg attgccggcg gtatcgaaaa catgagtcag     360
gcaccgaaac tgcaacgttt taattatgaa accgaaagct acgatgcccc gttcagctct     420
atgatgtatg atggcctgac cgatgcattt agcggtcagg cgatgggcct gacggcagaa     480
aacgtggcgg aaaaatacca tgttacccgc gaagaacagg atcagttttc tgttcacagt     540
cagctgaaag cggcccaggc ccaggcagaa ggtatttttc gcgatgaaat cgcaccgctg     600
gaagtgtctg gtacgctggt tgaaaaagat gaaggcattc gtccgaatag tagcgtggaa     660
aaactgggca ccctgaaaac ggtgttcaaa gaagatggca ccgttacggc gggcaatgca     720
agcaccatca tgatggtgc gagtgccctg attatcgcga ccaggaata tgcagaagcg     780
catggcctgc cgtacctggc cattatccgc gattctgtgg aagttggtat tgatccggca     840
tatatgggca ttagtccgat caaagcgatt cagaaactgc tggcccgtaa ccagctgacc     900
accgaagaaa ttgatctgta cgaaatcaat gaagcgtttg cagcgaccag tattgtggtt     960
cagcgcgaac tggccctgcc ggaagaaaaa gttaacattt atggcggtgg catcagcctg    1020
ggtcacgcaa ttggtgccac cggtgcacgt ctgctgacca gtctgagcta tcagctgaat    1080
cagaaagaga aaaaatacgg tgtggcaagc ctgtgtattg gtggcggtct gggtctggcc    1140
atgctgctgg aacgtccgca gcagaagaaa aactctcgtt tttaccagat gagtccggaa    1200
gaacgtctgg ccagtctgct gaacgaaggc cagattagcg cagataccaa aaaagaattc    1260
gaaaatacgg cactgtctag tcagatcgcg aaccatatga ttgaaaatca gatcagcgaa    1320
accgaagtgc cgatgggtgt tggcctgcac ctgaccgtgg atgaaacgga ttatctggtt    1380
ccgatggcga cggaagaacc gagcgttatt gccgcactgt ctaacggtgc aaaaatcgcg    1440
cagggcttta aaaccgtgaa tcagcagcgt ctgatgcgcg ccagattgt gttctacgat    1500
gttgcggatc cggaaagcct gatcgataaa ctgcaagtgc gcgaagccga agtttttcag    1560
caggcagaac tgagctatcc gtctattgtg aaacgtggcg gtggcctgcg cgatctgcaa    1620
taccgtacct ttgatgaaag tttcgtgagc gttgatttcc tggtggatgt taaagatgcc    1680
atgggtgcaa acatcgtgaa tgcgatgctg gaaggcgttg ccgaactgtt tcgtgaatgg    1740
ttcgcggaac agaaaatcct gttttctatc ctgagtaact acgcgaccga aagcgtggtt    1800
accatgaaaa cggccattcc tgtgagccgc ctgtctaaag gtagtaatgg ccgtgaaatt    1860
gcggaaaaaa tcgttctggc gagccgctat gcctctctgg atccgtaccg tgccgtgacc    1920
cataacaaag gtattatgaa tggcatcgaa gcagtggttc tggcgaccgg taacgatacc    1980
```

-continued

```
cgtgccgtgt ctgcaagttg ccatgcattc gcagttaaag aaggtcgtta tcagggcctg    2040
accagctgga cgctggatgg tgaacagctg atcggcgaaa tttctgtgcc gctggccctg    2100
gcaaccgtgg gtggcgcgac gaaagttctg ccgaaaagcc aggcggccgc agatctgctg    2160
gcggtgaccg atgcaaaaga actgtctcgc gtggttgcgg ccgttggtct ggcacagaat    2220
ctggcagcgc tgcgtgcgct ggtgtctgaa ggtattcaga aaggccacat ggcactgcaa    2280
gcccgtagtc tggccatgac cgtgggtgca acgggcaaag aagtggaagc agttgcgcag    2340
cagctgaaac gccagaaaac catgaaccag atcgtgcca tggcaatcct gaatgatctg    2400
cgcaaacagt aa                                                        2412
```

<210> SEQ ID NO 46
<211> LENGTH: 383
<212> TYPE: PRT
<213> ORGANISM: Enterococcus faecalis

<400> SEQUENCE: 46

```
Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Leu Ala Lys Asn His Val Ala Leu His
        115                 120                 125

Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
            260                 265                 270

Val Gly Asn Leu Tyr Thr Gly Ser Leu Tyr Leu Gly Leu Ile Ser Leu
        275                 280                 285
```

```
Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
                340                 345                 350

Glu Thr Leu Asp Thr Asp Ile Asp Gln Thr Leu Glu Asp Glu Leu Lys
            355                 360                 365

Tyr Ser Ile Ser Ala Ile Asn Asn Thr Val Arg Ser Tyr Arg Asn
    370                 375                 380

<210> SEQ ID NO 47
<211> LENGTH: 1152
<212> TYPE: DNA
<213> ORGANISM: Enterococcus faecalis

<400> SEQUENCE: 47
atgacaattg ggattgataa aattagtttt tttgtgcccc cttattatat tgatatgacg      60
gcactggctg aagccagaaa tgtagaccct ggaaaatttc atattggtat tgggcaagac     120
caaatggcgg tgaacccaat cagccaagat attgtgacat tgcagccaa tgccgcagaa     180 gcgatcttga ccaagaaga taagaggcc attgatatgg tgattgtcgg gactgagtcc     240
agtatcgatg agtcaaaagc ggccgcagtt gtcttacatc gtttaatggg gattcaacct     300
ttcgctcgct ctttcgaaat caaggaagct tgttacggag caacagcagg cttacagtta     360
gctaagaatc acgtagcctt acatccagat aaaaaagtct tggtcgtagc ggcagatatt     420
gcaaaatatg gcttaaattc tggcggtgag cctacacaag agctggggc ggttgcaatg     480 ttagttgcta gtgaaccgcg cattttggct ttaaaagagg ataatgtgat gctgacgcaa     540
gatatctatg actttggcg tccaacaggc caccgtatc ctatggtcga tggtccttg     600 tcaaacgaaa cctacatcca atcttttgcc caagtctggg atgaacataa aaaacgaacc     660
ggtcttgatt tgcagatta tgatgcttta gcgttccata ttccttacac aaaaatgggc     720
aaaaaagcct tattagcaaa aatctccgac caaactgaag cagaacagga acgaatttta     780
gcccgttatg aagaaagtat cgtctatagt cgtcgcgtag aaacttgta tacgggttca     840 ctttatctgg gactcatttc cctttttagaa aatgcaacga ctttaaccgc aggcaatcaa     900
attggtttat tcagttatgg ttctggtgct gtcgctgaat ttttcactgg tgaattagta     960
gctggttatc aaaatcattt acaaaaagaa actcatttag cactgctgga taatcggaca    1020
gaactttcta tcgctgaata tgaagccatg tttgcagaaa ctttagacac agacattgat    1080
caaacgttag aagatgaatt aaaatatagt atttctgcta ttaataatac cgttcgttct    1140
tatcgaaact aa                                                       1152

<210> SEQ ID NO 48
<211> LENGTH: 1152
<212> TYPE: DNA
<213> ORGANISM: Artificial Sequence
<220> FEATURE:
<223> OTHER INFORMATION: DNA having modified codons, which encodes mvaS
      derived from Enterococcus faecalis

<400> SEQUENCE: 48
atgaccattg gtatcgataa aattagcttt ttcgtgccgc cgtattacat cgatatgacg      60
```

```
gcgctggccg aagcacgtaa cgttgatccg ggcaaatttc atattggcat cggtcaggat    120
cagatggcgg tgaacccgat ttctcaggat atcgttacct tcgcggccaa tgcagcggaa    180
gcaattctga cgaaagaaga taaagaagcg attgatatgg tgatcgttgg caccgaaagc    240
tctatcgatg aaagtaaagc cgcagcggtg gttctgcacc gtctgatggg cattcagccg    300
tttgcgcgca gcttcgaaat caaagaagcc tgctatggcg cgaccgccgg tctgcaactg    360
gccaaaaacc atgtggcact gcacccggat aaaaaagttc tggtggttgc cgcagatatt    420
gcgaaatacg gtctgaatag cggcggtgaa ccgacccagg gtgcaggtgc cgtggcaatg    480
ctggttgcat ctgaaccgcg tattctggcg ctgaaagaag ataacgtgat gctgacccag    540
gatatctatg attttttggcg tccgaccggt catccgtacc cgatggtgga tggcccgctg    600
agtaatgaaa cctatattca gagcttcgcc caggtttggg atgaacataa aaaacgtacg    660
ggtctggatt ttgcggatta tgatgcactg gcgttccaca ttccgtacac caaaatgggc    720
aaaaaagcgc tgctggccaa aatcagcgat cagacggaag ccgaacagga acgtattctg    780
gcacgctatg aagaaagcat cgtgtactct cgtcgcgttg caacctgta taccggttct    840 ctgtacctgg gcctgattag tctgctggaa aacgcgacca cgctgacggc cggcaatcag    900
atcggtctgt tttcttatgg cagtggtgcc gtggcagaat ttttcaccgg tgaactggtt    960
gccggctacc agaaccatct gcaaaaagaa acccacctgg ccctgctgga taatcgcacg    1020
gaactgtcta ttgcagaata tgaagcaatg tttgcggaaa ccctggatac ggatatcgat    1080
cagaccctgg aagatgaact gaaatatagt attagcgcga tcaacaatac ggtgcgtagt    1140
taccgcaatt aa    1152
```

```
<210> SEQ ID NO 49
<211> LENGTH: 40
<212> TYPE: DNA
<213> ORGANISM: Artificial Sequence
<220> FEATURE:
<223> OTHER INFORMATION: Primer for amplifying a fragment comprising
      Para composed of araC and ara BAD promoters from E.coli

<400> SEQUENCE: 49
tgaattcgag ctcggtaccc actcttcctt tttcaatatt                           40

<210> SEQ ID NO 50
<211> LENGTH: 40
<212> TYPE: DNA
<213> ORGANISM: Artificial Sequence
<220> FEATURE:
<223> OTHER INFORMATION: Primer for amplifying a fragment comprising
      Para composed of araC and ara BAD promoters from E.coli

<400> SEQUENCE: 50
ataataacca cggttttcat tttttataac ctccttagag                           40

<210> SEQ ID NO 51
<211> LENGTH: 40
<212> TYPE: DNA
<213> ORGANISM: Artificial Sequence
<220> FEATURE:
<223> OTHER INFORMATION: Primer for amplifying a fragment comprising
      EFmvaE gene

<400> SEQUENCE: 51
ctctaaggag gttataaaaa atgaaaaccg tggttattat                           40

<210> SEQ ID NO 52
```

-continued

```
<211> LENGTH: 55
<212> TYPE: DNA
<213> ORGANISM: Artificial Sequence
<220> FEATURE:
<223> OTHER INFORMATION: Primer for amplifying a fragment comprising
      EFmvaE gene

<400> SEQUENCE: 52
ttatcgatac caatggtcat gttttttac ctcctttact gtttgcgcag atcat          55

<210> SEQ ID NO 53
<211> LENGTH: 55
<212> TYPE: DNA
<213> ORGANISM: Artificial Sequence
<220> FEATURE:
<223> OTHER INFORMATION: Primer for amplifying a fragment comprising
      EFmvaS gene

<400> SEQUENCE: 53
atgatctgcg caaacagtaa aggaggtaaa aaaacatgac cattggtatc gataa          55

<210> SEQ ID NO 54
<211> LENGTH: 40
<212> TYPE: DNA
<213> ORGANISM: Artificial Sequence
<220> FEATURE:
<223> OTHER INFORMATION: Primer for amplifying a fragment comprising
      EFmvaS gene

<400> SEQUENCE: 54
cagcggaact ggcggctccc ttaattgcgg taactacgca                           40

<210> SEQ ID NO 55
<211> LENGTH: 40
<212> TYPE: DNA
<213> ORGANISM: Artificial Sequence
<220> FEATURE:
<223> OTHER INFORMATION: Primer for amplifying a fragment comprising
      Ttrp

<400> SEQUENCE: 55
tgcgtagtta ccgcaattaa gggagccgcc agttccgctg                           40

<210> SEQ ID NO 56
<211> LENGTH: 38
<212> TYPE: DNA
<213> ORGANISM: Artificial Sequence
<220> FEATURE:
<223> OTHER INFORMATION: Primer for amplifying a fragment comprising
      Ttrp

<400> SEQUENCE: 56
gtcgactcta gaggatccct aatgagaatt agtcaaat                             38

<210> SEQ ID NO 57
<211> LENGTH: 40
<212> TYPE: DNA
<213> ORGANISM: Artificial Sequence
<220> FEATURE:
<223> OTHER INFORMATION: Primer 1 for amplifying Cvamvk gene (cva_mvk_N)

<400> SEQUENCE: 57
tttcacacaa ggagactccc atggccccgc acgtcggtca                           40

<210> SEQ ID NO 58
<211> LENGTH: 40
<212> TYPE: DNA
```

<213> ORGANISM: Artificial Sequence
<220> FEATURE:
<223> OTHER INFORMATION: Primer 2 for amplifying Cvamvk gene (cva_mvk_C)

<400> SEQUENCE: 58
cagcggaact ggcggctccc ttattgcatc acttcacctg        40

<210> SEQ ID NO 59
<211> LENGTH: 40
<212> TYPE: DNA
<213> ORGANISM: Artificial Sequence
<220> FEATURE:
<223> OTHER INFORMATION: Primer 1 for amplifying Mclmvk gene (mcl_mvk_N)

<400> SEQUENCE: 59
tttcacacaa ggagactccc atgacgatgg cttccgctcc        40

<210> SEQ ID NO 60
<211> LENGTH: 40
<212> TYPE: DNA
<213> ORGANISM: Artificial Sequence
<220> FEATURE:
<223> OTHER INFORMATION: Primer 2 for amplifying Mclmvk gene (mcl_mvk_C)

<400> SEQUENCE: 60
cagcggaact ggcggctccc ttacgcgact tccaggcgaa        40

<210> SEQ ID NO 61
<211> LENGTH: 40
<212> TYPE: DNA
<213> ORGANISM: Artificial Sequence
<220> FEATURE:
<223> OTHER INFORMATION: Primer 1 for amplifying Nmrmvk gene (nmr_mvk_N)

<400> SEQUENCE: 61
tttcacacaa ggagactccc atgaagagca aggcatctgc        40

<210> SEQ ID NO 62
<211> LENGTH: 40
<212> TYPE: DNA
<213> ORGANISM: Artificial Sequence
<220> FEATURE:
<223> OTHER INFORMATION: Primer 2 for amplifying Nmrmvk gene (nmr_mvk_C)

<400> SEQUENCE: 62
cagcggaact ggcggctccc ttaaaacgtg tccaggccct        40

<210> SEQ ID NO 63
<211> LENGTH: 40
<212> TYPE: DNA
<213> ORGANISM: Artificial Sequence
<220> FEATURE:
<223> OTHER INFORMATION: Primer 1 for amplifying Mmamvk gene (MMVKf)

<400> SEQUENCE: 63
tttcacacaa ggagactccc atggtatcct gttctgcgcc        40

<210> SEQ ID NO 64
<211> LENGTH: 40
<212> TYPE: DNA
<213> ORGANISM: Artificial Sequence
<220> FEATURE:
<223> OTHER INFORMATION: Primer 2 for amplifying Mmamvk gene (MMVKr)

<400> SEQUENCE: 64
cagcggaact ggcggctccc ttaatctact ttcagacctt        40

<210> SEQ ID NO 65
<211> LENGTH: 20
<212> TYPE: DNA
<213> ORGANISM: Artificial Sequence
<220> FEATURE:
<223> OTHER INFORMATION: Primer 1 for amplifying pMW219-Ptac-Ttrp
      (PtTt219f)

<400> SEQUENCE: 65
gggagccgcc agttccgctg                                              20

<210> SEQ ID NO 66
<211> LENGTH: 21
<212> TYPE: DNA
<213> ORGANISM: Artificial Sequence
<220> FEATURE:
<223> OTHER INFORMATION: Primer 2 for amplifying pMW219-Ptac-Ttrp
      (PtTt219r)

<400> SEQUENCE: 66
gggagtctcc ttgtgtgaaa t                                            21

<210> SEQ ID NO 67
<211> LENGTH: 108
<212> TYPE: DNA
<213> ORGANISM: Artificial Sequence
<220> FEATURE:
<223> OTHER INFORMATION: Primer 1 for pUC-mvk-pmk (KKDS1_6038-3-1)

<400> SEQUENCE: 67
gaggaataaa ccatggatcc gagctcggat ccactagtaa cggccgccag tgtgctggaa    60
ttcgcccttA ggaggtaaaa aaacatgtca ttaccgttct taacttct                108

<210> SEQ ID NO 68
<211> LENGTH: 55
<212> TYPE: DNA
<213> ORGANISM: Artificial Sequence
<220> FEATURE:
<223> OTHER INFORMATION: Primer 2 for pUC-mvk-pmk (KKMyIA_6038-2-9)

<400> SEQUENCE: 68
aagggcgaat tctgcatgca gctaccttaa gttatttatc aagataagtt tccgg         55

<210> SEQ ID NO 69
<211> LENGTH: 51
<212> TYPE: DNA
<213> ORGANISM: Artificial Sequence
<220> FEATURE:
<223> OTHER INFORMATION: Primer 1 for pTWV-dmd-yidi (KMS_6038-6-1)

<400> SEQUENCE: 69
gcagaattcg cccttaagga ggaaaaaaaa atgaccgttt acacagcatc c             51

<210> SEQ ID NO 70
<211> LENGTH: 47
<212> TYPE: DNA
<213> ORGANISM: Artificial Sequence
<220> FEATURE:
<223> OTHER INFORMATION: Primer 2 for pTWV-dmd-yidi (KDyIA_6038-3-3)

<400> SEQUENCE: 70
ccatatggta ccagctgcag ttatagcatt ctatgaattt gcctgtc                  47

<210> SEQ ID NO 71

<211> LENGTH: 9329
<212> TYPE: DNA
<213> ORGANISM: Artificial Sequence
<220> FEATURE:
<223> OTHER INFORMATION: Nucleotide sequence of the expression vector, pTrc-KKDyI(alpha)

<400> SEQUENCE: 71

| | | | | | |
|---|---|---|---|---|---|
| gtttgacagc | ttatcatcga | ctgcacggtg | caccaatgct | tctggcgtca | ggcagccatc | 60 |
| ggaagctgtg | gtatggctgt | gcaggtcgta | aatcactgca | taattcgtgt | cgctcaaggc | 120 |
| gcactcccgt | tctggataat | gttttttgcg | ccgacatcat | aacggttctg | gcaaatattc | 180 |
| tgaaatgagc | tgttgacaat | taatcatccg | gctcgtataa | tgtgtggaat | tgtgagcgga | 240 |
| taacaatttc | acacaggaaa | cagcgccgct | gagaaaaagc | gaagcggcac | tgctctttaa | 300 |
| caatttatca | gacaatctgt | gtgggcactc | gaccggaatt | atcgattaac | tttattatta | 360 |
| aaaattaaag | aggtatatat | taatgtatcg | attaaataag | gaggaataaa | ccatggatcc | 420 |
| gagctcggat | ccactagtaa | cggccgccag | tgtgctggaa | ttcgccctta | ggaggtaaaa | 480 |
| aaacatgtca | ttaccgttct | taacttctgc | accgggaaag | gttattattt | tggtgaaca | 540 |
| ctctgctgtg | tacaacaagc | ctgccgtcgc | tgctagtgtg | tctgcgttga | gaacctacct | 600 |
| gctaataagc | gagtcatctg | caccagatac | tattgaattg | acttcccgg | acattagctt | 660 |
| taatcataag | tggtccatca | atgatttcaa | tgccatcacc | gaggatcaag | taaactccca | 720 |
| aaaattggcc | aaggctcaac | aagccaccga | tggcttgtct | caggaactcg | ttagtctttt | 780 |
| ggatccgttg | ttagctcaac | tatccgaatc | cttccactac | catgcagcgt | tttgtttcct | 840 |
| gtatatgttt | gtttgcctat | gcccccatgc | caagaatatt | aagttttctt | taaagtctac | 900 |
| tttacccatc | ggtgctgggt | tgggctcaag | cgcctctatt | tctgtatcac | tggccttagc | 960 |
| tatggcctac | ttgggggggt | taataggatc | taatgacttg | gaaaagctgt | cagaaaacga | 1020 |
| taagcatata | gtgaatcaat | gggccttcat | aggtgaaaag | tgtattcacg | gtaccccttc | 1080 |
| aggaatagat | aacgctgtgg | ccacttatgg | taatgccctg | ctatttgaaa | aagactcaca | 1140 |
| taatggaaca | ataaacacaa | acaattttaa | gttcttagat | gatttcccag | ccattccaat | 1200 |
| gatcctaacc | tatactagaa | ttccaaggtc | tacaaaagat | cttgttgctc | gcgttcgtgt | 1260 |
| gttggtcacc | gagaaatttc | ctgaagttat | gaagccaatt | ctagatgcca | tgggtgaatg | 1320 |
| tgccctacaa | ggcttagaga | tcatgactaa | gttaagtaaa | tgtaaaggca | ccgatgacga | 1380 |
| ggctgtagaa | actaataatg | aactgtatga | caactattg | gaattgataa | gaataaatca | 1440 |
| tggactgctt | gtctcaatcg | gtgtttctca | tcctggatta | gaacttatta | aaaatctgag | 1500 |
| cgatgatttg | agaattggct | ccacaaaact | taccggtgct | ggtggcggcg | ttgctctttt | 1560 |
| gactttgtta | cgaagagaca | ttactcaaga | gcaaattgac | agcttcaaaa | agaaattgca | 1620 |
| agatgatttt | agttacgaga | catttgaaac | agacttgggt | gggactggct | gctgtttgtt | 1680 |
| aagcgcaaaa | aatttgaata | agatcttaa | atcaaatcc | ctagtattcc | aattatttga | 1740 |
| aaataaaact | accacaaagc | aacaaattga | cgatctatta | ttgccaggaa | acacgaattt | 1800 |
| accatggact | tcataagcta | atttgcgata | ggcctgcacc | cttaaggagg | aaaaaaacat | 1860 |
| gtcagagttg | agagccttca | gtgccccagg | gaaagcgtta | ctagctggtg | gatatttagt | 1920 |
| tttagataca | aaatatgaag | catttgtagt | cggattatcg | gcaagaatgc | atgctgtagc | 1980 |
| ccatccttac | ggttcattgc | aagggtctga | taagtttgaa | gtgcgtgtga | aaagtaaaca | 2040 |
| atttaaagat | ggggagtggc | tgtaccatat | aagtcctaaa | agtggcttca | ttcctgtttc | 2100 |

-continued

```
gataggcgga tctaagaacc ctttcattga aaaagttatc gctaacgtat ttagctactt    2160
taaacctaac atggacgact actgcaatag aaacttgttc gttattgata ttttctctga    2220
tgatgcctac cattctcagg aggatagcgt taccgaacat cgtggcaaca gaagattgag    2280
ttttcattcg cacagaattg aagaagttcc caaaacaggg ctgggctcct cggcaggttt    2340
agtcacagtt ttaactacag ctttggcctc ctttttttgta tcggacctgg aaaataatgt    2400
agacaaatat agagaagtta ttcataattt agcacaagtt gctcattgtc aagctcaggg    2460
taaaattgga agcgggtttg atgtagcggc ggcagcatat ggatctatca gatatagaag    2520
attcccaccc gcattaatct ctaatttgcc agatattgga agtgctactt acggcagtaa    2580
actggcgcat ttggttgatg aagaagactg gaatattacg attaaaagta accatttacc    2640
ttcgggatta actttatgga tgggcgatat taagaatggt tcagaaacag taaaactggt    2700
ccagaaggta aaaaattggt atgattcgca tatgccagaa agcttgaaaa tatatacaga    2760
actcgatcat gcaaattcta gatttatgga tggactatct aaactagatc gcttacacga    2820
gactcatgac gattacagcg atcagatatt tgagtctctt gagaggaatg actgtacctg    2880
tcaaaagtat cctgaaatca cagaagttag agatgcagtt gccacaatta gacgttcctt    2940
tagaaaaata actaaagaat ctggtgccga tatcgaacct cccgtacaaa ctagcttatt    3000
ggatgattgc cagaccttaa aaggagttct tacttgctta atacctggtg ctggtggtta    3060
tgacgccatt gcagtgatta ctaagcaaga tgttgatctt agggctcaaa ccgctaatga    3120
caaaagattt tctaaggttc aatggctgga tgtaactcag gctgactggg gtgttaggaa    3180
agaaaaagat ccgaaaactt atcttgataa ataacttaag gtagctgcat gcagaattcg    3240
cccttaagga ggaaaaaaaa atgaccgttt acacagcatc cgttaccgca cccgtcaaca    3300
tcgcaaccct taagtattgg gggaaaaggg acacgaagtt gaatctgccc accaattcgt    3360
ccatatcagt gactttatcg caagatgacc tcagaacgtt gacctctgcg gctactgcac    3420
ctgagtttga acgcgacact tgtggttaa atggagaacc acacagcatc gacaatgaaa    3480
gaactcaaaa ttgtctgcgc gacctacgcc aattaagaaa ggaaatggaa tcgaaggacg    3540
cctcattgcc cacattatct caatggaaac tccacattgt ctccgaaaat aactttccta    3600
cagcagctgg tttagcttcc tccgctgctg gctttgctgc attggtctct gcaattgcta    3660
agttataccca attaccacag tcaacttcag aaatatctag aatagcaaga aaggggtctg    3720
gttcagcttg tagatcgttg tttggcggat acgtggcctg ggaaatggga aaagctgaag    3780
atggtcatga ttcatggca gtacaaatcg cagacagctc tgactggcct cagatgaaag    3840
cttgtgtcct agttgtcagc gatattaaaa aggatgtgag ttccactcag ggtatgcaat    3900
tgaccgtggc aacctccgaa ctatttaaag aaagaattga acatgtcgta ccaaagagat    3960
ttgaagtcat gcgtaaagcc attgttgaaa agatttcgc caccttttgca aaggaaacaa    4020
tgatggattc caactctttc catgccacat gtttggactc tttccctcca atattctaca    4080
tgaatgacac ttccaagcgt atcatcagtt ggtgccacac cattaatcag ttttacggag    4140
aaacaatcgt tgcatacacg tttgatgcag gtccaaatgc tgtgttgtac tacttagctg    4200
aaaatgagtc gaaactcttt gcatttatct ataaattgtt tggctctgtt cctggatggg    4260
acaagaaatt tactactgag cagcttgagg ctttcaacca tcaatttgaa tcatctaact    4320
ttactgcacg tgaattggat cttgagttgc aaaaggatgt tgccagagtg attttaactc    4380
aagtcggttc aggcccacaa gaaacaaacg aatcttgat tgacgcaaag actggtctac    4440
caaaggaata agatcaattc gctgcatcgc ccttaggagg taaaaaaaaa tgactgccga    4500
```

```
caacaatagt atgccccatg gtgcagtatc tagttacgcc aaattagtgc aaaaccaaac    4560
acctgaagac attttggaag agtttcctga aattattcca ttacaacaaa gacctaatac    4620
ccgatctagt gagacgtcaa atgacgaaag cggagaaaca tgttttttctg gtcatgatga   4680
ggagcaaatt aagttaatga atgaaaattg tattgttttg gattgggacg ataatgctat    4740
tggtgccggt accaagaaag tttgtcattt aatggaaaat attgaaaagg gtttactaca    4800
tcgtgcattc tccgtctttta ttttcaatga acaaggtgaa ttactttttac aacaaagagc  4860
cactgaaaaa ataactttcc ctgatctttg gactaacaca tgctgctctc atccactatg    4920
tattgatgac gaattaggtt tgaagggtaa gctagacgat aagattaagg gcgctattac    4980
tgcggcggtg agaaaactag atcatgaatt aggtattcca agatgaaa ctaagacaag      5040
gggtaagttt cactttttaa acagaatcca ttacatggca ccaagcaatg aaccatgggg   5100
tgaacatgaa attgattaca tcctatttta aagatcaac gctaaagaaa acttgactgt     5160
caacccaaac gtcaatgaag ttagagactt caaatgggtt tcaccaaatg atttgaaaac   5220
tatgtttgct gacccaagtt acaagtttac gccttggttt aagattattt gcgagaatta   5280
cttattcaac tggtgggagc aattagatga cctttctgaa gtggaaaatg acaggcaaat   5340
tcatagaatg ctataactgc agctggtacc atatgggaat tcgaagcttt ctagaacaaa   5400
aactcatctc agaagaggat ctgaatagcg ccgtcgacca tcatcatcat catcattgag   5460
tttaaacggt ctccagcttg gctgttttgg cggatgagag aagattttca gcctgataca   5520
gattaaatca gaacgcagaa gcggtctgat aaaacagaat ttgcctggcg gcagtagcgc   5580
ggtggtccca cctgacccca tgccgaactc agaagtgaaa cgccgtagcg ccgatggtag   5640
tgtgggtct ccccatgcga gagtagggaa ctgccaggca tcaaataaaa cgaaaggctc    5700
agtcgaaaga ctgggccttt cgttttatct gttgtttgtc ggtgaacgct ctcctgagta   5760
ggacaaatcc gccgggagcg gatttgaacg ttgcgaagca acggcccgga gggtggcggg   5820
caggacgccc gccataaact gccaggcatc aaattaagca gaaggccatc ctgacggatg   5880
gcctttttgc gtttctacaa actctttttg tttattttc taaatacatt caaatatgta    5940
tccgctcatg agacaataac cctgataaat gcttcaataa tattgaaaaa ggaagagtat   6000
gagtattcaa catttccgtg tcgcccttat tccctttttt gcggcatttt gccttcctgt   6060
ttttgctcac ccagaaacgc tggtgaaagt aaaagatgct gaagatcagt tgggtgcacg   6120
agtgggttac atcgaactgg atctcaacag cggtaagatc cttgagagtt ttcgccccga   6180
agaacgtttt ccaatgatga gcactttaa agttctgcta tgtggcgcgg tattatcccg   6240
tgttgacgcc gggcaagagc aactcggtcg ccgcatacac tattctcaga atgacttggt   6300
tgagtactca ccagtcacag aaaagcatct tacggatggc atgacagtaa gagaattatg   6360
cagtgctgcc ataaccatga gtgataacac tgcggccaac ttacttctga caacgatcgg   6420
aggaccgaag gagctaaccg cttttttgca caacatgggg gatcatgtaa ctcgccttga   6480
tcgttgggaa ccggagctga atgaagccat accaaacgac gagcgtgaca ccacgatgcc   6540
tgtagcaatg gcaacaacgt tgcgcaaact attaactggc gaactactta ctctagcttc   6600
ccggcaacaa ttaatagact ggatggaggc ggataaagtt gcaggaccac ttctgcgctc   6660
ggcccttccg gctggctggt ttattgctga taaatctgga gccggtgagc gtgggtctcg   6720
cggtatcatt gcagcactgg ggccagatgg taagccctcc cgtatcgtag ttatctacac   6780
gacggggagt caggcaacta tggatgaacg aaatagacag atcgctgaga taggtgcctc   6840
```

```
actgattaag cattggtaac tgtcagacca agtttactca tatatacttt agattgattt    6900
aaaacttcat tttaattta aaaggatcta ggtgaagatc cttttttgata atctcatgac    6960
caaaatccct taacgtgagt tttcgttcca ctgagcgtca gaccccgtag aaaagatcaa    7020
aggatcttct tgagatcctt ttttttctgcg cgtaatctgc tgcttgcaaa caaaaaaacc    7080
accgctacca gcggtggttt gtttgccgga tcaagagcta ccaactcttt ttccgaaggt    7140
aactggcttc agcagagcgc agataccaaa tactgtcctt ctagtgtagc cgtagttagg    7200
ccaccacttc aagaactctg tagcaccgcc tacatacctc gctctgctaa tcctgttacc    7260
agtggctgct gccagtggcg ataagtcgtg tcttaccggg ttggactcaa gacgatagtt    7320
accggataag gcgcagcggt cgggctgaac ggggggttcg tgcacacagc ccagcttgga    7380
gcgaacgacc tacaccgaac tgagatacct acagcgtgag ctatgagaaa gcgccacgct    7440
tcccgaaggg agaaaggcgg acaggtatcc ggtaagcggc agggtcggaa caggagagcg    7500
cacgagggag cttccagggg gaaacgcctg gtatctttat agtcctgtcg ggtttcgcca    7560
cctctgactt gagcgtcgat ttttgtgatg ctcgtcaggg gggcggagcc tatggaaaaa    7620
cgccagcaac gcggcctttt tacggttcct ggccttttgc tggccttttg ctcacatgtt    7680
ctttcctgcg ttatccctg attctgtgga taaccgtatt accgcctttg agtgagctga    7740
taccgctcgc cgcagccgaa cgaccgagcg cagcgagtca gtgagcgagg aagcggaaga    7800
gcgcctgatg cggtattttc tccttacgca tctgtgcggt atttcacacc gcatatggtg    7860
cactctcagt acaatctgct ctgatgccgc atagttaagc cagtatacac tccgctatcg    7920
ctacgtgact gggtcatggc tgcgccccga cacccgccaa cacccgctga cgcgccctga    7980
cgggcttgtc tgctcccggc atccgcttac agacaagctg tgaccgtctc cgggagctgc    8040
atgtgtcaga ggttttcacc gtcatcaccg aaacgcgcga ggcagcagat caattcgcgc    8100
gcgaaggcga agcggcatgc atttacgttg acaccatcga atggtgcaaa acctttcgcg    8160
gtatggcatg atagcgcccg gaagagagtc aattcagggt ggtgaatgtg aaaccagtaa    8220
cgttatacga tgtcgcagag tatgccggtg tctcttatca gaccgtttcc cgcgtggtga    8280
accaggccag ccacgtttct gcgaaaacgc gggaaaaagt ggaagcggcg atggcggagc    8340
tgaattacat tcccaaccgc gtggcacaac aactggcggg caaacagtcg ttgctgattg    8400
gcgttgccac ctccagtctg gccctgcacg cgccgtcgca aattgtcgcg gcgattaaat    8460
ctcgcgccga tcaactgggt gccagcgtgg tggtgtcgat ggtagaacga agcggcgtcg    8520
aagcctgtaa agcggcggtg cacaatcttc tcgcgcaacg cgtcagtggg ctgatcatta    8580
actatccgct ggatgaccag gatgccattg ctgtggaagc tgcctgcact aatgttccgg    8640
cgttatttct tgatgtctct gaccagacac ccatcaacag tattattttc tcccatgaag    8700
acggtacgcg actgggcgtg gagcatctgg tcgcattggg tcaccagcaa atcgcgctgt    8760
tagcgggccc attaagttct gtctcggcgc gtctgcgtct ggctggctgg cataaatatc    8820
tcactcgcaa tcaaattcag ccgatagcgg aacgggaagg cgactggagt gccatgtccg    8880
gttttcaaca aaccatgcaa atgctgaatg agggcatcgt tcccactgcg atgctggttg    8940
ccaacgatca gatggcgctg ggcgcaatgc gcgccattac cgagtccggg ctgcgcgttg    9000
gtgcggatat ctcggtagtg ggatacgacg ataccgaaga cagctcatgt tatatcccgc    9060
cgtcaaccac catcaaacag gattttcgcc tgctggggca aaccagcgtg gaccgcttgc    9120
tgcaactctc tcagggccag gcggtgaagg gcaatcagct gttgcccgtc tcactggtga    9180
aaagaaaaac caccctggcg cccaatacgc aaaccgcctc tccccgcgcg ttggccgatt    9240
```

| | |
|---|---|
| cattaatgca gctggcacga caggtttccc gactggaaag cgggcagtga gcgcaacgca | 9300 |
| attaatgtga gttagcgcga attgatctg | 9329 |

<210> SEQ ID NO 72
<211> LENGTH: 68
<212> TYPE: DNA
<213> ORGANISM: Artificial Sequence
<220> FEATURE:
<223> OTHER INFORMATION: Primer for amplifying IspSK gene
    (pTrcKKDyIkSS_6038-10-1)

<400> SEQUENCE: 72

| | |
|---|---|
| atagaatgct ataacaacgc gtcctgcatt cgcccttagg aggtaaaaaa acatgtgtgc | 60 |
| gacctctt | 68 |

<210> SEQ ID NO 73
<211> LENGTH: 46
<212> TYPE: DNA
<213> ORGANISM: Artificial Sequence
<220> FEATURE:
<223> OTHER INFORMATION: Primer for amplifying IspSK gene
    (pTrcKKDyIkSS_6038-10-2)

<400> SEQUENCE: 73

| | |
|---|---|
| ccatatggta ccagctgcag ttagacatac atcagctggt taatcg | 46 |

<210> SEQ ID NO 74
<211> LENGTH: 11062
<212> TYPE: DNA
<213> ORGANISM: Artificial Sequence
<220> FEATURE:
<223> OTHER INFORMATION: Nucleotide sequence of the expression vector,
    pTrc-KKDyI(alpha)-ispS(K)

<400> SEQUENCE: 74

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggatcc | 420 |
| gagctcggat ccactagtaa cggccgccag tgtgctggaa ttcgccctta ggaggtaaaa | 480 |
| aaacatgtca ttaccgttct taacttctgc accgggaaag gttattattt ttggtgaaca | 540 |
| ctctgctgtg tacaacaagc ctgccgtcgc tgctagtgtg tctgcgttga gaacctacct | 600 |
| gctaataagc gagtcatctg caccagatac tattgaattg gacttcccgg acattagctt | 660 |
| taatcataag tggtccatca atgatttcaa tgccatcacc gaggatcaag taaactccca | 720 |
| aaaattggcc aaggctcaac aagccaccga tggcttgtct caggaactcg ttagtctttt | 780 |
| ggatccgttg ttagctcaac tatccgaatc cttccactac catgcagcgt tttgtttcct | 840 |
| gtatatgttt gtttgcctat gccccatgc caagaatatt aagttttctt taaagtctac | 900 |
| tttacccatc ggtgctgggt tgggctcaag cgcctctatt tctgtatcac tggccttagc | 960 |
| tatggcctac ttggggggggt taataggatc taatgacttg gaaaagctgt cagaaaacga | 1020 |
| taagcatata gtgaatcaat gggccttcat aggtgaaaag tgtattcacg gtaccccttc | 1080 |

```
aggaatagat aacgctgtgg ccacttatgg taatgccctg ctatttgaaa aagactcaca    1140
taatggaaca ataaacacaa acaattttaa gttcttagat gatttcccag ccattccaat    1200
gatcctaacc tatactagaa ttccaaggtc tacaaaagat cttgttgctc gcgttcgtgt    1260
gttggtcacc gagaaatttc ctgaagttat gaagccaatt ctagatgcca tgggtgaatg    1320
tgccctacaa ggcttagaga tcatgactaa gttaagtaaa tgtaaaggca ccgatgacga    1380
ggctgtagaa actaataatg aactgtatga acaactattg gaattgataa gaataaatca    1440
tggactgctt gtctcaatcg gtgtttctca tcctggatta gaacttatta aaaatctgag    1500
cgatgatttg agaattggct ccacaaaact taccggtgct ggtggcggcg gttgctcttt    1560
gactttgtta cgaagagaca ttactcaaga gcaaattgac agcttcaaaa agaaattgca    1620
agatgatttt agttacgaga catttgaaac agacttgggt gggactggct gctgtttgtt    1680
aagcgcaaaa aatttgaata agatcttaa aatcaaatcc ctagtattcc aattatttga    1740
aaataaaact accacaaagc aacaaattga cgatctatta ttgccaggaa acacgaattt    1800
accatggact tcataagcta atttgcgata ggcctgcacc cttaaggagg aaaaaaacat    1860
gtcagagttg agagccttca gtgccccagg gaaagcgtta ctagctggtg atatttagt    1920 tttagataca aaatatgaag catttgtagt cggattatcg gcaagaatgc atgctgtagc    1980
ccatccttac ggttcattgc aagggtctga taagtttgaa gtgcgtgtga aaagtaaaca    2040
atttaaagat ggggagtggc tgtaccatat aagtcctaaa agtggcttca ttcctgtttc    2100
gataggcgga tctaagaacc cttttcattga aaaagttatc gctaacgtat ttagctactt    2160
taaacctaac atggacgact actgcaatag aaacttgttc gttattgata ttttctctga    2220
tgatgcctac cattctcagg aggatagcgt taccgaacat cgtggcaaca gaagattgag    2280
ttttcattcg cacagaattg aagaagttcc caaaacaggg ctgggctcct cggcaggttt    2340
agtcacagtt ttaactacag cttttggcctc ctttttttgta tcggacctgg aaaataatgt    2400
agacaaatat agagaagtta ttcataattt agcacaagtt gctcattgtc aagctcaggg    2460
taaaattgga agcgggtttg atgtagcggc ggcagcatat ggatctatca gatatagaag    2520
attcccaccc gcattaatct ctaatttgcc agatattgga agtgctactt acggcagtaa    2580
actggcgcat ttggttgatg aagaagactg gaatattacg attaaaagta accatttacc    2640
ttcgggatta actttatgga tgggcgatat taagaatggt tcagaaacag taaaactggt    2700
ccagaaggta aaaaattggt atgattcgca tatgccagaa agcttgaaaa tatatacaga    2760
actcgatcat gcaaattcta gatttatgga tggactatct aaactagatc gcttacacga    2820
gactcatgac gattacagcg atcagatatt tgagtctctt gagaggaatg actgtacctg    2880
tcaaaagtat cctgaaatca cagaagttag agatgcagtt gccacaatta gacgttcctt    2940
tagaaaaata actaaagaat ctggtgccga tatcgaacct cccgtacaaa ctagcttatt    3000
ggatgattgc cagaccttaa aaggagttct tacttgctta atacctggtg ctggtggtta    3060
tgacgccatt gcagtgatta ctaagcaaga tgttgatctt agggctcaaa ccgctaatga    3120
caaaagattt tctaaggttc aatggctgga tgtaactcag gctgactggg gtgttaggaa    3180
agaaaaagat ccggaaactt atcttgataa ataacttaag gtagctgcat gcagaattcg    3240
cccttaagga ggaaaaaaaa atgaccgttt acacagcatc cgttaccgca cccgtcaaca    3300
tcgcaaccct taagtattgg gggaaaaggg acacgaagtt gaatctgccc accaattcgt    3360
ccatatcagt gactttatcg caagatgacc tcagaacgtt gacctctgcg gctactgcac    3420
```

```
ctgagtttga acgcgacact tgtggttaa atggagaacc acacagcatc gacaatgaaa      3480
gaactcaaaa ttgtctgcgc gacctacgcc aattaagaaa ggaaatggaa tcgaaggacg      3540
cctcattgcc cacattatct caatggaaac tccacattgt ctccgaaaat aactttccta      3600
cagcagctgg tttagcttcc tccgctgctg gctttgctgc attggtctct gcaattgcta      3660
agttatacca attaccacag tcaacttcag aaatatctag aatagcaaga aagggtctg       3720 gttcagcttg tagatcgttg tttggcggat acgtggcctg ggaatggga aaagctgaag       3780 atggtcatga ttccatggca gtacaaatcg cagacagctc tgactggcct cagatgaaag      3840
cttgtgtcct agttgtcagc gatattaaaa aggatgtgag ttccactcag ggtatgcaat      3900
tgaccgtggc aacctccgaa ctatttaaag aaagaattga acatgtcgta ccaaagagat      3960
ttgaagtcat gcgtaaagcc attgttgaaa aagatttcgc ccctttgca aaggaaacaa       4020 tgatggattc caactctttc catgccacat gtttggactc tttccctcca atattctaca      4080
tgaatgacac ttccaagcgt atcatcagtt ggtgccacac cattaatcag ttttacggag      4140
aaacaatcgt tgcatacacg tttgatgcag gtccaaatgc tgtgttgtac tacttagctg      4200
aaaatgagtc gaaactcttt gcatttatct ataaattgtt tggctctgtt cctggatggg      4260
acaagaaatt tactactgag cagcttgagg cttcaacca tcaatttgaa tcatctaact       4320
ttactgcacg tgaattggat cttgagttgc aaaaggatgt tgccagagtg attttaactc      4380
aagtcggttc aggcccacaa gaaacaaacg aatctttgat tgacgcaaag actggtctac      4440
caaaggaata agatcaattc gctgcatcgc ccttaggagg taaaaaaaaa tgactgccga      4500
caacaatagt atgcccatg tgtgcagtatc tagttacgcc aaattagtgc aaaaccaaac       4560
acctgaagac attttggaag agtttcctga aattattcca ttacaacaaa gacctaatac      4620 ccgatcagt gagacgtcaa atgacgaaag cggagaaaca tgttttcctg gtcatgatga       4680
ggagcaaatt aagttaatga atgaaaattg tattgttttg gattgggacg ataatgctat      4740
tggtgccggt accaagaaag tttgtcattt aatggaaaat attgaaaagg gtttactaca      4800
tcgtgcattc tccgtcttta ttttcaatga acaaggtgaa ttactttac aacaaagagc       4860 cactgaaaaa ataactttcc ctgatctttg gactaacaca tgctgctctc atccactatg      4920
tattgatgac gaattaggtt tgaagggtaa gctagacgat aagattaagg gcgctattac      4980
tgcggcggtg agaaaactag atcatgaatt aggtattcca gaagatgaaa ctaagacaag      5040
gggtaagttt cacttttttaa acagaatcca ttacatggca ccaagcaatg aaccatgggg      5100
tgaacatgaa attgattaca tcctatttta aagatcaac gctaaagaaa acttgactgt       5160
caacccaaac gtcaatgaag ttagagactt caaatgggtt tcaccaaatg atttgaaaac      5220
tatgtttgct gacccaagtt acaagtttac gccttggttt aagattattt gcgagaatta      5280
cttattcaac tggtgggagc aattagatga cctttctgaa gtggaaaatg acaggcaaat      5340
tcatagaatg ctataacaac gcgtcctgca ttcgccctta ggaggtaaaa aaacatgtgt      5400
gcgacctctt ctcaatttac tcagattacc gagcataatt cccgtcgttc cgcaaactat      5460
cagccaaacc tgtggaattt cgaattcctg caatccctgg agaacgacct gaaagtggaa      5520
aagctggaga gaaagcgac caaactggag gaagaagttc gctgcatgat caaccgtgta      5580
gacacccagc cgctgtccct gctggagctg atcgacgatg tgcagcgcct gggtctgacc      5640
tacaaatttg aaaagacat cattaaagcc ctgaaaaaca tcgtactgct ggacgaaaac       5700
aaaaagaaca atctgacct gcacgcaacc gctctgtctt tccgtctgct gcgtcagcac       5760
ggtttcgagg tttctcagga tgttttgag cgtttcaagg ataaagaagg tggtttcagc      5820
```

-continued

```
ggtgaactga aaggtgacgt ccaaggcctg ctgagcctgt atgaagcgtc ttacctgggt    5880
ttcgagggtg agaacctgct ggaggaggcg cgtaccttt  ccatcaccca cctgaagaac    5940
aacctgaaag aaggcattaa taccaaggtt gcagaacaag tgagccacgc cctggaactg    6000
ccatatcacc agcgtctgca ccgtctggag gcacgttggt tcctggataa atacgaaccg    6060
aaagaaccgc atcaccagct gctgctggag ctggcgaagc tggattttaa catggtacag    6120
accctgcacc agaaagagct gcaagatctg tcccgctggt ggaccgagat gggcctggct    6180
agcaaactgg attttgtacg cgaccgcctg atggaagttt atttctgggc actgggtatg    6240
gcgccagacc gcagtttgg tgaatgtcgc aaagctgtta ctaaaatgtt tggtctggtg    6300
acgatcatcg atgacgtgta tgacgtttat ggcactctgg acgaactgca actgttcacc    6360
gatgctgtag agcgctggga cgttaacgct attaacaccc tgccggacta tatgaaactg    6420
tgtttcctgg cactgtacaa caccgttaac gacacgtcct attctattct gaaagagaaa    6480
ggtcataaca acctgtccta tctgacgaaa agctggcgtg aactgtgcaa agcctttctg    6540
caagaggcga atggtccaa  caacaaaatt atcccggctt ctccaagta cctggaaaac    6600
gccagcgttt cctcctccgg tgtagcgctg ctggcgccgt cttactttc cgtatgccag    6660
cagcaggaag acatctccga ccacgcgctg cgttccctga ccgacttcca tggtctggtg    6720
cgttctagct gcgttatctt ccgcctgtgc aacgatctgg ccacctctgc ggcggagctg    6780
gaacgtggcg agactaccaa ttctatcatt agctacatgc acgaaaacga tggtaccagc    6840
gaggaacagg cccgcgaaga actgcgtaaa ctgatcgacg ccgaatggaa aaagatgaat    6900
cgtgaacgcg ttagcgactc caccctgctg cctaaagcgt tcatggaaat cgcagttaac    6960
atggcacgtg tttcccactg cacctaccag tatggcgatg gtctgggtcg cccagactac    7020
gcgactgaaa accgcatcaa actgctgctg attgacccctt tcccgattaa ccagctgatg    7080
tatgtctaac tgcagctggt accatatggg aattcgaagc tttctagaac aaaaactcat    7140
ctcagaagag gatctgaata gcgccgtcga ccatcatcat catcatcatt gagtttaaac    7200
ggtctccagc ttggctgttt tggcggatga gagaagattt tcagcctgat acagattaaa    7260
tcagaacgca gaagcggtct gataaaacag aatttgcctg gcggcagtag cgcggtggtc    7320
ccacctgacc ccatgccgaa ctcagaagtg aaacgccgta gcgccgatgg tagtgtgggg    7380
tctccccatg cgagagtagg gaactgccag gcatcaaata aaacgaaagg ctcagtcgaa    7440
agactgggcc tttcgtttta tctgttgttt gtcggtgaac gctctcctga gtaggacaaa    7500
tccgccggga gcggatttga acgttgcgaa gcaacggccc ggagggtggc gggcaggacg    7560
cccgccataa actgccaggc atcaaattaa gcagaaggcc atcctgacgg atggcctttt    7620
tgcgtttcta caaactcttt tgtttattt  ttctaaatac attcaaatat gtatccgctc    7680
atgagacaat aaccctgata aatgcttcaa taatattgaa aaggaagag  tatgagtatt    7740
caacatttcc gtgtcgccct tattccctt  tttgcggcat tttgccttcc tgttttgct    7800
cacccagaaa cgctggtgaa agtaaaagat gctgaagatc agttgggtgc acgagtgggt    7860
tacatcgaac tggatctcaa cagcggtaag atccttgaga gttttcgccc cgaagaacgt    7920
tttccaatga tgagcacttt taaagttctg ctatgtggcg cggtattatc ccgtgttgac    7980
gccgggcaag agcaactcgg tcgccgcata cactattctc agaatgactt ggttgagtac    8040
tcaccagtca cagaaaagca tcttacggat ggcatgacag taagagaatt atgcagtgct    8100
gccataacca tgagtgataa cactgcggcc aacttacttc tgacaacgat cggaggaccg    8160
```

```
aaggagctaa ccgcttttt  gcacaacatg ggggatcatg taactcgcct tgatcgttgg   8220
gaaccggagc tgaatgaagc cataccaaac gacgagcgtg acaccacgat gcctgtagca   8280
atggcaacaa cgttgcgcaa actattaact ggcgaactac ttactctagc ttcccggcaa   8340
caattaatag actggatgga ggcggataaa gttgcaggac cacttctgcg ctcggccctt   8400
ccggctggct ggtttattgc tgataaatct ggagccggtg agcgtgggtc tcgcggtatc   8460
attgcagcac tggggccaga tggtaagccc tcccgtatcg tagttatcta cacgacgggg   8520
agtcaggcaa ctatggatga acgaaataga cagatcgctg agataggtgc ctcactgatt   8580
aagcattggt aactgtcaga ccaagtttac tcatatatac tttagattga tttaaaactt   8640
catttttaat ttaaaaggat ctaggtgaag atccttttg  ataatctcat gaccaaaatc   8700
ccttaacgtg agttttcgtt ccactgagcg tcagacccccg tagaaaagat caaaggatct   8760
tcttgagatc cttttttct  gcgcgtaatc tgctgcttgc aaacaaaaaa accaccgcta   8820
ccagcggtgg tttgtttgcc ggatcaagag ctaccaactc tttttccgaa ggtaactggc   8880
ttcagcagag cgcagatacc aaatactgtc cttctagtgt agccgtagtt aggccaccac   8940
ttcaagaact ctgtagcacc gcctacatac ctcgctctgc taatcctgtt accagtggct   9000
gctgccagtg gcgataagtc gtgtcttacc gggttggact caagacgata gttaccggat   9060
aaggcgcagc ggtcgggctg aacggggggt tcgtgcacac agcccagctt ggagcgaacg   9120
acctacaccg aactgagata cctacagcgt gagctatgag aaagcgccac gcttcccgaa   9180
gggagaaagg cggacaggta tccggtaagc ggcagggtcg aacaggaga  gcgcacgagg   9240
gagcttccag ggggaaacgc ctggtatctt tatagtcctg tcgggtttcg ccacctctga   9300
cttgagcgtc gatttttgtg atgctcgtca ggggggcgga gcctatggaa aaacgccagc   9360
aacgcggcct ttttacggtt cctggccttt tgctggcctt tgctcacat  gttctttcct   9420
gcgttatccc ctgattctgt ggataaccgt attaccgcct ttgagtgagc tgataccgct   9480
cgccgcagcc gaacgaccga gcgcagcgag tcagtgagcg aggaagcgga agagcgcctg   9540
atgcggtatt ttctccttac gcatctgtgc ggtatttcac accgcatatg gtgcactctc   9600
agtacaatct gctctgatgc cgcatagtta agccagtata cactccgcta tcgctacgtg   9660
actgggtcat ggctgcgccc cgacacccgc caacacccgc tgacgcgccc tgacgggctt   9720
gtctgctccc ggcatccgct tacagacaag ctgtgaccgt ctccgggagc tgcatgtgtc   9780
agaggttttc accgtcatca ccgaaacgcg cgaggcagca gatcaattcg cgcgcgaagg   9840
cgaagcggca tgcatttacg ttgacaccat cgaatggtgc aaaacctttc gcggtatggc   9900
atgatagcgc ccggaagaga gtcaattcag ggtggtgaat gtgaaaccag taacgttata   9960
cgatgtcgca gagtatgccg gtgtctctta tcagaccgtt tccgcgtgg  tgaaccaggc  10020
cagccacgtt tctgcgaaaa cgcgggaaaa agtggaagcg gcgatggcgg agctgaatta  10080
cattcccaac cgcgtggcac aacaactggc gggcaaacag tcgttgctga ttggcgttgc  10140
cacctccagt ctggccctgc acgcgccgtc gcaaattgtc gcggcgatta atctcgcgc   10200
cgatcaactg ggtgccagcg tggtggtgtc gatggtagaa cgaagcggcg tcgaagcctg  10260
taaagcggcg gtgcacaatc ttctcgcgca acgcgtcagt gggctgatca ttaactatcc  10320
gctggatgac caggatgcca ttgctgtgga agctgcctgc actaatgttc cggcgttatt  10380
tcttgatgtc tctgaccaga cacccatcaa cagtattatt ttctcccatg aagacggtac  10440
gcgactgggc gtggagcatc tggtcgcatt gggtcaccag caaatcgcgc tgttagcggg  10500
cccattaagt tctgtctcgg cgcgtctgcg tctggctggc tggcataaat atctcactcg  10560
```

```
caatcaaatt cagccgatag cggaacggga aggcgactgg agtgccatgt ccggttttca    10620
acaaaccatg caaatgctga atgagggcat cgttcccact gcgatgctgg ttgccaacga    10680
tcagatggcg ctgggcgcaa tgcgcgccat taccgagtcc gggctgcgcg ttggtgcgga    10740
tatctcggta gtgggatacg acgataccga agacagctca tgttatatcc cgccgtcaac    10800
caccatcaaa caggattttc gcctgctggg gcaaaccagc gtggaccgct tgctgcaact    10860
ctctcagggc caggcggtga agggcaatca gctgttgccc gtctcactgg tgaaaagaaa    10920
aaccaccctg gcgcccaata cgcaaaccgc ctctccccgc gcgttggccg attcattaat    10980
gcagctggca cgacaggttt cccgactgga aagcgggcag tgagcgcaac gcaattaatg    11040
tgagttagcg cgaattgatc tg                                             11062
```

<210> SEQ ID NO 75
<211> LENGTH: 80
<212> TYPE: DNA
<213> ORGANISM: Artificial Sequence
<220> FEATURE:
<223> OTHER INFORMATION: Primer for amplifying a fragment comprising
      kanamycin-resistance gene and tac promoter (P4071R_6083-54-1)

<400> SEQUENCE: 75

```
ccaaaaataa taacctttcc cggtgcagaa gttaagaacg gtaatgacat ggcagtctcc    60
ttgtgtgaaa ttgttatccg                                                80
```

<210> SEQ ID NO 76
<211> LENGTH: 80
<212> TYPE: DNA
<213> ORGANISM: Artificial Sequence
<220> FEATURE:
<223> OTHER INFORMATION: Primer for amplifying a fragment comprising
      kanamycin-resistance gene and tac promoter (P4071F(2)_6083-54-3)

<400> SEQUENCE: 76

```
tcattgtaat acgcgtaatt ccggtgcctg tagtacccag gcgcagcttt tgaagcctgc    60
ttttttatac taagttggca                                                80
```

<210> SEQ ID NO 77
<211> LENGTH: 20
<212> TYPE: DNA
<213> ORGANISM: Artificial Sequence
<220> FEATURE:
<223> OTHER INFORMATION: Primer for confirming insertion of a certain
      insert into a region upstream of KKDyI operon (FCK_6038-52-3)

<400> SEQUENCE: 77

```
cgcaaaatgt gatctctcca                                                20
```

<210> SEQ ID NO 78
<211> LENGTH: 20
<212> TYPE: DNA
<213> ORGANISM: Artificial Sequence
<220> FEATURE:
<223> OTHER INFORMATION: Primer for confirming insertion of a certain
      insert into a region upstream of KKDyI operon (RCK_6038-52-4)

<400> SEQUENCE: 78

```
cgattgagac aagcagtcca                                                20
```

<210> SEQ ID NO 79
<211> LENGTH: 68
<212> TYPE: DNA

<213> ORGANISM: Artificial Sequence
<220> FEATURE:
<223> OTHER INFORMATION: Primer (DampC-phL)

<400> SEQUENCE: 79
ctgatgaact gtcacctgaa tgagtgctga tgaaaatata gaaaggtcat ttttcctgaa    60
tatgctca    68

<210> SEQ ID NO 80
<211> LENGTH: 64
<212> TYPE: DNA
<213> ORGANISM: Artificial Sequence
<220> FEATURE:
<223> OTHER INFORMATION: Primer (DampC-phR)

<400> SEQUENCE: 80
attcgccagc ataacgatgc cgctgttgag ctgaggaaca cgtttgttga cagctggtcc    60
aatg    64

<210> SEQ ID NO 81
<211> LENGTH: 70
<212> TYPE: DNA
<213> ORGANISM: Artificial Sequence
<220> FEATURE:
<223> OTHER INFORMATION: Primer (ampH-attL-phi80)

<400> SEQUENCE: 81
atgcgcactc cttacgtact ggctctactg gtttctttgc gaaaggtcat ttttcctgaa    60
tatgctcaca    70

<210> SEQ ID NO 82
<211> LENGTH: 64
<212> TYPE: DNA
<213> ORGANISM: Artificial Sequence
<220> FEATURE:
<223> OTHER INFORMATION: Primer (ampH-attR-phi80)

<400> SEQUENCE: 82
ttaaggaatc gcctggacca tcatcggcga gccgttctga cgtttgttga cagctggtcc    60
aatg    64

<210> SEQ ID NO 83
<211> LENGTH: 68
<212> TYPE: DNA
<213> ORGANISM: Artificial Sequence
<220> FEATURE:
<223> OTHER INFORMATION: Primer (crtZ-attLphi80)

<400> SEQUENCE: 83
atgttgtgga tttggaatgc cctgatcgtt tcgttaccg gaaaggtcat ttttcctgaa    60
tatgctca    68

<210> SEQ ID NO 84
<211> LENGTH: 64
<212> TYPE: DNA
<213> ORGANISM: Artificial Sequence
<220> FEATURE:
<223> OTHER INFORMATION: Primer (crtE-attRphi80)

<400> SEQUENCE: 84
atgacggtct gcgcaaaaaa acacgttcat ctcactcgcg cgtttgttga cagctggtcc    60
aatg    64

<210> SEQ ID NO 85
<211> LENGTH: 21
<212> TYPE: DNA
<213> ORGANISM: Artificial Sequence
<220> FEATURE:
<223> OTHER INFORMATION: Primer (ampC-t1)

<400> SEQUENCE: 85
gattcccact tcaccgagcc g                                                    21

<210> SEQ ID NO 86
<211> LENGTH: 21
<212> TYPE: DNA
<213> ORGANISM: Artificial Sequence
<220> FEATURE:
<223> OTHER INFORMATION: Primer (ampC-t2)

<400> SEQUENCE: 86
ggcaggtatg gtgctctgac g                                                    21

<210> SEQ ID NO 87
<211> LENGTH: 18
<212> TYPE: DNA
<213> ORGANISM: Artificial Sequence
<220> FEATURE:
<223> OTHER INFORMATION: Primer (ampH-t1)

<400> SEQUENCE: 87
gcgaagccct ctccgttg                                                        18

<210> SEQ ID NO 88
<211> LENGTH: 21
<212> TYPE: DNA
<213> ORGANISM: Artificial Sequence
<220> FEATURE:
<223> OTHER INFORMATION: Primer (ampH-t2)

<400> SEQUENCE: 88
agccagtcag cctcatcagc g                                                    21

<210> SEQ ID NO 89
<211> LENGTH: 21
<212> TYPE: DNA
<213> ORGANISM: Artificial Sequence
<220> FEATURE:
<223> OTHER INFORMATION: Primer (crtZ-test)

<400> SEQUENCE: 89
ccgtgtggtt ctgaaagccg a                                                    21

<210> SEQ ID NO 90
<211> LENGTH: 21
<212> TYPE: DNA
<213> ORGANISM: Artificial Sequence
<220> FEATURE:
<223> OTHER INFORMATION: Primer (crtE-test)

<400> SEQUENCE: 90
cgttgccgta aatgtatccg t                                                    21

<210> SEQ ID NO 91
<211> LENGTH: 27
<212> TYPE: DNA
<213> ORGANISM: Artificial Sequence
<220> FEATURE:

<223> OTHER INFORMATION: Primer (ag-phL-test)

<400> SEQUENCE: 91
gttcgcagag tgttatggtt tacatcc                                    27

<210> SEQ ID NO 92
<211> LENGTH: 25
<212> TYPE: DNA
<213> ORGANISM: Artificial Sequence
<220> FEATURE:
<223> OTHER INFORMATION: Primer (ag-phR-test)

<400> SEQUENCE: 92
gattggtggt tgaattgtcc gtaac                                      25

<210> SEQ ID NO 93
<211> LENGTH: 22
<212> TYPE: DNA
<213> ORGANISM: Artificial Sequence
<220> FEATURE:
<223> OTHER INFORMATION: Primer (KKDyI-s-3')

<400> SEQUENCE: 93
tggaaggatt cggatagttg ag                                         22

<210> SEQ ID NO 94
<211> LENGTH: 18
<212> TYPE: DNA
<213> ORGANISM: Artificial Sequence
<220> FEATURE:
<223> OTHER INFORMATION: Primer (mvaES-s-3')

<400> SEQUENCE: 94
ggcaatcagc acttccgc                                              18

<210> SEQ ID NO 95
<211> LENGTH: 23
<212> TYPE: DNA
<213> ORGANISM: Artificial Sequence
<220> FEATURE:
<223> OTHER INFORMATION: Primer (ispS-Seq2)

<400> SEQUENCE: 95
ggttcgtatt tatccagcag cca                                        23

<210> SEQ ID NO 96
<211> LENGTH: 34
<212> TYPE: DNA
<213> ORGANISM: Artificial Sequence
<220> FEATURE:
<223> OTHER INFORMATION: Primer (tac5HindIII)

<400> SEQUENCE: 96
gcttaaagct tccctgttga caattaatca tcgg                            34

<210> SEQ ID NO 97
<211> LENGTH: 35
<212> TYPE: DNA
<213> ORGANISM: Artificial Sequence
<220> FEATURE:
<223> OTHER INFORMATION: Primer (tac3SphI)

<400> SEQUENCE: 97
ctgttgcatg ctgtgtgaaa ttgttatccg ctcac                           35

-continued

<210> SEQ ID NO 98
<211> LENGTH: 595
<212> TYPE: PRT
<213> ORGANISM: Populus alba x Populus tremula

<400> SEQUENCE: 98

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Phe Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Gly Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Thr Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Arg Val Phe Ala Ile Ser His Leu Lys Glu Leu Ser Glu
    210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Lys Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
    370                 375                 380

```
Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
            405                 410                 415

Cys Asn Ala Phe Leu Gln Glu Ala Lys Trp Leu Tyr Asn Lys Ser Thr
        420                 425                 430

Pro Thr Phe Asp Asp Tyr Phe Gly Asn Ala Trp Lys Ser Ser Ser Gly
    435                 440                 445

Pro Leu Gln Leu Ile Phe Ala Tyr Phe Ala Val Val Gln Asn Ile Lys
        450                 455                 460

Lys Glu Glu Ile Glu Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
            485                 490                 495

Glu Ile Ala Arg Gly Glu Thr Ala Asn Ser Val Ser Cys Tyr Met Arg
                500                 505                 510

Thr Lys Gly Ile Ser Glu Glu Leu Ala Thr Glu Ser Val Met Asn Leu
            515                 520                 525

Ile Asp Glu Thr Cys Lys Lys Met Asn Lys Glu Lys Leu Gly Gly Ser
530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595

<210> SEQ ID NO 99
<211> LENGTH: 594
<212> TYPE: PRT
<213> ORGANISM: Mucuna bracteata

<400> SEQUENCE: 99

Met Ala Thr Asn Pro Ser Cys Leu Ser Thr Pro Phe Leu Ser Ser Thr
1               5                   10                  15

Pro Ala Leu Ser Thr Arg Phe Pro Leu Ser Glu Asn Phe Thr Gln Lys
            20                  25                  30

Thr Ser Leu Val Asn Pro Lys Pro Trp Pro Leu Ile Ser Ala Val Ser
        35                  40                  45

Ser Gln Phe Ser Gln Ile Ala Glu Asp Asn Ser Arg Arg Ser Ala Asn
    50                  55                  60

Tyr His Pro Asn Leu Trp Asp Phe Glu Phe Gln Ser Leu Glu Asn
65                  70                  75                  80

Asp Ser Lys Met Glu Lys Leu Glu Glu Lys Ala Thr Lys Leu Glu Glu
                85                  90                  95

Glu Val Arg Asn Met Met Asn Glu Ala Lys Thr Glu Ala Leu Ser Leu
            100                 105                 110

Leu Glu Leu Ile Asp Asp Val Gln Arg Leu Gly Leu Thr Tyr Lys Phe
        115                 120                 125

Glu Lys Asp Ile Ile Lys Ala Leu Glu Lys Ile Val Pro Leu Asp Glu
    130                 135                 140

Ser Gly Leu His Val Thr Ser Leu Ser Phe Arg Ile Leu Arg Gln His
145                 150                 155                 160
```

```
Gly Phe Glu Val Ser Gln Asp Val Phe Lys Arg Phe Lys Asp Lys Glu
                165                 170                 175
Gly Gly Phe Cys Ala Glu Leu Lys Asp Asp Val Gln Gly Leu Leu Ser
            180                 185                 190
Leu Tyr Glu Ala Ser Tyr Leu Gly Phe Glu Gly Glu Ser Leu Leu Asp
        195                 200                 205
Glu Ala Arg Ala Phe Ser Ile Thr His Leu Lys Asn Asn Leu Asn Lys
    210                 215                 220
Gly Ile Asn Thr Lys Val Ala Gln Gln Val Ser His Ala Leu Glu Leu
225                 230                 235                 240
Pro Tyr His Arg Arg Leu His Arg Leu Glu Ala Arg Trp Leu Leu Asp
                245                 250                 255
Lys Tyr Glu Pro Lys Glu Pro His His His Leu Leu His Glu Leu Ala
            260                 265                 270
Lys Leu Asp Phe Asn Leu Val Gln Ser Leu Tyr Gln Lys Glu Leu Arg
        275                 280                 285
Glu Leu Ser Leu Trp Trp Arg Glu Ile Gly Leu Thr Ser Lys Leu Asp
    290                 295                 300
Phe Val Arg Asp Arg Leu Met Glu Val Tyr Phe Trp Ala Leu Gly Met
305                 310                 315                 320
Ala Pro Asp Pro Gln Phe Ser Glu Cys Arg Lys Val Val Thr Lys Met
                325                 330                 335
Phe Gly Leu Val Thr Ile Ile Asp Asp Val Tyr Asp Val Tyr Gly Thr
            340                 345                 350
Leu Asp Glu Leu Gln Leu Phe Thr Asp Ala Val Glu Arg Trp Asp Val
        355                 360                 365
Asn Ala Ile Asn Thr Leu Pro Asp Tyr Met Lys Leu Cys Tyr Leu Ala
    370                 375                 380
Leu Tyr Asn Thr Val Asn Asp Thr Ala Tyr Ser Ile Leu Lys Glu Lys
385                 390                 395                 400
Gly His Asn Asn Ile Ser Tyr Leu Thr Lys Ser Trp Cys Glu Leu Cys
                405                 410                 415
Lys Ala Phe Leu Gln Glu Ala Lys Trp Ser Asn Asn Lys Ile Ile Pro
            420                 425                 430
Ala Phe Asn Lys Tyr Leu Asp Asn Ala Ser Val Ser Ser Ser Gly Val
        435                 440                 445
Ala Leu Leu Ala Pro Ser Tyr Phe Leu Val Cys Gln Glu Gln Asp Ile
    450                 455                 460
Ser Asp Gln Ala Leu His Ser Leu Thr Asn Phe His Gly Leu Val Arg
465                 470                 475                 480
Ser Ser Cys Thr Ile Phe Arg Leu Cys Asn Asp Leu Ala Thr Ser Ser
                485                 490                 495
Ala Glu Leu Glu Arg Gly Glu Thr Thr Asn Ser Ile Thr Ser Tyr Met
            500                 505                 510
His Glu Asn Glu Thr Ser Glu Glu Gln Ala Cys Lys Glu Leu Arg Asn
        515                 520                 525
Leu Ile Asp Ala Glu Trp Lys Lys Met Asn Glu Glu Arg Val Ser Asn
    530                 535                 540
Ser Thr Leu Pro Lys Ala Phe Arg Glu Ile Ala Ile Asn Met Ala Arg
545                 550                 555                 560
Ile Ser His Cys Thr Tyr Gln Tyr Gly Asp Gly Leu Gly Arg Pro Asp
                565                 570                 575
```

Tyr Thr Thr Glu Asn Arg Ile Lys Leu Leu Leu Ile Asp Pro Phe Pro
        580                 585                 590

Ile Asn

<210> SEQ ID NO 100
<211> LENGTH: 40
<212> TYPE: DNA
<213> ORGANISM: Artificial Sequence
<220> FEATURE:
<223> OTHER INFORMATION: Primer 1 for amplifying ERG12mvk gene (SMVKf)

<400> SEQUENCE: 100
tttcacacaa ggagactccc atgtcattac cgttcttaac                    40

<210> SEQ ID NO 101
<211> LENGTH: 40
<212> TYPE: DNA
<213> ORGANISM: Artificial Sequence
<220> FEATURE:
<223> OTHER INFORMATION: Primer 2 for amplifying ERG12mvk gene (SMVKr)

<400> SEQUENCE: 101
cagcggaact ggcggctccc ttatgaagtc catggtaaat                    40

<210> SEQ ID NO 102
<211> LENGTH: 36
<212> TYPE: DNA
<213> ORGANISM: Artificial Sequence
<220> FEATURE:
<223> OTHER INFORMATION: Primer (mcl-mvk-Nde-F)

<400> SEQUENCE: 102
gcaattccat atgacgatgg cttccgctcc gggcaa                        36

<210> SEQ ID NO 103
<211> LENGTH: 33
<212> TYPE: DNA
<213> ORGANISM: Artificial Sequence
<220> FEATURE:
<223> OTHER INFORMATION: Primer (mcl-mvk-Hind-R)

<400> SEQUENCE: 103
cccaagctta cgcgacttcc aggcgaacac ctt                           33

<210> SEQ ID NO 104
<211> LENGTH: 36
<212> TYPE: DNA
<213> ORGANISM: Artificial Sequence
<220> FEATURE:
<223> OTHER INFORMATION: Primer (mpd-mvk-NdeI-F)

<400> SEQUENCE: 104
gcaattccat atgacgatgt gttcagcccc cggtaa                        36

<210> SEQ ID NO 105
<211> LENGTH: 30
<212> TYPE: DNA
<213> ORGANISM: Artificial Sequence
<220> FEATURE:
<223> OTHER INFORMATION: Primer (mpd-mvk-NdeI-mut-F)

<400> SEQUENCE: 105
ggatgcatgg tggccatttg cgatgacaaa                               30

<210> SEQ ID NO 106

```
<211> LENGTH: 30
<212> TYPE: DNA
<213> ORGANISM: Artificial Sequence
<220> FEATURE:
<223> OTHER INFORMATION: Primer (mpd-mvk-NdeI-mut-R)

<400> SEQUENCE: 106
tttgtcatcg caaatggcca ccatgcatcc                                   30

<210> SEQ ID NO 107
<211> LENGTH: 35
<212> TYPE: DNA
<213> ORGANISM: Artificial Sequence
<220> FEATURE:
<223> OTHER INFORMATION: Primer (mpd-mvk-Hind-R)

<400> SEQUENCE: 107
cccaagctta ttggatgaat attccctccg ccgtt                             35

<210> SEQ ID NO 108
<211> LENGTH: 33
<212> TYPE: DNA
<213> ORGANISM: Artificial Sequence
<220> FEATURE:
<223> OTHER INFORMATION: Primer (nmr-mvk-NdeI-F)

<400> SEQUENCE: 108
gcaattccat atgaagagca aggcatctgc gcc                               33

<210> SEQ ID NO 109
<211> LENGTH: 34
<212> TYPE: DNA
<213> ORGANISM: Artificial Sequence
<220> FEATURE:
<223> OTHER INFORMATION: Primer (nmr-mvk-Hind-R)

<400> SEQUENCE: 109
cccaagctta aaacgtgtcc aggcccttga aatc                              34

<210> SEQ ID NO 110
<211> LENGTH: 30
<212> TYPE: DNA
<213> ORGANISM: Artificial Sequence
<220> FEATURE:
<223> OTHER INFORMATION: Primer (cva-mvk-NdeI-F)

<400> SEQUENCE: 110
gcaattccat atggccccgc acgtcggtca                                   30

<210> SEQ ID NO 111
<211> LENGTH: 37
<212> TYPE: DNA
<213> ORGANISM: Artificial Sequence
<220> FEATURE:
<223> OTHER INFORMATION: Primer (cva-mvk-Hind-R)

<400> SEQUENCE: 111
cccaagctta ttgcatcact tcacctgcca tctgacc                           37

<210> SEQ ID NO 112
<211> LENGTH: 32
<212> TYPE: DNA
<213> ORGANISM: Artificial Sequence
<220> FEATURE:
<223> OTHER INFORMATION: Primer (mma-mvk-NdeI-F)

<400> SEQUENCE: 112
```
gcaattccat atggtatcct gttctgcgcc gg    32

<210> SEQ ID NO 113
<211> LENGTH: 35
<212> TYPE: DNA
<213> ORGANISM: Artificial Sequence
<220> FEATURE:
<223> OTHER INFORMATION: Primer (mma-mvk-Hind-R)

<400> SEQUENCE: 113
cccaagctta atctactttc agaccttgct cggtc    35

<210> SEQ ID NO 114
<211> LENGTH: 36
<212> TYPE: DNA
<213> ORGANISM: Artificial Sequence
<220> FEATURE:
<223> OTHER INFORMATION: Primer (sce-mvk-NdeI-F)

<400> SEQUENCE: 114
gcaattgcat atgtcattac cgttcttaac ttctgc    36

<210> SEQ ID NO 115
<211> LENGTH: 34
<212> TYPE: DNA
<213> ORGANISM: Artificial Sequence
<220> FEATURE:
<223> OTHER INFORMATION: Primer (sce-mvk-Hind-R)

<400> SEQUENCE: 115
cccaagctta tgaagtccat ggtaaattcg tgtt    34

<210> SEQ ID NO 116
<211> LENGTH: 32
<212> TYPE: DNA
<213> ORGANISM: Artificial Sequence
<220> FEATURE:
<223> OTHER INFORMATION: Primer [mcl-mvk-H-HindR(pET21)]

<400> SEQUENCE: 116
cccaagcttc gcgacttcca ggcgaacacc tt    32

<210> SEQ ID NO 117
<211> LENGTH: 34
<212> TYPE: DNA
<213> ORGANISM: Artificial Sequence
<220> FEATURE:
<223> OTHER INFORMATION: Primer [mpd-mvk-H-HindR(pET21)]

<400> SEQUENCE: 117
cccaagcttt tggatgaata ttccctccgc cgtt    34

<210> SEQ ID NO 118
<211> LENGTH: 33
<212> TYPE: DNA
<213> ORGANISM: Artificial Sequence
<220> FEATURE:
<223> OTHER INFORMATION: Primer [nmr-mvk-H-Hind-R(pET21)]

<400> SEQUENCE: 118
cccaagctta aacgtgtcca ggcccttgaa atc    33

<210> SEQ ID NO 119
<211> LENGTH: 36
<212> TYPE: DNA

<213> ORGANISM: Artificial Sequence
<220> FEATURE:
<223> OTHER INFORMATION: Primer [cva-mvk-H-Hind-R(pET21)]

<400> SEQUENCE: 119
cccaagcttt tgcatcactt cacctgccat ctgacc    36

<210> SEQ ID NO 120
<211> LENGTH: 34
<212> TYPE: DNA
<213> ORGANISM: Artificial Sequence
<220> FEATURE:
<223> OTHER INFORMATION: Primer [mma-mvk-H-Hind-R(pET21)]

<400> SEQUENCE: 120
cccaagctta tctactttca gaccttgctc ggtc    34

<210> SEQ ID NO 121
<211> LENGTH: 34
<212> TYPE: DNA
<213> ORGANISM: Artificial Sequence
<220> FEATURE:
<223> OTHER INFORMATION: Primer [ce-mvk-H-Hind-R(pET21)]

<400> SEQUENCE: 121
cccaagctta tgaagtccat ggtaaattcg tgtt    34

<210> SEQ ID NO 122
<211> LENGTH: 38
<212> TYPE: DNA
<213> ORGANISM: Artificial Sequence
<220> FEATURE:
<223> OTHER INFORMATION: Primer (PMK-IFS_5742-33-3)

<400> SEQUENCE: 122
acacaaggag actcccatgt cagagttgag agccttca    38

<210> SEQ ID NO 123
<211> LENGTH: 46
<212> TYPE: DNA
<213> ORGANISM: Artificial Sequence
<220> FEATURE:
<223> OTHER INFORMATION: Primer (PMK-IFA_5742-33-4)

<400> SEQUENCE: 123
ggaactggcg gctcccgggt tattatttat caagataagt ttccgg    46

<210> SEQ ID NO 124
<211> LENGTH: 28
<212> TYPE: DNA
<213> ORGANISM: Artificial Sequence
<220> FEATURE:
<223> OTHER INFORMATION: Primer for amplifying a PMK-coding DNA

<400> SEQUENCE: 124
tcagagttga gagccttcag tgccccag    28

<210> SEQ ID NO 125
<211> LENGTH: 38
<212> TYPE: DNA
<213> ORGANISM: Artificial Sequence
<220> FEATURE:

```
<223> OTHER INFORMATION: Primer for amplifying a PMK-coding DNA

<400> SEQUENCE: 125
ggaattctct ttatcaagat aagtttccgg atcttttt                              38
```